United States Patent
Lohman et al.

(10) Patent No.: US 12,188,011 B2
(45) Date of Patent: Jan. 7, 2025

(54) COMPOSITIONS AND METHODS FOR IMPROVED IN VITRO ASSEMBLY OF POLYNUCLEOTIDES

(71) Applicant: New England Biolabs, Inc., Ipswich, MA (US)

(72) Inventors: Gregory Lohman, Cambridge, MA (US); Vladimir Potapov, Auburndale, MA (US); John M. Pryor, Gerogetown, MA (US); Rebecca Kucera, Hamilton, MA (US); Katharina Bilotti, Burlington, MA (US); Richard D. Morgan, Middleton, MA (US)

(73) Assignee: New England Biolabs, Inc., Ipswich, MA (US)

(*) Notice: Subject to any disclaimer, the term of this patent is extended or adjusted under 35 U.S.C. 154(b) by 343 days.

(21) Appl. No.: 17/644,987

(22) Filed: Dec. 17, 2021

(65) Prior Publication Data

US 2022/0177875 A1    Jun. 9, 2022

Related U.S. Application Data

(63) Continuation-in-part of application No. 17/644,516, filed on Dec. 15, 2021, which is a continuation-in-part of application No. 17/286,066, filed as application No. PCT/US2019/056670 on Oct. 17, 2019.

(60) Provisional application No. 63/213,859, filed on Jun. 23, 2021, provisional application No. 63/213,807, filed on Jun. 23, 2021, provisional application No. 63/125,530, filed on Dec. 15, 2020, provisional application No. 62/909,641, filed on Oct. 2, 2019, provisional application No. 62/820,435, filed on Mar. 19, 2019, provisional application No. 62/747,874, filed on Oct. 19, 2018.

(51) Int. Cl.
   C12N 15/10    (2006.01)
   C12P 19/34    (2006.01)
   C12Q 1/6855   (2018.01)

(52) U.S. Cl.
   CPC .......... *C12N 15/1068* (2013.01); *C12P 19/34* (2013.01); *C12Q 1/6855* (2013.01)

(58) Field of Classification Search
   CPC ... C12N 15/1068; C12P 19/34; C12Q 1/6855; C12Q 2521/501; C12Q 2525/131; C12Q 2525/301
   See application file for complete search history.

(56) References Cited

U.S. PATENT DOCUMENTS 7,435,572 B2    10/2008    Bitinaite

FOREIGN PATENT DOCUMENTS

| WO | 2013032850 A2 | 3/2013 |
|---|---|---|
| WO | 2014004393 A1 | 1/2014 |
| WO | 2015081114 A3 | 11/2015 |
| WO | 2016176325 A1 | 11/2016 |
| WO | 2020081768 A1 | 4/2020 |
| WO | 2022132198 A2 | 6/2022 |

OTHER PUBLICATIONS

Bauer et al. ("Comparative analysis of the end-joining activity of several DNA ligases." PloS one 12.12 (2017): e0190062;20 pages; published Dec. 28, 2017). (Year: 2017).*
Williams, Moleuclar Biotechnology, 23, 225-243, 2003.
Grigaite, et al., NAR, 30, 21, e123, 2002.
Pein, et al., NAR, 19, 19, 5139-5142, 1991.
Senesac, et al., BioTechniques, 22, 6, 1166-1168, 1997.
Senesac, et al., BioTechniques, 19, 6, 990-993, 1995.
Conrad, et al., NAR, 20, 19, 5127-5130, 1992.
Reuter, et al., Analytical Biochemistry, 209, 232-237, 1993.
New England Biolabs Product Specification, PaqCI, Dec. 1, 2020.
Kucera, et al., Technical Note, Jan. 1, 2018.
Gormley, et al., The Journal of Biologial Chemistry, 277, 6, 4034-4041, 2002.
Database UniProt, Database assession No. A0A2N8KYF9, Apr. 25, 2018.
Li, et al., Metabolic Engineering, 49, 13-20, 2018.
Potapov, et al., bioRxiv 322297, 2018.
Andreou, et al., PLoS One 13, 1, e0189892, 2018.
Ng, et al., J Mol. Biol., 426, 1861-1869, 2014.
Ng, et al., Protein Engineering, Design and Selection, 25, 10, 669-678, 2012.
Potapov, et al., ACS Synthetic Biology, 7, 2665-2674, 2018.
Potapov, et al., Nucleic Acids Research, 46, 13, e79, 2018.
Sarrion-Perdigones, et al., PLoS One, 6, 7, e21622, 2011.
Van Dollerweerd, et al., ACS Synthetic Biology, 7, 1018-1029, 2018.

(Continued)

*Primary Examiner* — Sahana S Kaup
(74) *Attorney, Agent, or Firm* — New England Biolabs, Inc

(57) ABSTRACT

Ordered assembly of large numbers of fragments into a single large DNA have been improved in both frequency and fidelity of the assembled product. This has been achieved by novel compositions and methods that are utilized in a computer system that integrates comprehensive ligation data from multiple sources to provide optimized synthetic overhangs or overhangs from restriction endonuclease cleavage on DNA fragments for assembly by ligation. Intragenic cut sites are avoided by the use of a novel restriction endonuclease which recognizes 7 nucleotides (bases) and cuts DNA to create 4-base overhangs with the help of a synthetic activator oligonucleotide. Variations in ligation preferences by different ligases provide extra precision in assembly reactions. The use of the improved methods are exemplified by the successful assembly from 52 fragments of a viral genome and also a 52 fragment ordered assembly of a bacteria operon.

15 Claims, 27 Drawing Sheets

Specification includes a Sequence Listing.

(56) References Cited

OTHER PUBLICATIONS

Weber, et al., PLoS One 6, 2, e16765, 2011.
Li et al. Nat. Methods Res vol. 4, 251-256 (2007).
Engler, et al. PLoS one 3, e3647 (2008).
Engler, et al. PLoS One e5553 (2009).
Quan, et al. PlosOne 4, e 6441(2009).
Zhang, et al. NAR 40, e55 (2012).
Tsuge, et al. Scientific Reports, 5, 10655 (2015).
Smolke, Nat. Biotechnol. 27: 1099-1102 (2009).
Engler, et al. Methods Mol. Biol., 729:167-181 (2011).
Marillonnet, et al. Methods Mol. Biol. 1321: 269-284 (2015).
Nilsson, et al. Nucleic Acids Res. 10:1425-1437 (1982).
Goffin, et al. Nucleic Acids Res. 15:8755-8771 (1987).
Wu, et al. Gene, 76: 245-254 (1989).
Harada, et al. Nucleic Acids Res., 21, 2287-2291 (1993).
Showalter, et al. Chem Rev. 106: 340-360 (2006).
Engler, et al. Methods Mol. Biol., 1116, 119-131 (2014).
Ellenberger, et al. Annual Review in Biochemistry, 77, 313-338 (2008).

\* cited by examiner

Ligation pool
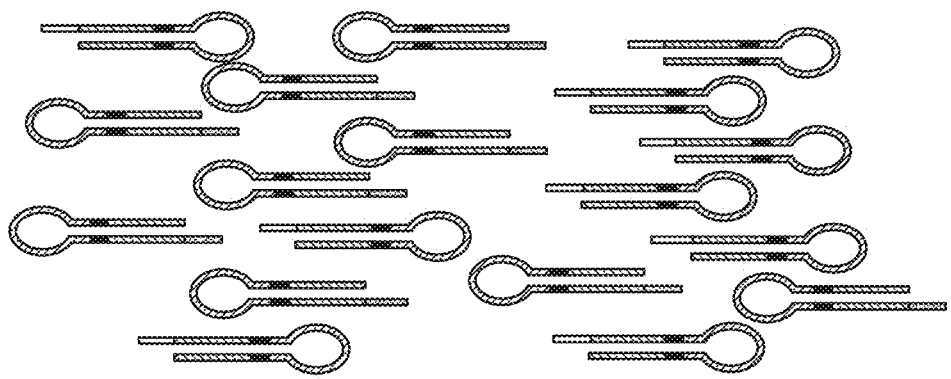
FIG. 2A
Ligation products
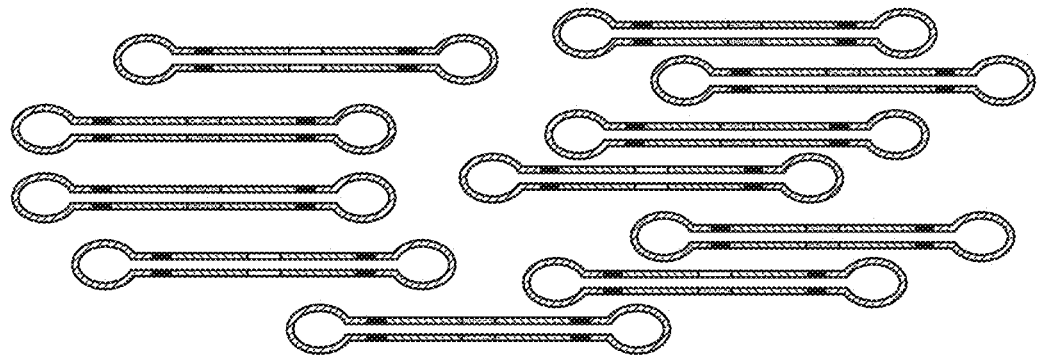
FIG. 2B
Fidelity and bias
| Overhang | Total | Correct | Mismatch | Fidelity |
|---|---|---|---|---|
| Overhang #1 | 8 | 7 | 1 | 88% |
| Overhang #2 | 4 | 3 | 1 | 75% |
FIG. 2C

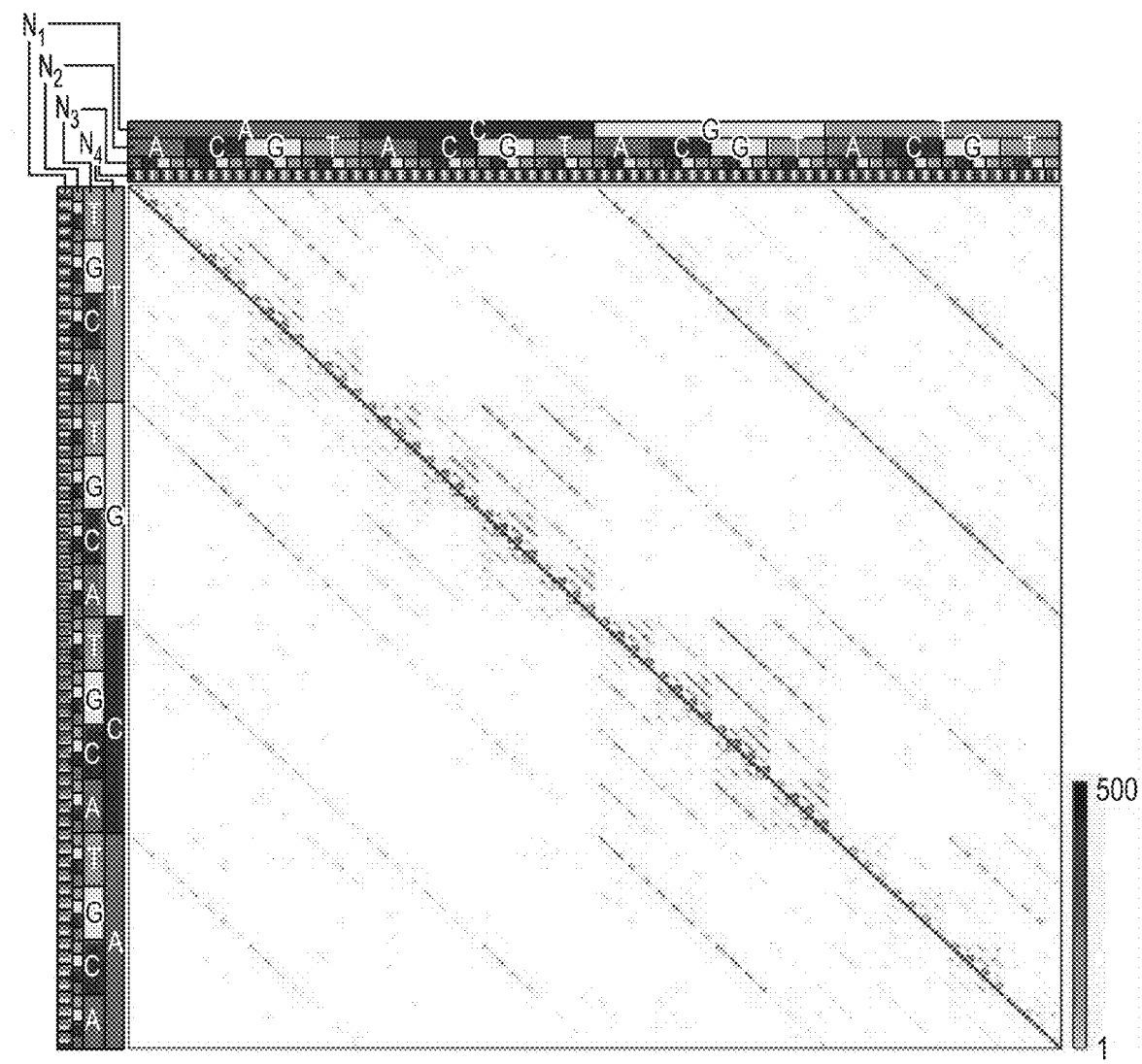
FIG. 3Ai
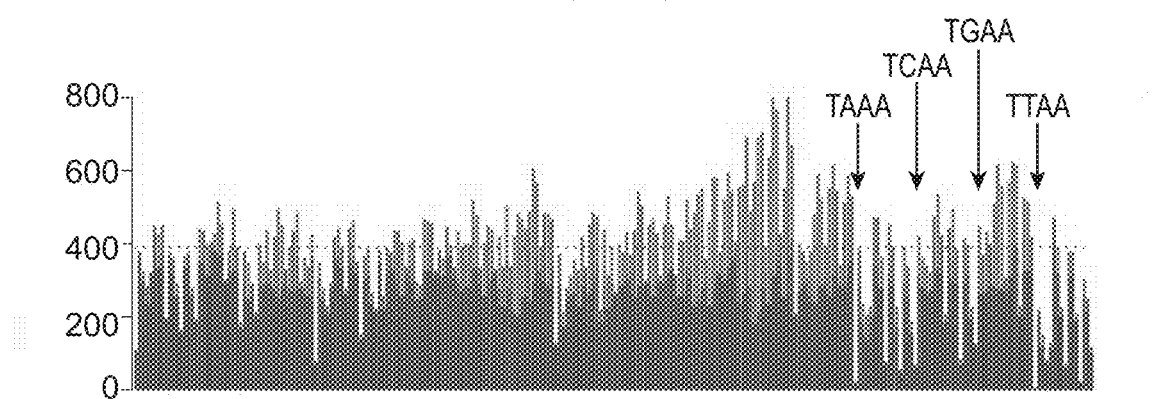
FIG. 3Aii

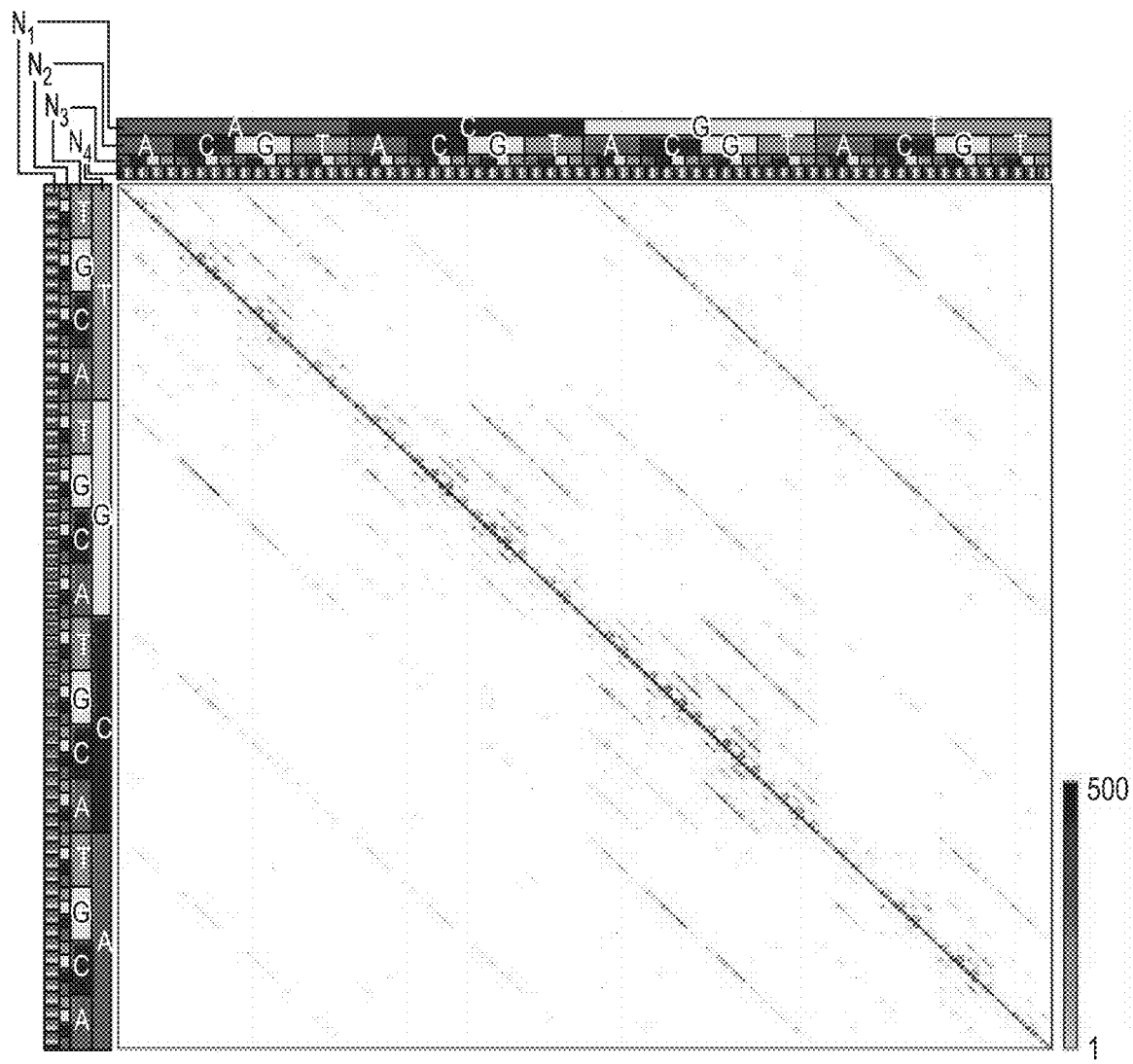
FIG. 3Bi
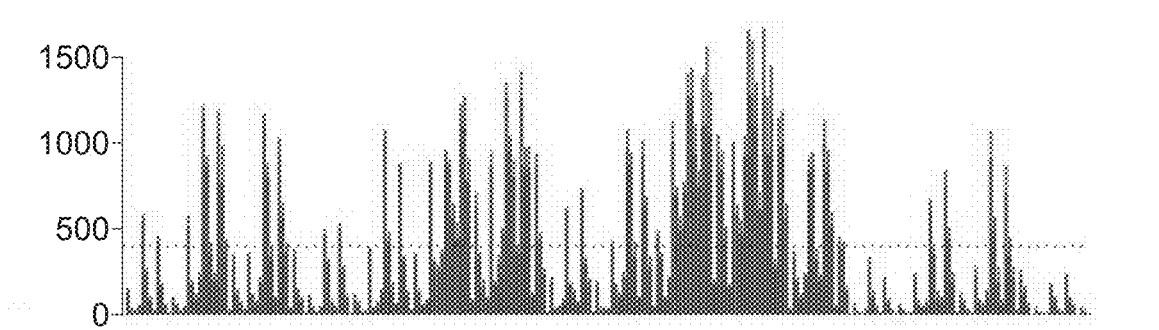
FIG. 3Bii

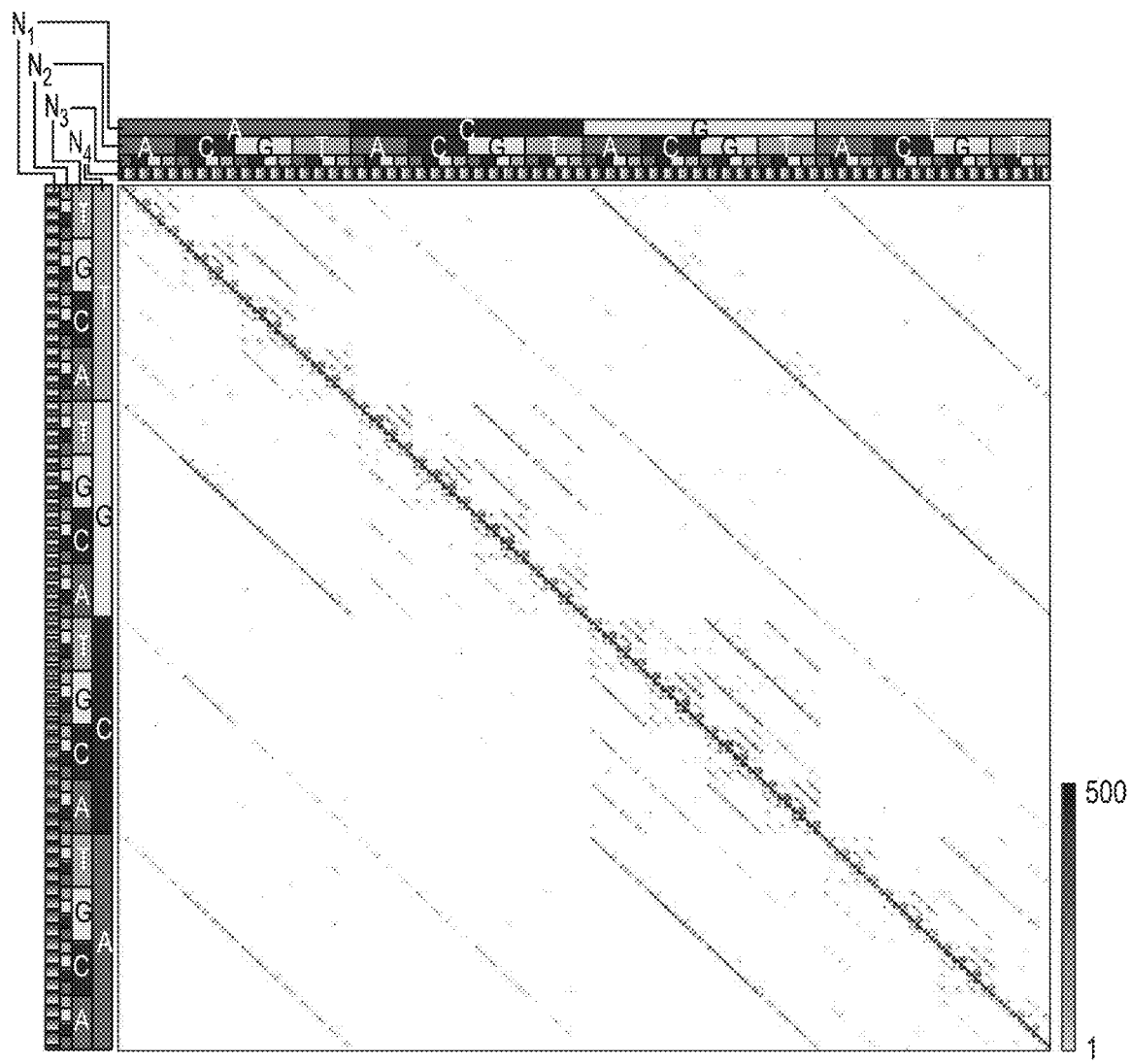
FIG. 3Ci
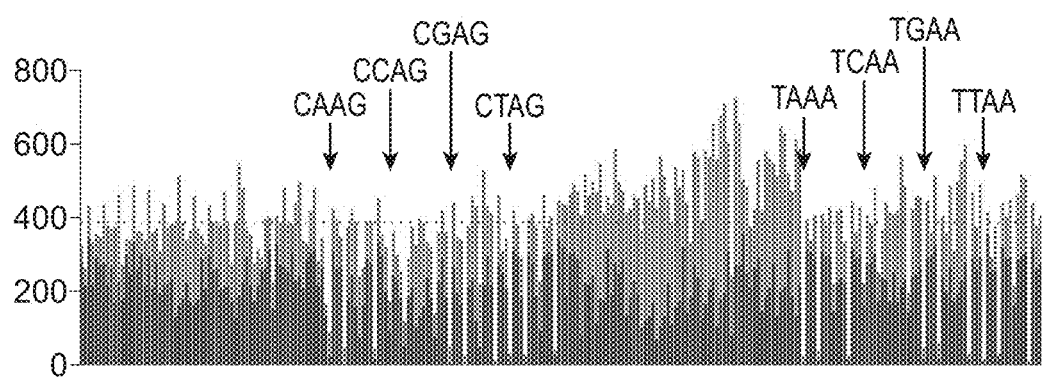
FIG. 3Cii

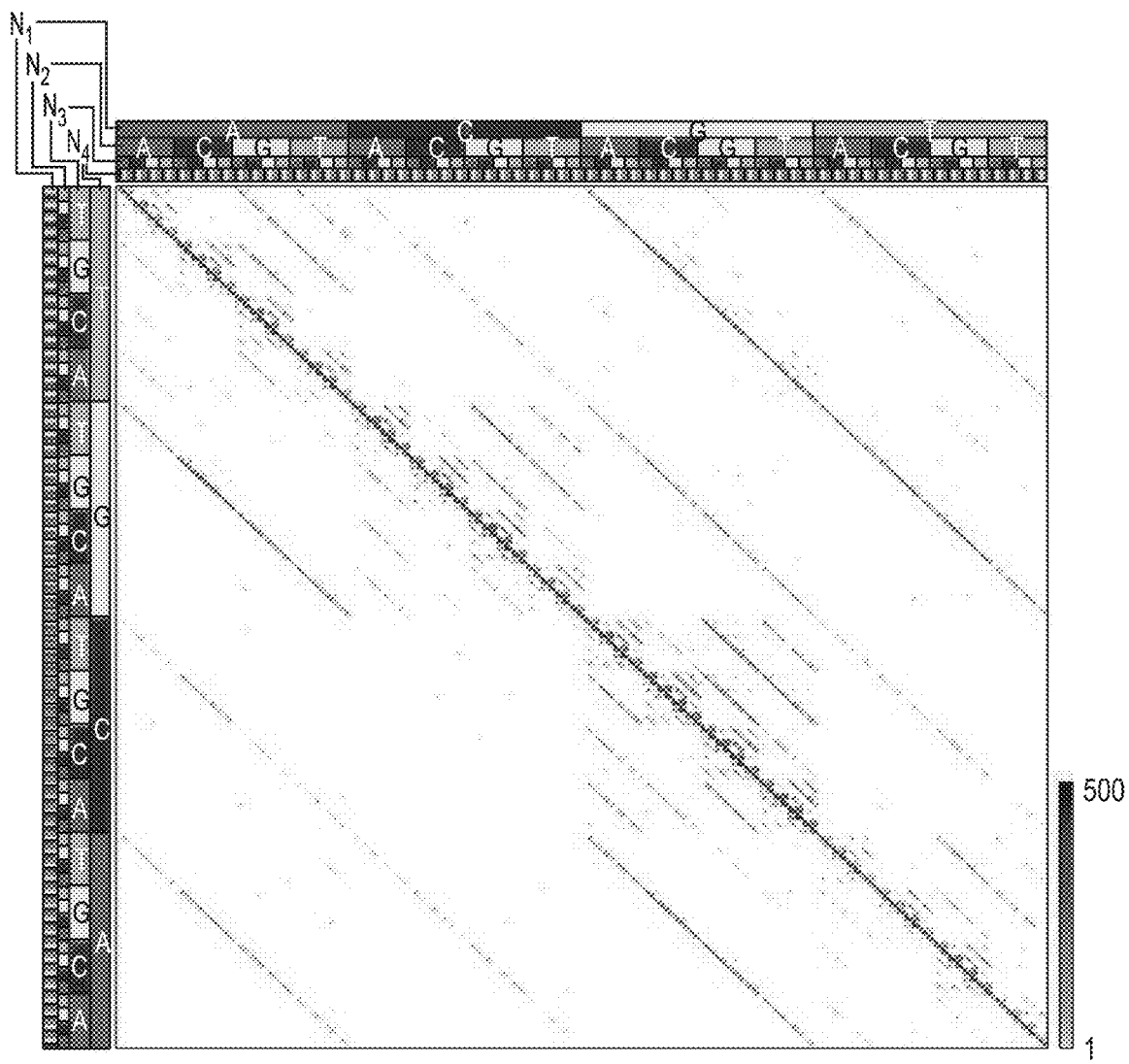
FIG. 3Di
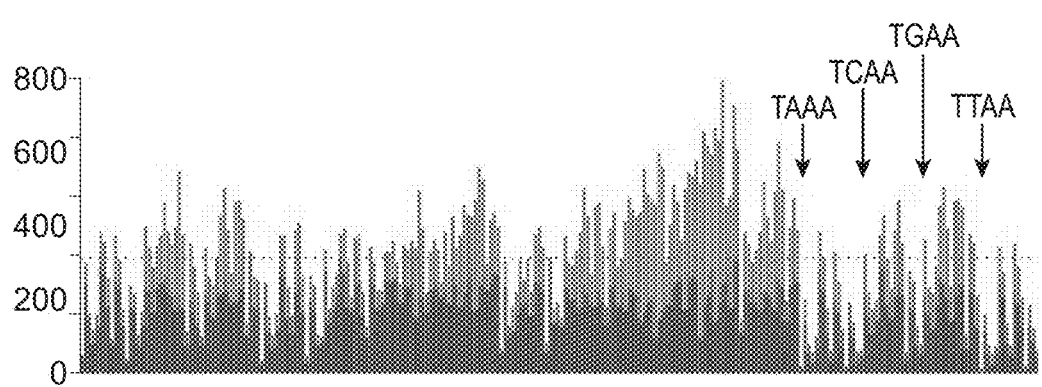
FIG. 3Dii

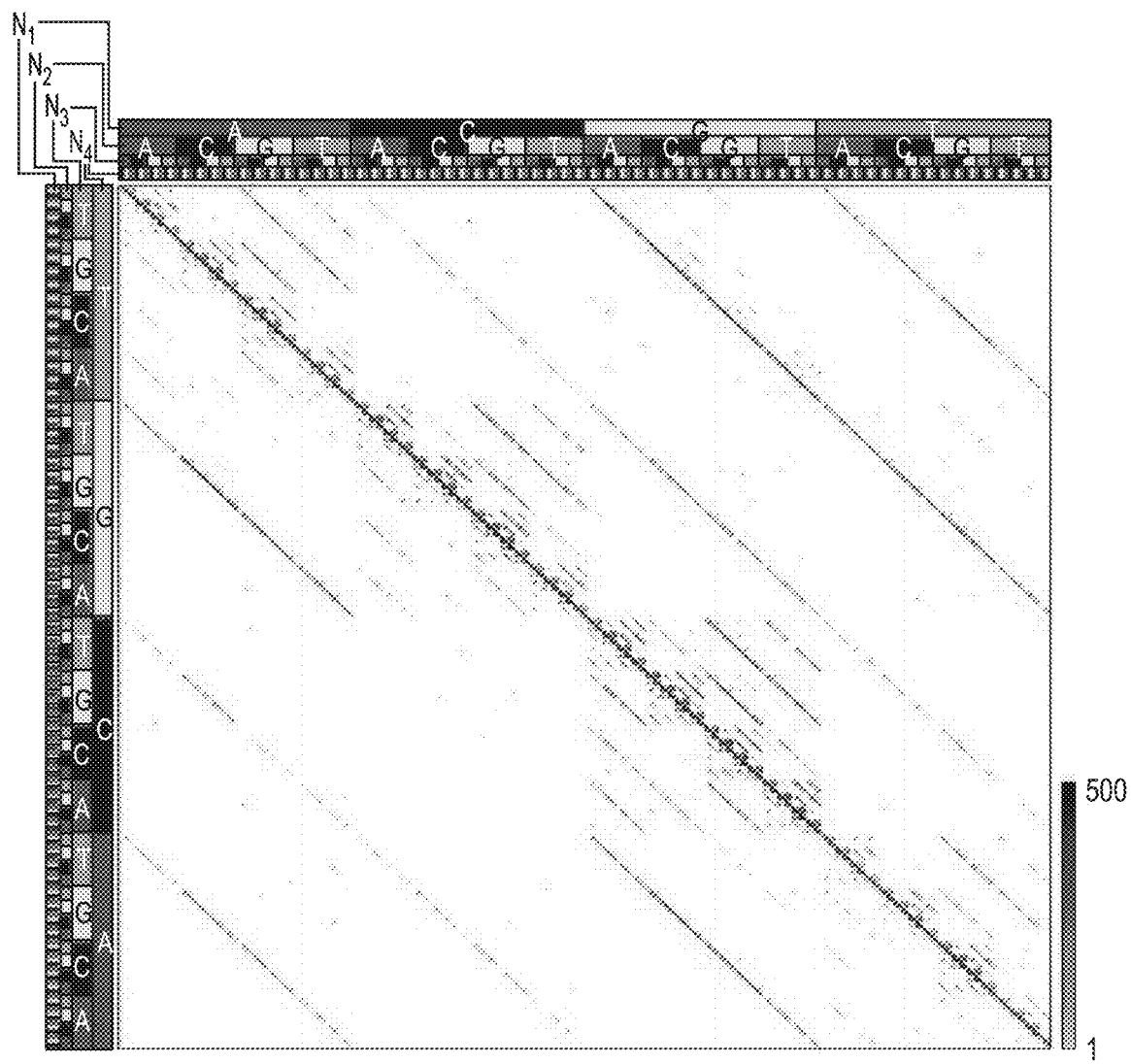
FIG. 3Ei
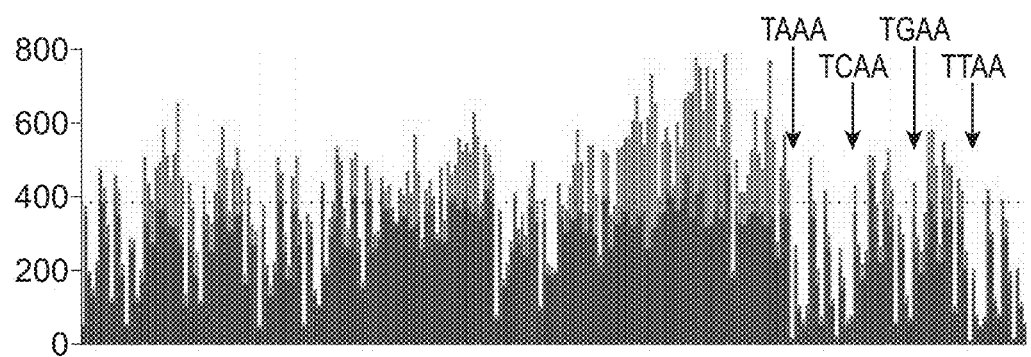
FIG. 3Eii

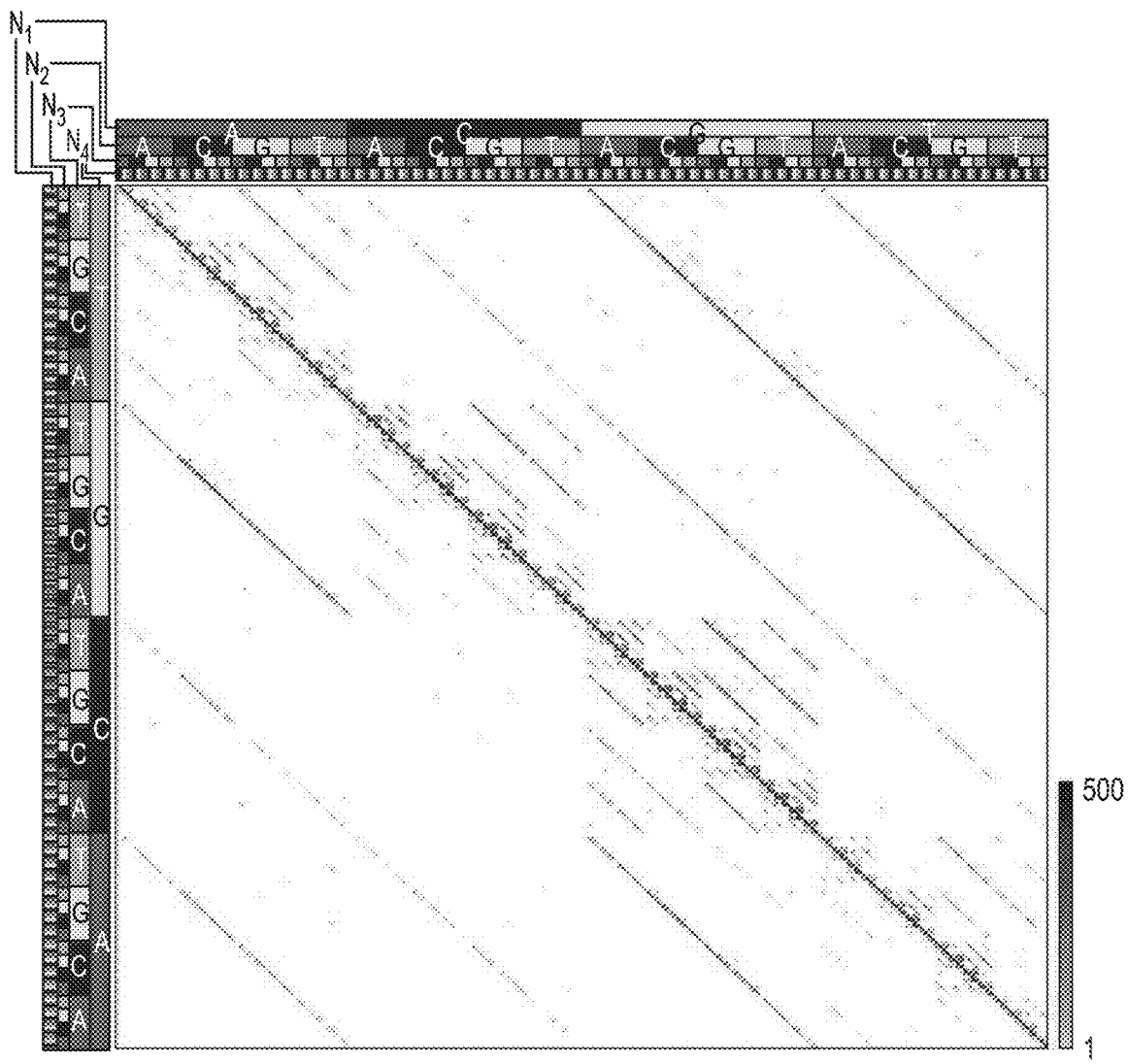
FIG. 3Fi
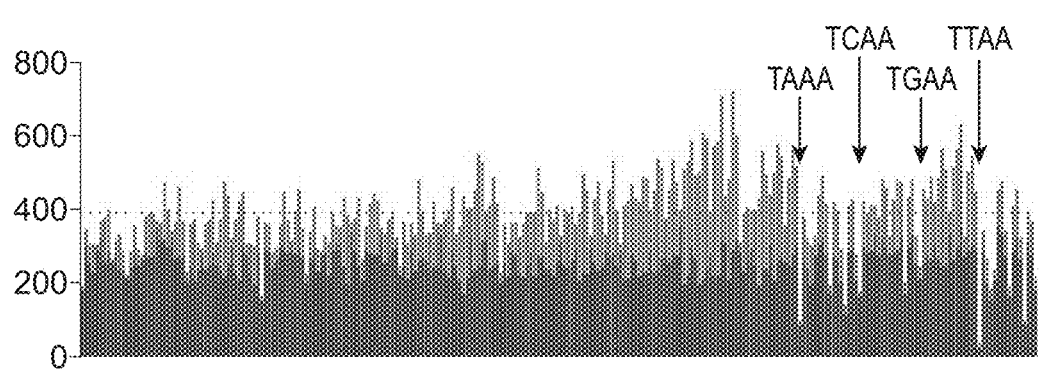
FIG. 3Fii

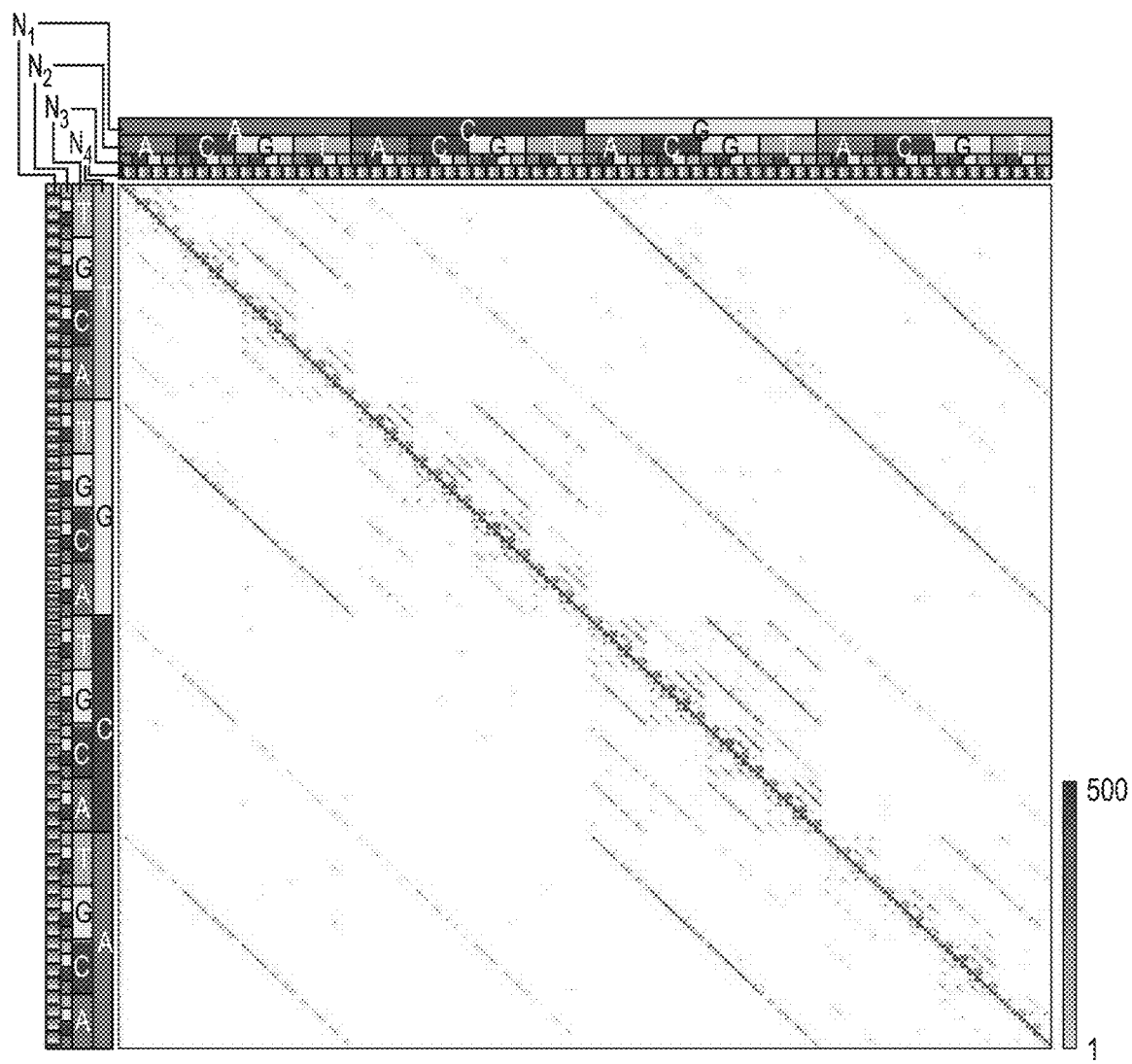
FIG. 3Gi
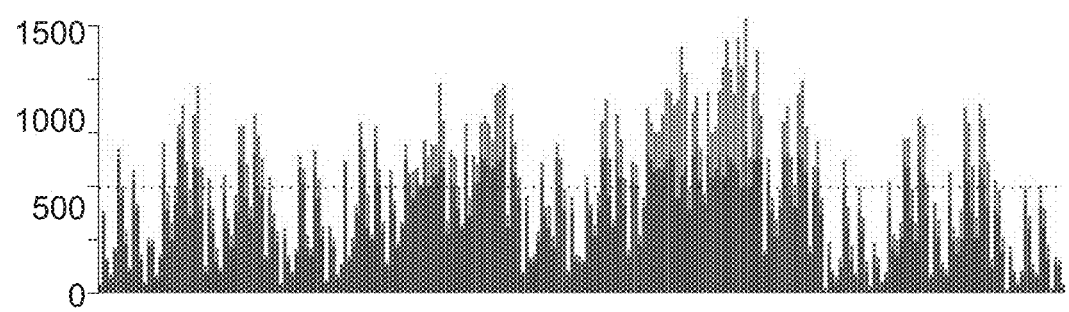
FIG. 3Gii

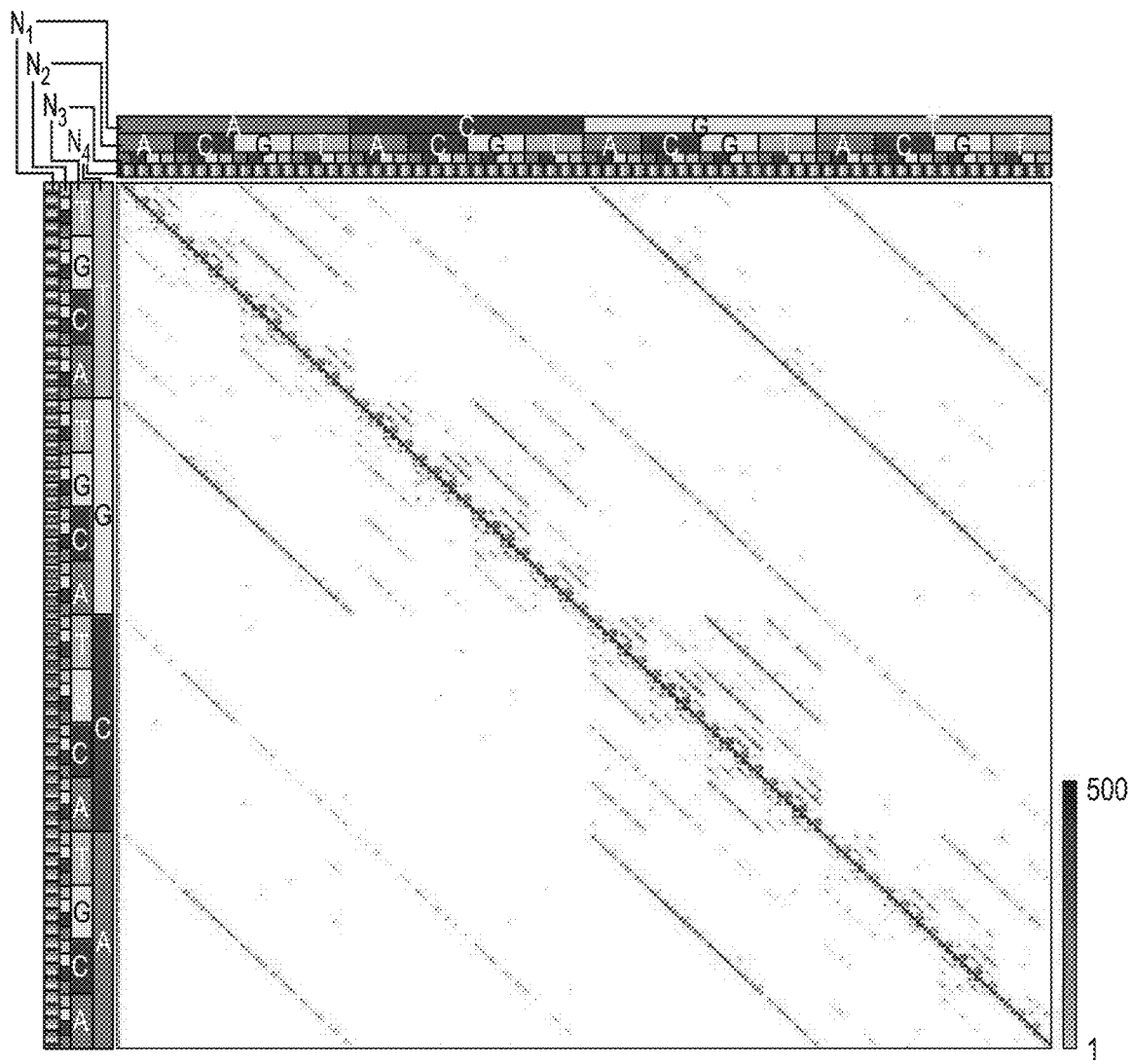
FIG. 3Hi
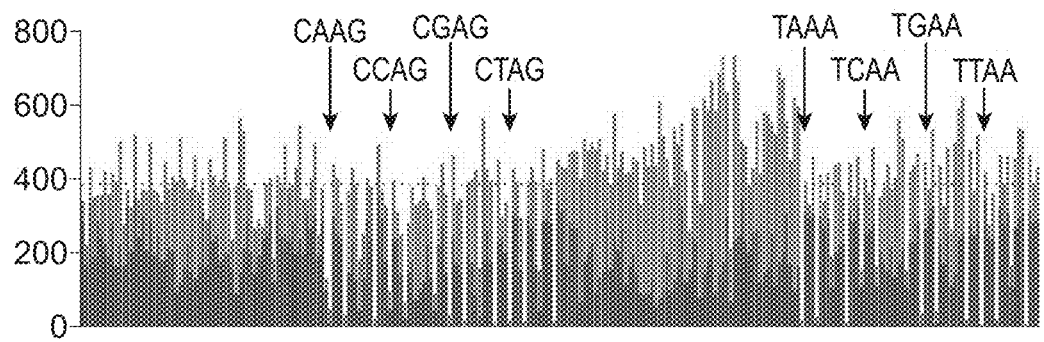
FIG. 3Hii

Ligase Fidelity Viewer (?)

Four-base overhangs (5'→3') | AAGG,ATTC,ACGT,AGTG,ATCA,TAAA,CTGA,GCTA,GGGC,GTTT (?)

Ligation conditions | T4 DNA Ligase, 25°C, 18h incubation ▽ (?)

☑ Show normalized ligation counts

[Submit]

Estimated fidelity: 50% (?)

Using a given set of overhangs in Golden Gate assembly is predicted to result in 50% of correctly lighted products.

FIG. 9B

GETSET

Submit a new job ⊙

| | | |
|---|---|---|
| Overhang length | [4-base ▼] | ←——— Overhang length (3-base, 4-base, etc.) |
| Ligation conditions | [T4 DNA Ligase, 25°C, 18h incubation (4-base substrate) ▼] | ←——— Experimental conditions |
| Number of overhangs | [10 ⊙] | ←——— Size of the overhang set |
| Required overhangs (5'→3') | [ ] | ←——— List of overhangs that must be included in the resulting set |
| Excluded overhangs (5'→3') | [AAAA,CCCC] | ←——— List of overhangs that must not be included in the resulting set |
| | [Submit] | |

Retrieve an existing job ⊙

| | | |
|---|---|---|
| Request ID | [ ] | ←——— Retrieve a previously run GETSET job |
| | [Submit] | |

Home  Help

FIG. 9C

| SPLITSET | | | Home  Help |
|---|---|---|---|
| Submit a new job | | | |
| Overhang length | 4-base | ⊙ ← Overhang length (3-base, 4-base, etc.) | |
| Ligation conditions | T4 DNA Ligase, 25°C, 18h incubation (4-base substrate) | ⊙ ← Experimental conditions | |
| Number of fragments | 5 | ⊙ ← Number of fragments to generate | |
| Nucleotide sequence | ACCATGATTACGGATTCACTGGCCGTCGTTTTACAACGTCGTGACTGGGAAAACCCTGGCGTTACCCAACTTAA TGCCTTCGCAGCACATCCCCTTTCGCCAGCTGGCTAATAGCGAAGAGGCCCGCACCGATCGCCCTTCCAAC AGTTGCGCAGCCTGAATGGCGAATGGCGCTTTGCCTGGTTTCCGGCACCAGAAGCGGTGCCGGAAAGCTGGCTG GAGTGCGATCTTCCTGAGGCCGATACTGTCGTCGTCCCCTCAAACTGGCAGATGCACGGTTACGATGCGCCCAT CTACACCAACGTAACCTATCCCATTACGGTGCGATCAATCCGCGTTGTTCCCACGGGAGAATTTTGATGGCGTTAACT CGGTTTCATCGTGGTCGCAACGGCGGCGTGGGTCGGTTAACGGCGTGGAGTCGTTGCCGTCGTCTGGAATTTGACCT GAAGGCATTTTACGCGCCGAGAAAACCGCTCGGGTGATGGTCTGCTGGGGTATGCAGCCAGTACGACTATCTGG AAGATCAGGATATGTGCGGCATGGGATCGGGTTAAGGATGCGATTTCAGCGCGTCTTGTTGCTGAGTCAGTTCAGAATGTG CGGGCGACTGCTGACAACTGTCTTACCTACGTGACTCGTGGTGAGGGTGATGCAGTGGAGCAGTCACTGCGAC CGGGCGACTTTGCGGTCACTATTCAGCGGCCGCGCATTCAGCGATCAGATTCCGCAGCTGGGTCAGCGTGGATGAGCAG CGGATGCTCGCGGCACCCGAAATTATCCCCGGAATCTGGCTGGGTACGCGCGGGTCAGCGTCAGCGATTATCCGAACCA AACCCGAACCGTGCTGGGTCTGAATACCAATATCTGGATGAAAGCTGCGATCATCTTTAAGGTCGCCGAATCCTGGA GCTGATTGAAGCAGAAGCGGGCGGTCGCCTGATTAATGCATTTTGGCGGATCAGCAGTTGCCGCGAAATGGTTCTCGTGCCGAACC GCAAGCCTGTGCTGACGTCATTGCGAGGCGTTAACCGTCACGGCATACAACCGTATGTGGCAGATACAAGGATACGGACAACC ACGATGTCGGTGGCAGCAGAAATCTGCGTGCGCGATGGAAGCCAGACAACTTATCAGCGCATTGCCAATCAGCCATGAGCCAC ATCGCCGCTGCGCAGGACGATCAGCAGCCTGCCGTGCGTGGGCGATATCGGCTTCGGCTGCGCGCAAAACCAGGCA CAGCGCGGCGATCGAATCAACAGATTGCCGGGATGTGGAACAGCGCGTCGGCGATATGAGCCAGCGGCCACCA CGGCGCTGCGCAGCCCAACCCGGCCCGGAATCAATCGGCGCCTTGGCGGGGATCGGGGCCGAGCGAGCCAAATCACGA TCGATCTACCGGATAATTATTTGCCGAATCAAATTGCCCTTACGTGGTGGGGATGAAGAACAGCAGCCCGCGACACCA CGGGCCACCCAGATGTGCAAGACGAGGCGCGCCCGCCGTGGAAGAACCGAGCCGCTTGCCGCGAAATGG TCCATCAAAAATGGCTTTCGCTACCTGGAGAGATGCGCCTGATCCTGCGAATTCCGCCCGCCGATGGG | ⊙ ← Nucleotide sequence to be split into fragments<br><br>(SEQ ID NO: 4) | |
| | Define split regions | ⊙ | |

FIG. 9D

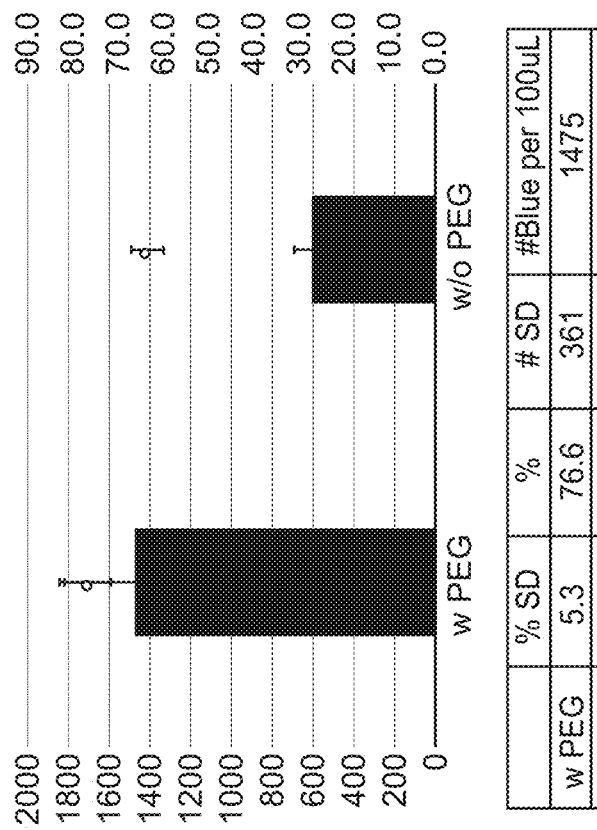
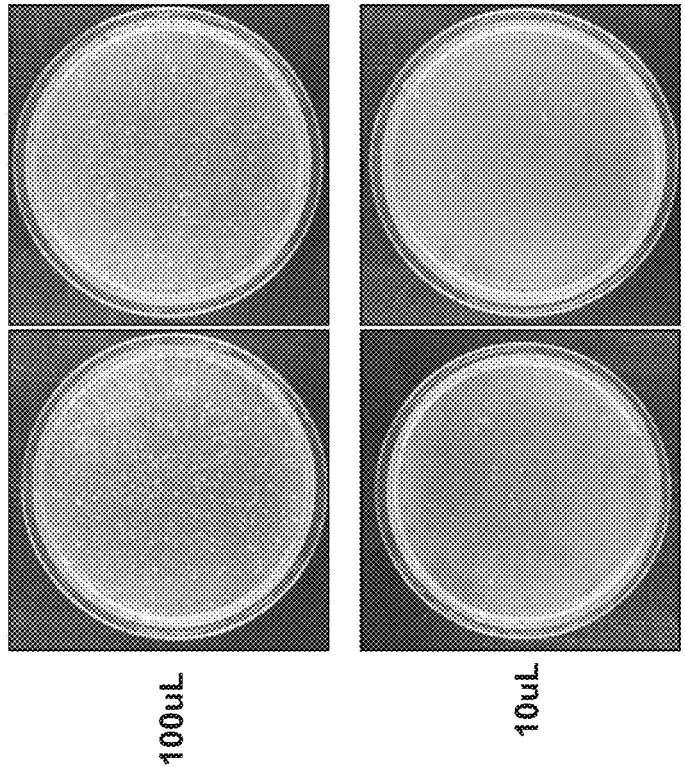
FIG. 11

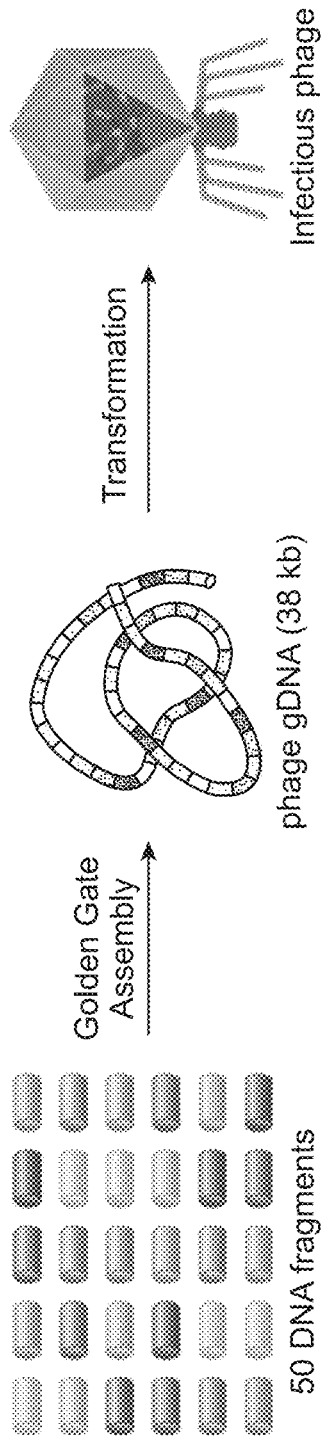

COMPOSITIONS AND METHODS FOR IMPROVED IN VITRO ASSEMBLY OF POLYNUCLEOTIDES

CROSS REFERENCE

This application is a continuation-in-part of U.S. application Ser. No. 17/644,516, filed Dec. 15, 2021, which is a continuation-in-part of U.S. application Ser. No. 17/286,066 filed Apr. 16, 2021, which is a § 371 application of International Application No. PCT/US19/56670, filed Oct. 17, 2019, which claims the benefit of priority to U.S. Provisional Application No. 62/747,874, filed Oct. 19, 2018; U.S. Provisional Application No. 62/820,435, filed Mar. 19, 2019; and U.S. Provisional Application No. 62/909,641, filed Oct. 2, 2019.

This application also claims the benefit of priority to U.S. Provisional Application No. 63/125,530, filed Dec. 15, 2020; U.S. Provisional Application No. 63/213,807, filed Jun. 23, 2021; and U.S. Provisional Application No. 63/213,859, filed Jun. 23, 2021. The contents of these applications are incorporated herein by reference in their entirety.

BACKGROUND

In vitro ordered assembly of large DNA molecules from smaller component DNA molecules is an important feature of synthetic biology. A variety of methods have been developed that include sequence and ligation-independent cloning (SLIC) (Li et al. Nat. Methods Res vol. 4, 251-256 (2007)), Golden Gate (Engler et al. PLOS one 3, e3647 (2007), Engler et al. PlosOne e5553 (2009)), circular polymerase extension cloning (CPEG) (Quan et al. PlosOne 4, e 6441 (2009), NEBuilder® (New England Biolabs, Ipswich, MA), seamless ligation cloning extract (SLICE) (Zhang et al. NAR 40, e55 (2012) and ordered gene assembly in *Bacillus subtilis* (OGAB) (Tsuge et al. Scientific Reports, 5, 10655 (2015)). These methods vary with respect to in vitro and in vivo assembly methods, homologous recombination approaches and various uses of exonucleases and ligases. The success of any assembly method is dependent on frequency and fidelity of assembled fragments, yet there has been very little systematic analysis of the criteria on which these parameters depend.

In the method referred to as Golden Gate assembly, fragments of DNA are created using restriction endonucleases that generate single strand overhangs on double stranded DNA. Ligation then occurs between overhangs on multiple different fragments to assemble a single double stranded molecule from the fragments. Methods for identifying preferred overhangs for polynucleotide fragment assembly under specified criteria for a desired number of fragments have been described in WO 2020/081768. The selection of optimized overhangs using T4 DNA ligase were collated using computer software based on extensive sequencing of assembled fragments based on varying the sequence of overhangs. Other factors including temperature and time of incubation were varied and the consequences of these were integrated into the computational analysis. The systematic analysis of fidelity and efficiency of fragment assembly and the accessibility of the resulting data in a user friendly format were shown to facilitate the faithfully assembly of large numbers of fragments in a desired order in a time efficient manner.

One aspect of Golden Gate assembly methods is the reliance on a Type IIS restriction endonuclease and a ligase. Type. IIS endonucleases that recognize 5 or 6-bases may give rise to undesirable internal cleavage sites. These can be eliminated by site directed mutagenesis or by design of assembly junction points in the recognition sequence but these elimination strategies take time and increase cost. Internal sites significantly decrease assembly efficiency, as they allow the finished construct to be susceptible to digestion by the restriction enzyme present in the assembly reaction leading to incorrect and unwanted assemblies. Hence, it is desirable to have Type IIS endonucleases that recognize 7 nucleotides for cleavage. Such enzymes would be particularly useful for assembly of multi-fragments where the assembly is complex and maximal efficiency is desirable. Furthermore, an endonuclease that is capable of cutting to completion and has no detectable star activity is preferred.

Grigaite et al. Nucleic Acid Research 2002, vol 30 e123 described AarI which is a Type IIS endonuclease with a 7 nucleotide recognition sequence. Unfortunately, this endonuclease has star activity and does not cut DNA to completion. Neither DNA or protein sequence of AarI or the buffer requirements are known so options to improve this enzyme are not available. There is a need therefore for additional improved restriction endonucleases that recognize 7 nucleotides to create 4-base overhangs and that are capable of cutting to completion.

Another aspect of Golden Gate assembly methods is its reliance on a T4 ligase. Bias in ligating various complementary overhangs was detected with T4 DNA ligase (Potapov et al. ACS Synthetic Biology, 7, 2665-2674 (2018); Nilsson et al. Nucleic Acids Res. 10:1425-1437 (1982); Goffin et al. Nucleic Acids Res. 15:8755-8771 (1987); Wu et al. Gene, 76: 245-254 (1989); Harada et al. Nucleic Acids Res., 21, 2287-2291 (1993); Showalter et al. Chem Rev. 106: 340-360 (2006); Engler et al. PlosOne e5553 (2009); Engler et al. Methods Mol. Biol., 729:167-181 (2011); Engler et al. Methods Mol. Biol., 1116, 119-131 (2014)). This bias accompanied by less than perfect fidelity resulting from ligation of mismatched sequences in the ligated DNA becomes a significant issue for large numbers of fragments in an ordered assembly reaction. Universal rules for selecting an overhang set have not been identified for large fragment assembly. Instead, assembly design may be achieved best for each individual case using a computer tool that can compare annealed overhang ligation data to provide optimized sets of overhangs or evaluate existing sets of overhangs. As uses for assembly of large sets of fragments increase, so does the need for refining the available computer tools for data optimized assembly design.

SUMMARY

A synthetic self-complementary oligonucleotide is provided that is characterized by a double-stranded region and a single strand loop, wherein the double-stranded region contains a recognition sequence for PaqCI® (New England Biolabs, Inc.), has unligatable 3' and 5' ends and cannot be cleaved by PaqCI. PaqCI is defined herein as including variants that have no more than 10% amino acid modifications compared to the wild type and retain DNA recognition specificities and cleavage properties. The oligonucleotide may be further defined by any one or more of the following features: the double-stranded region having a length of 10-50 base pairs; the length of the oligonucleotide less than 110 nucleotides; the 3' end of the oligonucleotide not a 3' hydroxyl; the 5' end of the oligonucleotide is not a 5' phosphate and/or the recognition sequence being CACCTGC; and occurring only once in the oligonucleotide.

A reaction mixture is provided that includes, a synthetic self-complementary oligonucleotide described above and a PaqCI restriction endonuclease or a variant thereof having an amino acid sequence that has at least 90% amino acid sequence identity with SEQ ID NO:1, where PaqCI is defined herein as including variants that have no more than 10% amino acid modifications compared to the wild type and retain DNA recognition specificities and cleavage properties. Features of the reaction mixture may include one or more of the following features: the ratio of PaqCI to the synthetic self-complementary oligonucleotide is in the range of 1 unit PaqCI: 0.75 pmole to 9 pmole oligonucleotide; includes a double-stranded DNA substrate and/or a ligase; the DNA substrate contains one or more recognition sequences for PaqCI and can be cleaved by PaqCI to produce a 4-base overhang; the recognition sequence in the DNA substrate is CACCTGC; the DNA ligase selected from the group consisting of T4 DNA ligase, T3DNA ligase, T7 DNA ligase, PBCV-1 DNA ligase and hLig3; the ratio of the PaqCI to ligase is 2.5-20 PaqCI Units to 200-800 ligase units; the reaction mixture includes a plurality of plasmid or PCR products that contain fragments that are each flanked by binding sites for PaqCI and wherein cleavage of the plasmid or PCR products by PaqCI or variant thereof produces fragments with different 4-base overhangs.

A method is provided that includes the following steps: (a) obtaining a reaction mixture comprising: (i) a synthetic oligonucleotide as described above; (ii) PaqCI; (iii) a ligase; and (iv) a library of DNA substrates each having at least one PaqCI recognition sequence and a cleavage site; (b) cleaving the library of DNA substrates with PaqCI to generate fragments that have 4-base overhangs; and (c) ligating complementary 4-base overhangs together to produce an ordered assembly of the fragments.

The method may include the following features: the DNA substrates in the library are selected from one or more of the group consisting of: a PCR products, plasmids, genomes or chromosomes; step (c) may further include ligating the ordered assembly into a destination vector or viral genome; the destination vector is a plasmid, or a chromosome; the ligase may be selected from the group consisting of: T4 DNA ligase, T3 DNA ligase, T7 DNA ligase, PBCV-1 and human ligase 3; there are 10-100 DNA substrates having unique sequences and the ordered assembly comprises 10-100 fragments that are ligated together in step (c); at least 20 DNA substrates having unique sequences are included in the reaction mixture and the ordered assembly comprises at least 20 fragments that are ligated together in step (c); and the reaction mixture may additionally include a DNA repair enzyme, for example EndoMS, a deadenylase, for example, yeast deadenylase, and/or a crowding agent for example polyethylene glycol (PEG) having a molecular weight in the range of 600-8000.

The method in step (a) may include: identifying a set of 4-base overhangs for the reaction mix using a computer tool wherein: (i) the computer tool generates from a data set; an optimized fidelity and/or frequency score for a set of 4-base overhangs for the library of DNA wherein the optimized fidelity and/or frequency score is derived from data on annealing of complementary sequences; and data from ligase activity for different 4-base overhangs; and/or (ii) the computer tool provides break points in an in silico sequence to generate fragment sequences for joining in an ordered assembly via optimized 4-base overhangs.

A kit is provided that contains a synthetic self-complementary oligonucleotide as described above and PaqCI that encompasses variants as defined above. Additional components of the kit may include one or more of the following: a ligase; a cofactor selected from the group consisting of a repair enzyme a mismatch specific endonuclease such as EndoMS, deadenylase and a crowding agent such as polyethylene glycol (PEG) and has a molecular weight in the range of 600-8000; and instructions for synthesizing a large DNA from component fragments having 4-base overhangs. The reagents in the kit may be combined or in two or more containers. In one embodiment, at least one of the oligonucleotides, ligase and PaqCI variants, are freeze dried or immobilized on a solid substrate such as a two dimensional or a three dimensional surface.

A computer implemented method is provided for selecting a set of overhangs for an ordered assembly reaction performed under selected ligation conditions, that includes (a) receiving: (i) a desired number of overhangs for an assembly reaction and (ii) a length of the overhangs; (b) selecting a set of overhangs from an overhang table, wherein the selected set of overhangs has the desired number of overhangs received in (i) and the length of overhangs received in (ii); (c) selecting a ligase from a plurality of different ligases for ligating the overhangs with reduced bias; (d) for each individual overhang in the set, calculating a ligation fidelity score for the selected ligase, wherein the ligation fidelity score of each individual overhang represents the frequency at which the individual overhang and its complement independently ligate to a perfectly complementary overhang relative to all overhangs in the set and their complements; (e) calculating an overall ligation fidelity score for the set of overhangs based on the calculated ligation fidelity scores for each of the individual overhangs, as output in step (d); (f) iterating (b)-(e) until a plurality of overall ligation fidelity scores have been calculated, each for a different set of overhangs; and (g) providing the set of overhangs that has a suitable overall ligation fidelity score for a selected ligase.

One or more features of the computer implemented method include: that each of the individual overhangs in the set of overhangs selected in (b) is unique within the set, and is not complementary to another overhang in the set, and is not palindromic; calculating the ligation fidelity score in (c) further includes: consulting the ligation frequency table and bias table for different ligases comprising individual experimentally-defined measurements of the number of ligation events and/or mismatch events; calculating the number of ligation events and/or mismatch events that occur between each individual overhang and its complement relative to the total number of ligation events that occur between the individual overhang and all of the overhangs in the set and their complements and the complement of the individual overhang and all of the overhangs in the set and their complements; wherein the set of overhangs correspond to the individual overhangs on each end of a plurality of double stranded polynucleotide fragments for ordered assembly into a target polynucleotide, wherein the individual overhangs are single stranded sequences consisting of 2-5 nucleotides such that each end of each polynucleotide fragment has a different overhang and wherein the ordering of fragment assembly is a product of annealing of an overhang at one end of a polynucleotide to a complementary overhang on one end of an adjacent polynucleotide.

Another feature of the method may include: in (a) receiving (iv) a nucleotide sequence of an assembly; and (v) a set of intervals in which the nucleotide sequence of (iv) can be enzymatically cleaved and identifying a non-redundant set of sub-sequences in the intervals that are the same length as the overhang length input in (ii), where each sub-sequence has an overhang; and the method further comprises: (h)

storing the non-redundant set of sub-sequences having the set of overhangs with a suitable overall fidelity score.

Another feature may include defining each interval of (v) by beginning and end coordinates in the nucleotide sequence of the assembly.

Another feature may include: in (e) iterating (b)-(d) at least 1000 times.

Another feature may include: in (a) receiving the selected experimental conditions for enzymatic cleavage and ligation for ordered assembly of the polynucleotide fragments.

Another feature may include: receiving the selected experimental conditions for providing the set of overhangs in (g) having a suitable fidelity and/or frequency score for annealing and for ligation with a selected ligase.

Another feature may include causing the computer implemented method as described above to be executed and receiving an output containing the set of overhangs as identified in (g), and/or if (iv) and (v) are input, then receiving sequences for a set of polynucleotide fragments for ordered assembly, where the ends of the fragments are defined by the overhangs identified in (g).

The computer implemented method may include obtaining sequences for a set of polynucleotide fragments having the identified non-redundant set of sub-sequences in the intervals that can be enzymatically cleaved to produce the identified overhangs. Another feature of the method may include establishing that the selected experimental conditions and the computer-generated set of overhangs are suitable for ordered assembly of a selected set of polynucleotide fragments with an effective amount of fidelity and frequency of complementary annealing and ligase dependent ligation for the number of fragments in the set. The experimental conditions (ligation conditions) may include selecting a DNA ligase, having a suitable fidelity and frequency score, for ligating the set of polynucleotide fragments containing 4-base overhangs where for example, the ligase is a wild type T4 DNA ligase, or a variant thereof selected from a thermostable T4 DNA ligase and a salt tolerant T4 DNA ligase wherein, the ligase is selected from the group consisting of: T4 DNA ligase, T7 DNA ligase, hLig3 DNA ligase, T3 DNA ligase, PBCV-1 DNA ligase, a temperature stable variant of any of T4 DNA ligase, T7 DNA ligase, hLig3 DNA ligase, T3 DNA ligase, or PBCV-1 DNA ligase and a high salt stable variant of any of T4 DNA ligase, T7 DNA ligase, hLig3 DNA ligase, T3 DNA ligase, PBCV-1 DNA ligase; and/or selecting a Type IIS restriction endonuclease, having a characteristic DNA recognition sequence, for enzymatic cleavage of the set of polynucleotide fragments containing the recognition sequence so that each polynucleotide fragment so cleaved contains an overhang sequence from the set of overhang sequences, where for example, the Type IIS restriction endonuclease has a 7-base recognition sequence for example, PaqCI.

Other examples of the selected experimental conditions for ordered assembly of a target polynucleotide from the set of polynucleotide fragments include ligation conditions comprising one or more of, a salt concentration, a DNA repair enzyme, a temperature range and/or thermocycling conditions for cleavage and ligation. For example, the salt concentration may be in the range of 50 mM-150 mM salt, the DNA repair enzyme is EndoMS or T7 Endo I, the temperature range is 37° C.-50° C. and the thermocycling conditions are selected from drop-down, touch-down and touch-up temperature cycling.

In additional embodiments of the method, additional features may include: the nucleotide sequence of an assembly selected from a virus genome, a prokaryotic genome, an operon and a metabolic pathway; and wherein the number of polynucleotide fragments to produce an assembly is in the range of 2-100 fragments.

A computer-readable medium is provided for performing the methods described by suitable software.

A method is provided for synthesizing a target polynucleotide that includes: (a) obtaining a set of overhangs that have a suitable overall fidelity score under a set of experimental conditions including selection of a ligase using the computer implemented method described above; wherein the computer instructs an automated instrument or a user to assemble, under the set of selected experimental conditions, determined at least in part by the user, a set of polynucleotide fragments having sequences optionally determined by the computer or by the user, that have been enzymatically obtained or chemically synthesized; (b) permitting the optionally automated ordered assembly of a target polynucleotide by combining a ligase, restriction endonuclease and the polynucleotide fragments under the selected experimental conditions within the instrument or in a reaction tube; and (c) optionally introducing the target polynucleotide into: (i) a bacterial cell; or (ii) into an in vitro system, for expression of the gene or genes.

This method enables assembly of the target polynucleotide by repeating steps (a) and (b) such that in the first round, the polynucleotide fragments are less than 1000 bases in length so that the assembled fragments form an interim target polynucleotide and the interim target polynucleotides form the polynucleotide fragments for the next round of ordered assembly to form the final target polynucleotide. The set of polynucleotide fragments in (a) is 2-100 fragments more specifically 20-100 fragments or at least 20 fragments. The method may include performing multiplex amplification of the set of polynucleotide fragments prior to (b). In the method, the target polynucleotide may be a DNA that may be transcribed to form a target RNA. The target polynucleotide may be a DNA and wherein the DNA is expressed in cells to produce one or more proteins. For example, the target proteins may be part or all of a metabolic pathway, a viral genome or an immune cell gene.

A method of performing an ordered DNA assembly from 20-100 DNA fragments to create a large DNA, is provided that has the following steps that can be performed in any order: (a) obtaining instructions from a computer design tool for an optimized set of 4-base overhang sequences for joining 20-100 fragments in an ordered assembly reaction, wherein the computer design tool computes the optimal set of overhangs from one or more sets of data, wherein each set of data results from frequency and fidelity analysis of individual ligase preferences for all combinations of four base overhangs; and (b) obtaining 20-100 fragments having the optimized set of 4-base overhangs for ligation with a selected ligase in an ordered assembly reaction to create a large DNA.

The method may include; adding a Type IIS restriction endonuclease recognition sequence to the 20-100 fragments using a polymerase chain reaction (PCR) or inserting the 20-100 fragments into 20-100 plasmids having a Type IIS restriction endonuclease recognition sequence at the insertion site at each end of the fragment or synthesizing the 20-100 fragments with the optimized 4-base overhangs.

A Type IIS restriction endonuclease may be selected that has a recognition sequence of 5'CACCTGC3' and the cleavage site to create the optimized set of 4-base overhangs is 5'CACCTGC (N4)3' (SEQ ID NO:2) and 3'GTGGACG(N8) 5' (SEQ ID NO:3). For example, the restriction endonuclease is PaqCI. In other features, the ligase may be selected from one or more of T4 DNA ligase, T7 DNA ligase, hLig3 DNA ligase, T3 DNA ligase, or PBCV-1 DNA ligase.

A method for high-through put assembly of customized T-cells is provided that includes the steps of: (a) identifying a surface antigen on a tumor cell from a patient, wherein the protein is specific for the tumor cell; (b) collecting T-cells from the patient; (c) causing an ordered assembly of DNA fragments with 4-base overhangs to form a large DNA encoding a chimeric antigen receptor that is tumor antigen specific; and (d) introducing the large DNA into the genome of the T-cell that has been cleaved by site direct CrispR.

The large DNA in (d) may be the product of ordered assembly of a plurality of DNA fragments that are conserved and a plurality of variable DNA fragment sequences such that at least the conserved DNA fragments are individually stored in plasmids in bacterial cells for high throughput assembly of the customized T-cells.

A method is provided for creating viral genomes with mutations that include: (a) generating a plurality of fragments for ordered assembly into a viral genome; (b) selecting four base overhangs that permit ligation of multiple mismatches by a ligase; and (c) testing the product viral genome for antibiotic activity or as a substrate for vaccine production. An example of this method is where the ligase is a relatively low fidelity ligase for example, hLig3. The above methods may be accomplished in high throughput workflows using microfluidic devices or robotic devices to handle multiple samples in repetitive cycles of joining fragments to create any size of DNA from small fragments of DNA.

PaqCI from *Paucibacter aquatile* together with a synthetic activator oligonucleotide (also referred to as "activator" or "oligonucleotide") and T4 DNA ligase provided greatly enhanced efficiency of colony formation and fidelity of sequences in the assembled large DNA from 24 fragments compared with AarI.

Figure 1A:
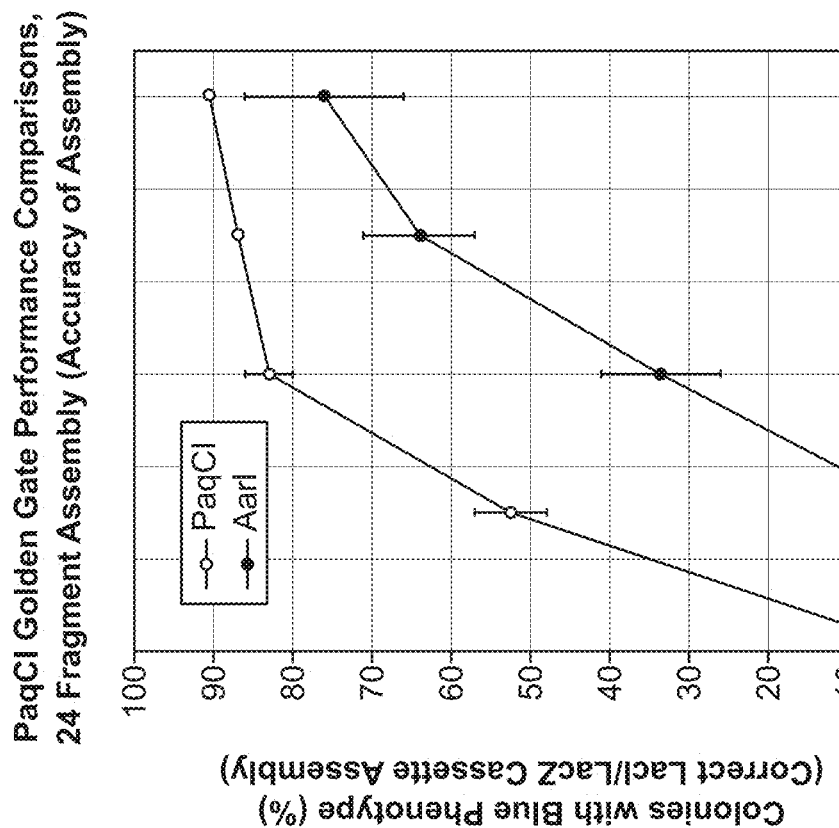
FIG. 1A-1B shows the PaqCI performance comparison for 24 fragment assembly (efficiency) as determined by the number of colonies with blue phenotype indicating correct LacI/lLacZ assembly per 50 ul outgrowth (½0 total outgrowth).

FIG. 1A: PaqCI provided more than 10 fold greater number of colonies having correct assembly than observed for AarI over 30 cycles.

Figure 1B:
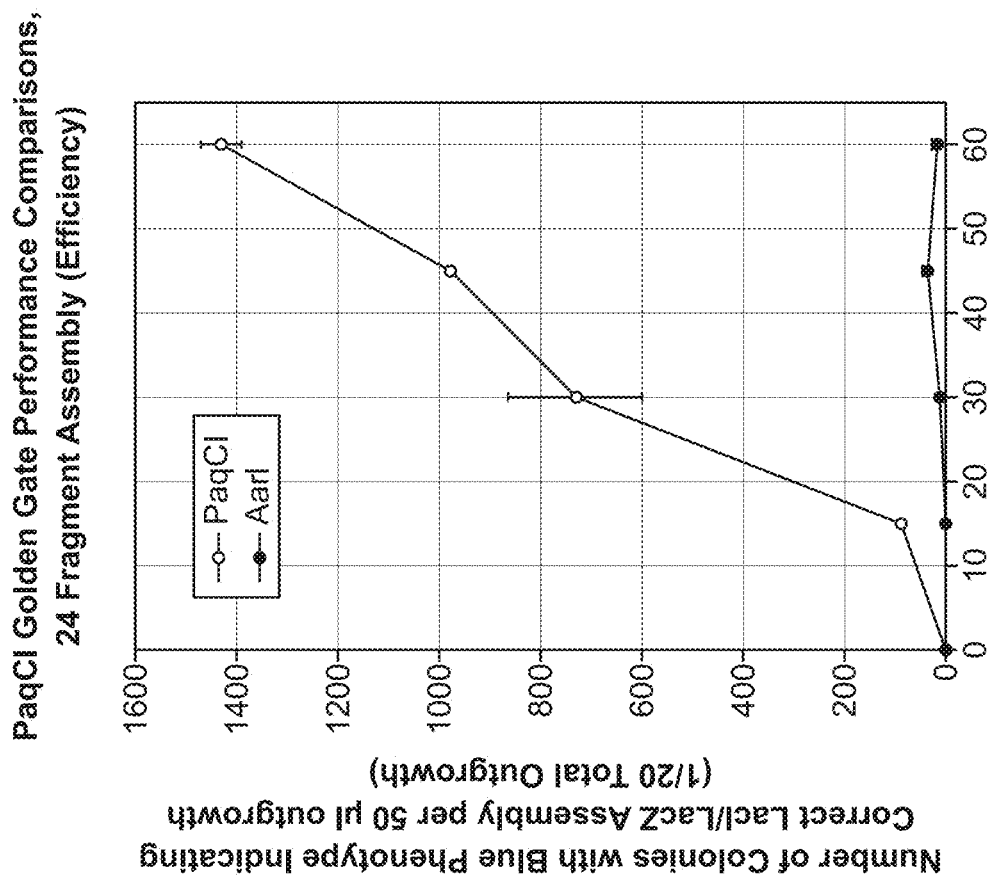

FIG. 1B: PaqCI provided at least 15% greater fidelity than AarI in 30 cycles (5 minutes 37° C. to 5 minutes 16° C.) for a 24 fragment assembly reaction of a LacI/LacZ cassette as determined by blue colonies.

Figure 1C:
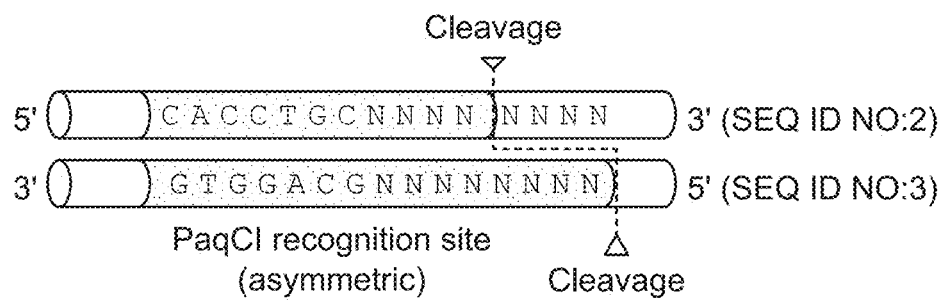

FIG. 1C shows the recognition sequence and asymmetric cut site for PaqCI to produce a 4-base overhang.

Figure 1D:
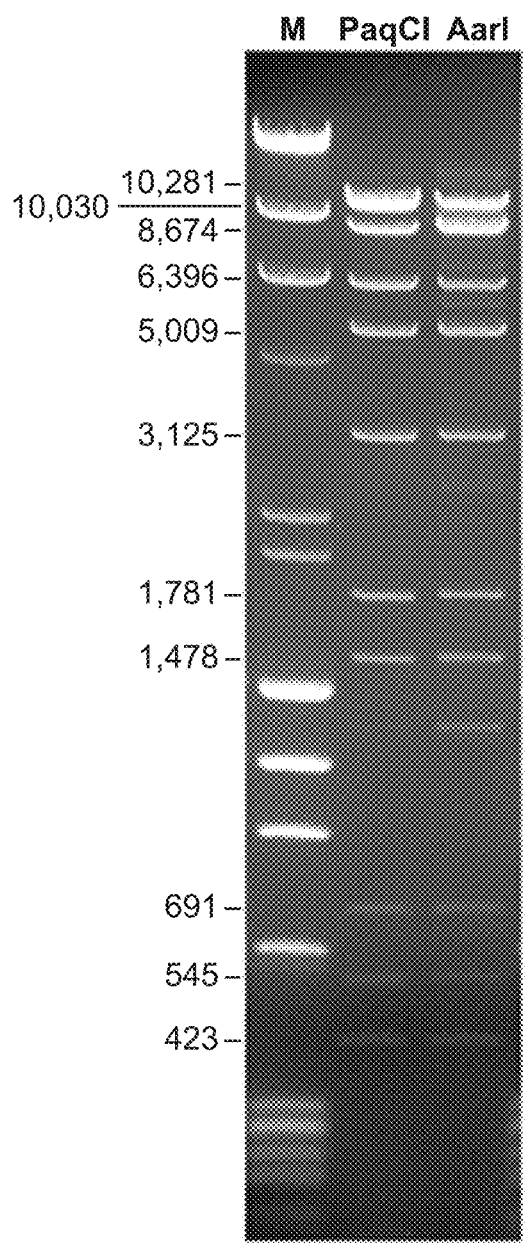

FIG. 1D shows that unlike AarI, PaqCI cuts to completion and does not exhibit star activity. 1 μg Lambda DNA was digested with 8 units of either PaqCI (New England Biolabs, Ipswich, MA) or AarI (Thermo Fisher Scientific, Waltham, MA) following manufacturer's recommended protocols. Digestions were analyzed on a 1% agarose gel.

FIG. 2A-2C provides a schematic of an assay to determine how fragments with different sequence overhangs are affected by ligation bias and the fidelity of the ligation event.

FIG. 2A: Libraries containing randomized four base overhangs were synthesized. Sample randomized overhang pairs are schematically represented.

FIG. 2B: Ligation substrates are ligated with a specified DNA ligase and correct (same overhang shading) and mismatch containing (different overhang shading) products are formed. The correct or mismatch was analyzed using SMRT® sequencing (Pacific Biosciences, Menlo Park, CA).

FIG. 2C: Ligation fidelity is defined as the fraction of correct ligations. Ligation bias is detected by differences in total numbers of ligation products formed for each overhang.

FIGS. 3Ai/3Aii-3Hi/3Hii) shows significant variation between different ligases with respect to sequence preferences with observed variation between correct ligations and mismatch ligations. The number and type of 4-base sequences that are underrepresented also varies between ligases. This reveals bias of at least 2 types-bias for or against a ligation event for certain 4-base overhangs and bias for ligation of mismatches and against perfect matches or vice versa.

3Ai-3Hi shows a ligation frequency heat map matrix of all ligation events (log-scaled). Overhangs are listed alphabetically left to right (AAAA, AAAC, AAAG . . . TTTG, TTTT) and bottom to top such that the Watson-Crick pairings are shown on the diagonal. The matrix shows ligation frequency for each of 256×4-base overhangs on the X axis against 256×4-base overhangs on the Y axis. Each base in the 4-base overhang is color coded where T is red, C is blue, G is yellow and A is green (colors represented by different shades of grey). 100 nM of the multiplexed four-base overhang substrates were ligated during an incubation for 1 hour at 25° C., with 1.75 μM T4 DNA ligase in standard ligation buffer and sequenced by SMRT sequencing. Overhang sequences were normalized to 100,000 ligation events.

3Ai-3Hii shows a stacked bar plot of frequency of ligation products containing each overhang, corresponding to each column in the heat map in (A). Fully Watson-Crick paired ligation results are indicated in blue, and ligation products containing one or more mismatches are in orange (represented by two shades of grey) A. Certain overhangs are under-represented as indicated by arrows FIGS. 3Ai and 3Aii is T4 DNA ligase. TAAA, TCAA, TGAA and TTAA are underrepresented.

FIGS. 3Bi and 3Bii is T7 ligase. Many 4-base overhangs are underrepresented.

FIGS. 3Ci and 3Cii is Human ligase 3 (hLig3). CAAG, CCAG, CGAG, CTAG, TAAA, TCAA, TGAA and TTAA are underrepresented.

FIGS. 3Di and 3Dii is T3 ligase. TAAA, TCAA, TGAA and TTAA are underrepresented.

FIGS. 3Ei and 3Fii is PBVC-1 ligase. TAAA, TCAA, TGAA and TTAA are underrepresented.

FIGS. 3Fi and 3Fii is T4 ligase+PEG. TAAA, TCAA, TGAA and TTAA are underrepresented FIGS. 3Gi and 3Gii is T7 ligase+PEG showing the beneficial effect on ligation using T7 DNA ligase.

FIGS. 3Hi and 3Hii is hlig3+PEG. CAAG, CCAG, CGAG, CTAG, TAAA, TCAA, TGAA and TTAA are underrepresented.

Figure 4A:
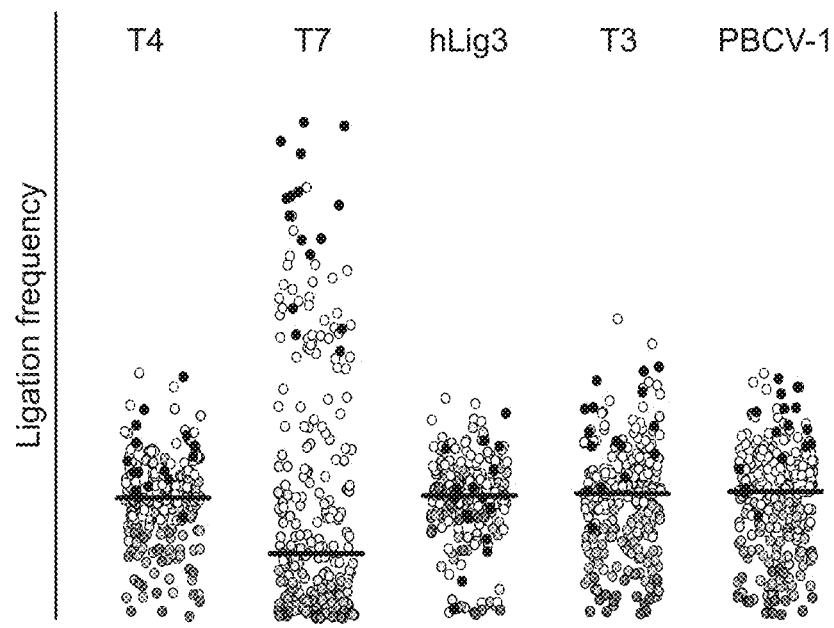

FIG. 4A. shows how median ligation and the spread of bias according to base content of overhangs varies for different ligases as determined by frequency of ligation of every combination of 256 different overhangs from a sequenced library for each ligase.

T4 DNA ligase, T7 DNA ligase, T3 DNA ligase, and PBCV-1 DNA ligase have a similar median bias (shown by the black horizontal line) with a similar distribution of positive bias for GC rich overhangs but some variation in amounts and extents of negative bias for AT rich overhangs. T7 ligase exhibits greater median ligation bias than the other ligases with few overhangs ligated very efficiently, and the majority of overhangs ligated with much less efficiency where frequency of ligation (y-axis) is a measure of efficiency of ligation.

Although not shown in color here, each dot was colored according to its % GC content with different colors for 0%, 25%, 50% and 75% and 100%. The distribution of dots show that GC-rich overhangs tend to ligate more efficiently compared to AT-rich overhangs. The results shown were generated by SMRT sequencing of ligation reactions with 100 nM of the multiplexed four-base overhang substrate with 1.75 µM T4 DNA ligase, T7 DNA ligase, human DNA ligase 3, T3 DNA ligase, or PBCV-1 DNA ligase incubated 1 hour at 25° C. in standard ligation buffer.

Figure 4B:
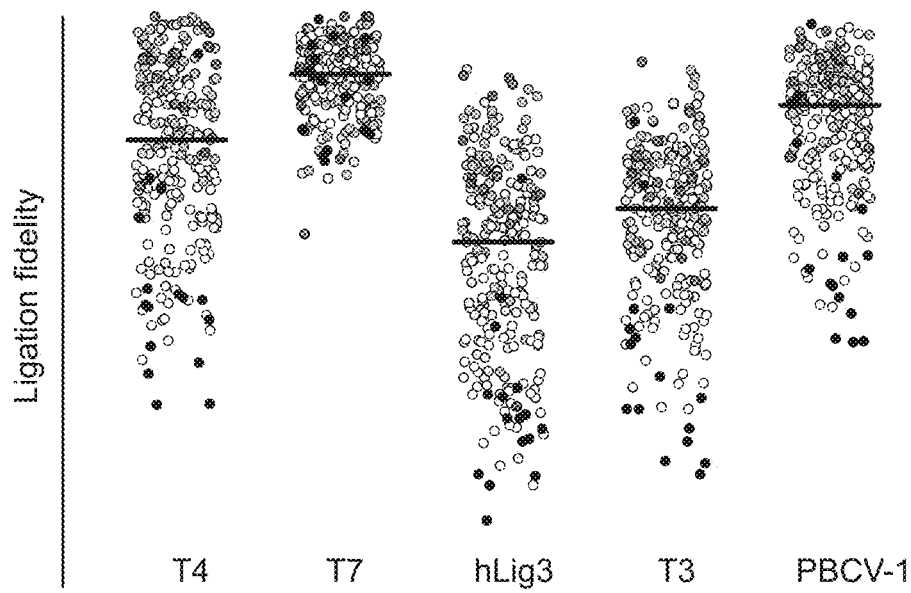

FIG. 4B shows that the median ligation fidelity (see black line) for T4 DNA ligase, T7 DNA ligase, human DNA ligase 3, T3 DNA ligase, and PBCV-1 vary and the spread of GC rich and AT rich overhangs across the ligation fidelity profile also varies between enzymes. T7 DNA ligase shows the highest ligation fidelity. hLig3 shows the lowest ligation fidelity and also the widest spread of data points below the median line. Ligation fidelity was calculated and plotted for all ligases studied. Ligation fidelity is defined as the percentage of correct (Watson-Crick) versus incorrect (mismatch) ligation events.

FIG. 5A-5F shows that polyethylene glycol (PEG) has a significant positive effect on the ligation frequency of overhangs with relatively low GC (a group of overhangs that are generally show less ligation frequency in the absence of PEG) but a slightly negative effect on ligation fidelity. The ligation frequency and ligation fidelity of overhangs is grouped by GC content. The median value is indicated by a horizontal line (dotted line for ligation reactions completed in buffer h did not contain PEG; black for ligation reactions completed in PEG-containing buffer).

Figure 5A:
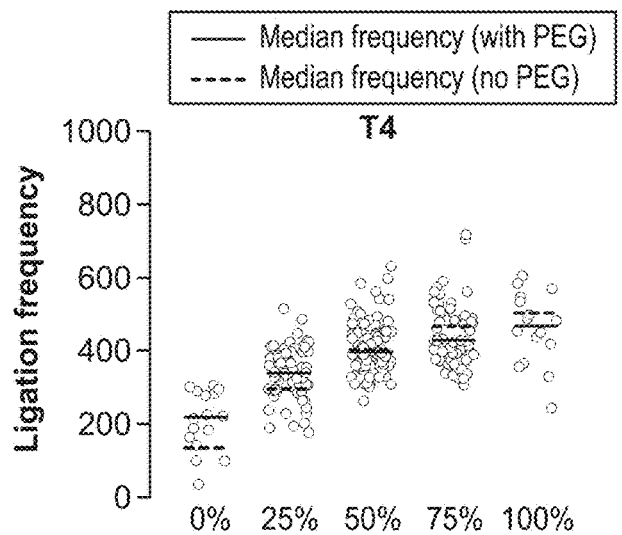
Figure 5B:
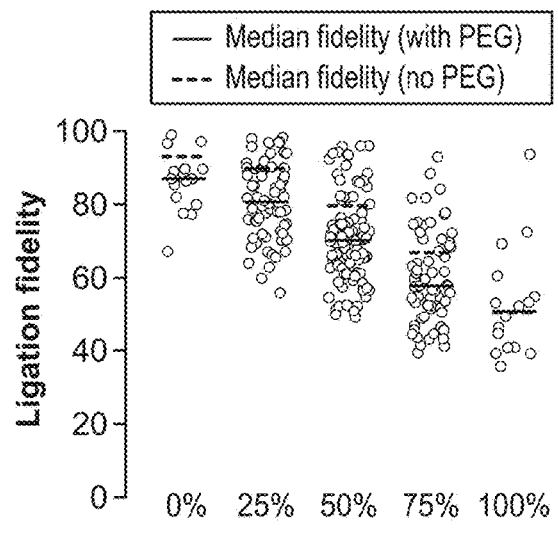
Figure 5C:
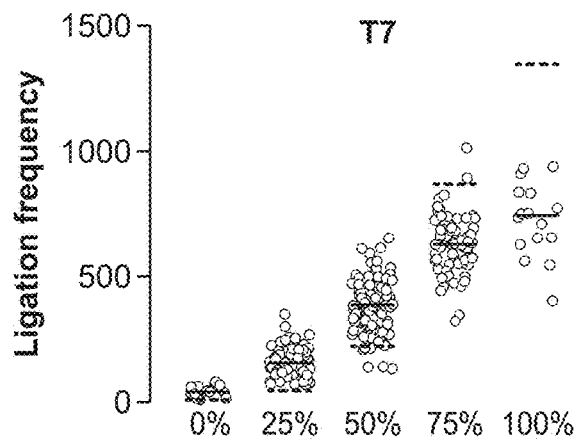
Figure 5D:
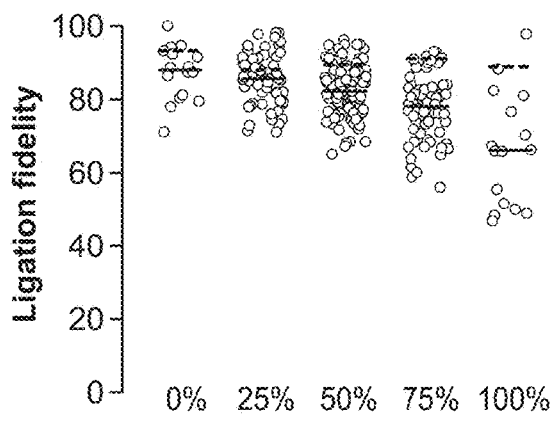
Figure 5E:
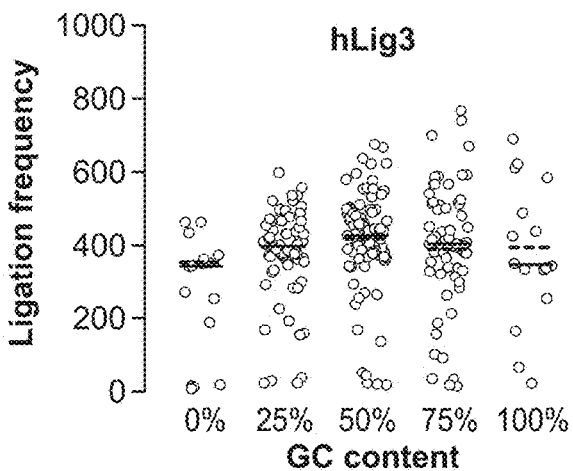
Figure 5F:
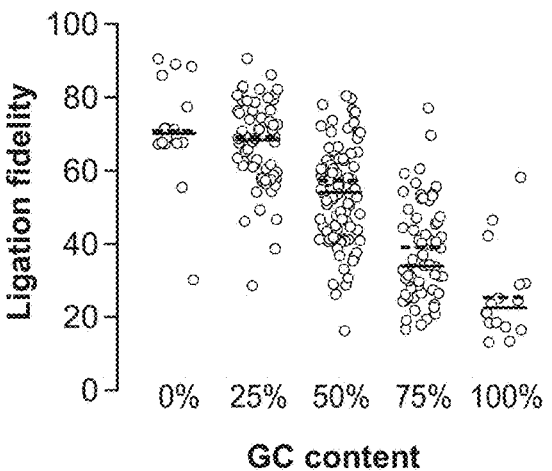
Figure 6:
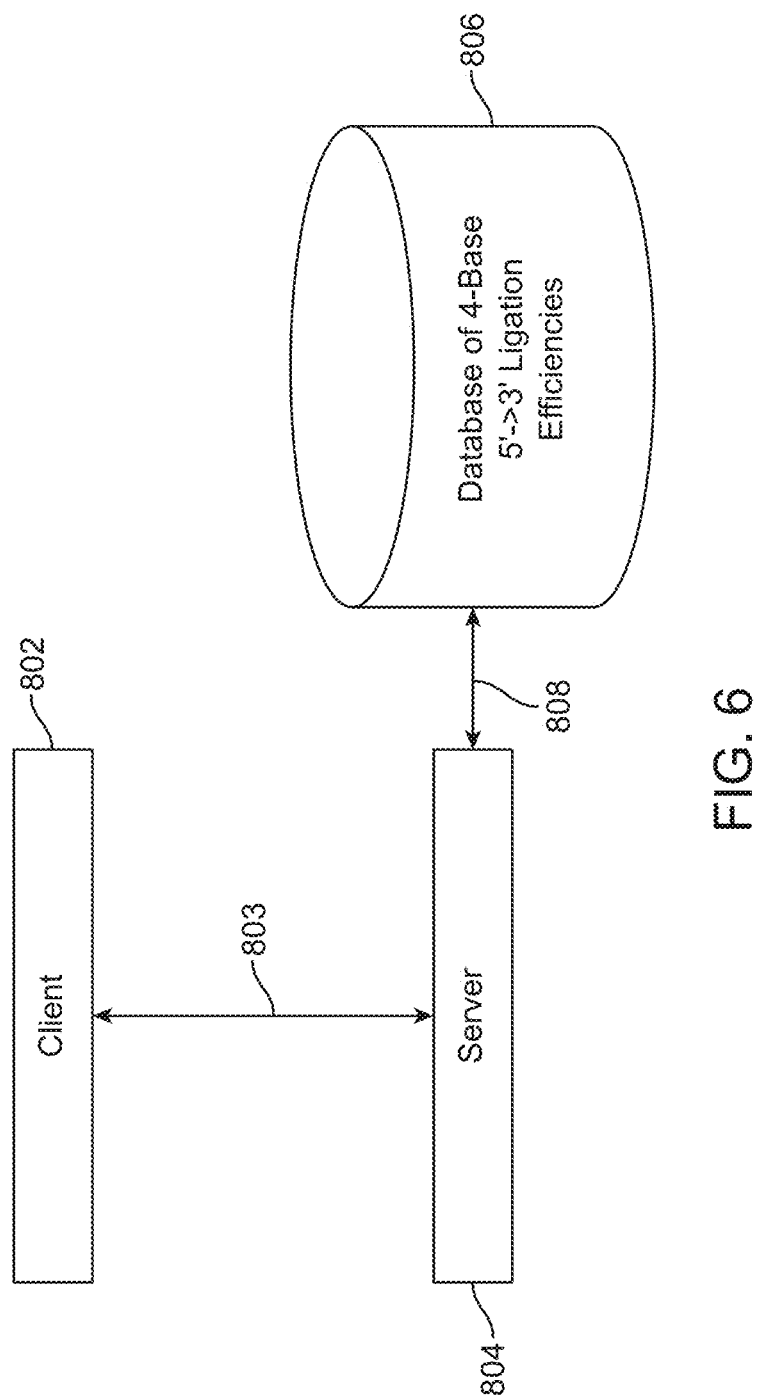

FIG. 5A is T4 DNA ligase (frequency)+/−PEG.
FIG. 5B is T7 DNA ligase (frequency)+/−PEG.
FIG. 5C is hLig3 DNA ligase (frequency)+/−PEG.
FIG. 5D is T4 DNA ligase (fidelity)+/−PEG.
FIG. 5E is T7 DNA ligase (fidelity)+/−PEG.
FIG. 5F is hLig3 DNA ligase (fidelity)+/−PEG.
FIG. 6 shows, by means of a high-level block diagram, a system for generating an estimated overall ligation fidelity for a user-specified overhang sequence set; and also experimental conditions to achieve a desired result. The system utilizes client 802 having bidirectional data communication 803 with a server 804 that in turn has access to storage 806 via 808 where 806 includes a database of 4-base 5'-3' ligation fidelity. This can also be a 2-base, 3-base or 5-base database. Bidirectional data communication 803 may be implemented using a local connector such as a local area network (LAN) or a wide area network. Server 804 may be a dedicated resident server or may be implemented in the cloud. Data storage 806 may be co-loaded with server 804. The user enters data into client 802 which may include a browser interface. In addition to running a browser, client 802 may host a graphical user interface for use to enter sets of 5'-3' 4-base canonical form of AGCT or other overhang sets or for selecting experimental conditions for ligation such as a selected restriction endonuclease, a selected ligase, a buffer contain PEG, temperature and time of reactions, other experimental details.

Figure 7:
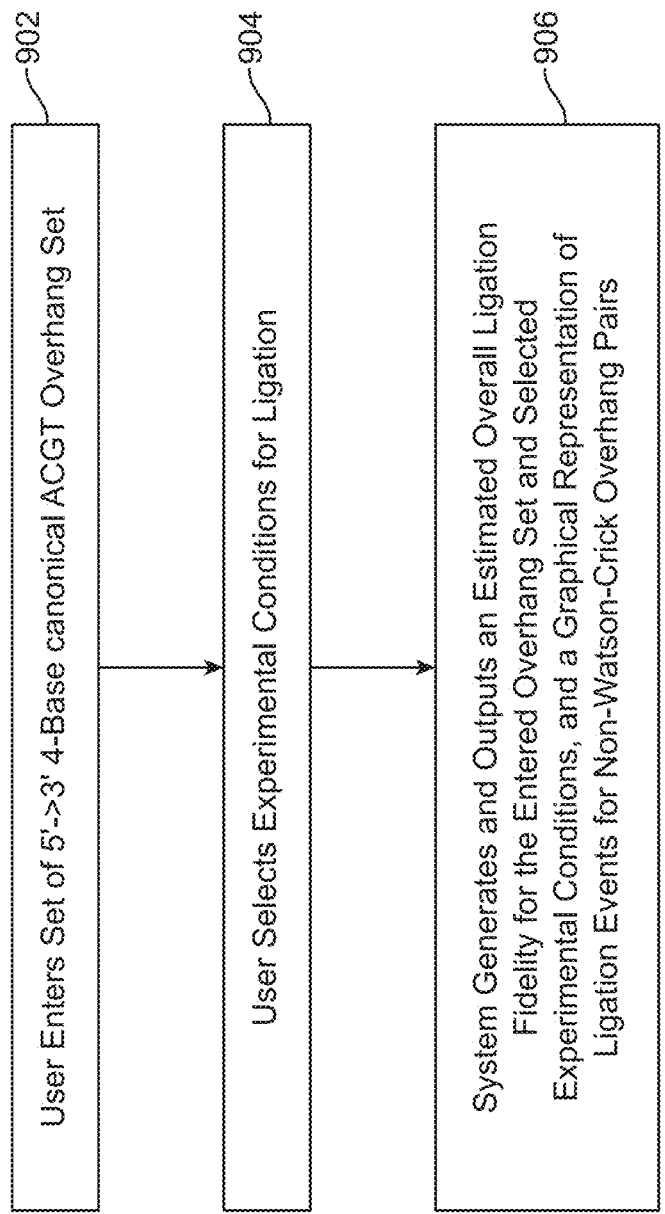
Figure 8:
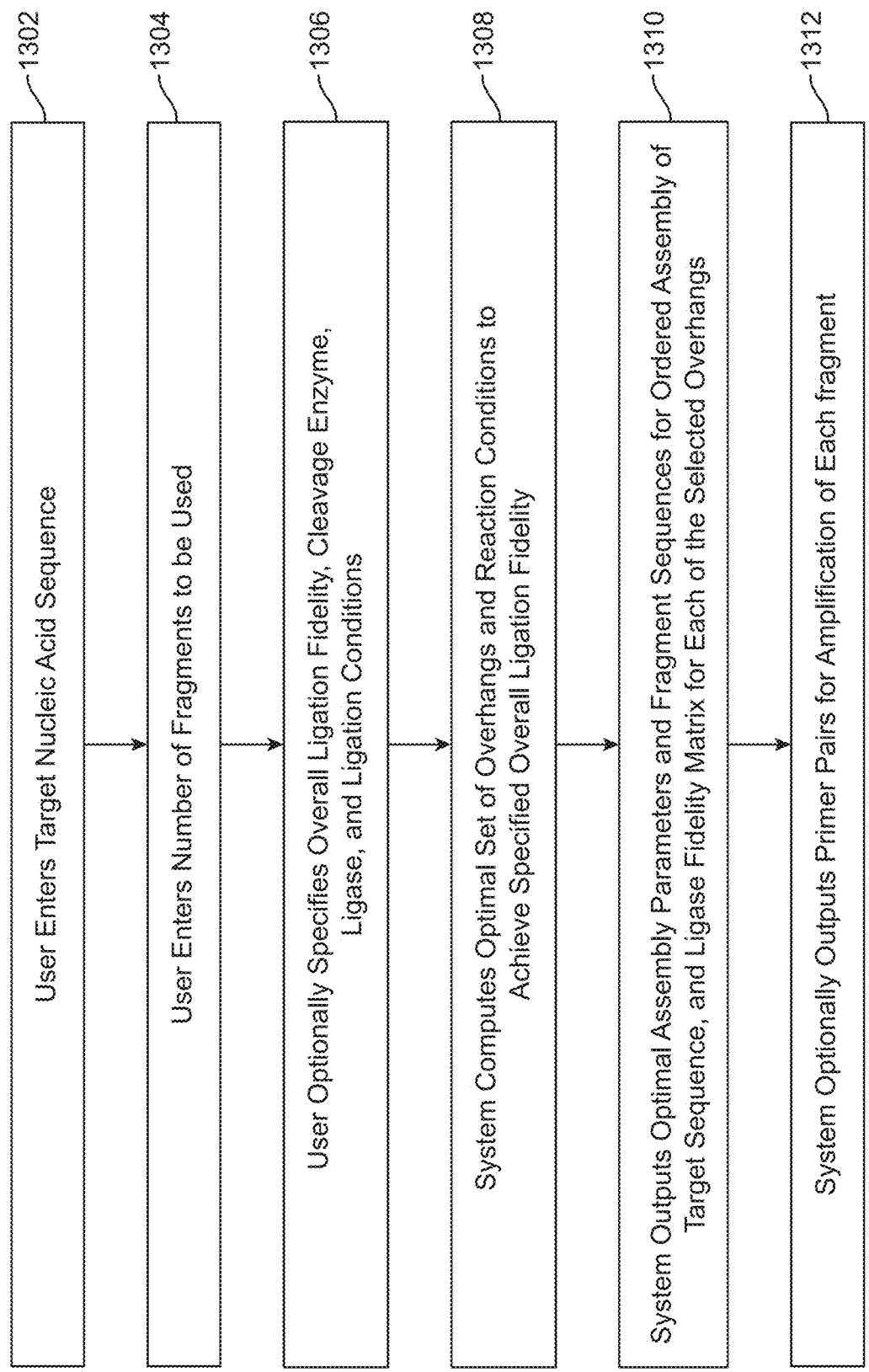

FIG. 7 shows input and output steps in a high-level flow diagram for execution of an assembly reaction using the system outlined in FIG. 8. user enters a set of overhang sequences of any desired length, for example, the set of overhang sequences will be a set of 5'-3' 4-base overhang sequences 902. The set will contain more than one 4-base overhang sequence such that each member of the set differs from all the other members of the set. Each overhang sequence represents a member of a single overhang pair that the user preferably wishes to use in an experiment to join in order a plurality of double stranded nucleic acid fragments. The 4-base overhang may be represented as a Watson-Crick pair of overhangs. A single overhang pair in a set may vary with respect to ligation fidelity depending on whether a particular sequence is a 5' sequence or its complement. Each member pair is considered separately from the other member pairs in the set. The user may select experimental conditions for ligation of fragments having overhangs corresponding to the entered sequences in 902. These experimental conditions include, for example, time of incubation with ligase, temperature of incubation, and ligation frequency and fidelity for selected ligases 904. By accessing a database of ligation fidelity for individual overhangs or overhang pairs, the system generates an output describing the ligation fidelity for the entered overall overhang sequence set and/or for individual overhang pairs in the set 906. The system may additionally output a graphical matrix representation of ligation fidelity for the selected overhang sequence pairs. If the identified fidelity efficiency of the set of 4-base overhang sequences input by the user is rejected by the user, the user is enabled to assess the ligation of the identical set of 4-base overhangs under different selected experimental conditions or to enter a modified set of 4-base overhang sequences under the same or different experimental conditions to determine how to join the set of double stranded nucleic acid fragments in an ordered assembly.

FIG. 8 is a high-level flow diagram showing inputs in addition to system output steps.

Individual examples are provided for user entry of input (1302-1306) generating outputs 1308-1312. However, the input parameters in 1302-1306 may be substituted or added to by any one or more or two or more of the following:
  (a) a target nucleic acid sequence;
  (b) a set of polynucleotide fragments;
  (c) a partial set of polynucleotide fragments provided by the user and a partial set output from the system;
  (d) a set of vectors having specified junction sequences;
  (e) a preferred overhang length;
  (f) excluded overhangs;
  (g) a set of overhangs of specified length;
  (h) a partial set of overhangs of specified length provided by the user and a partial set of overhangs output by the system;
  (i) a choice of ligase, e.g., T4 DNA ligase, T7 DNA ligase, PBCV-1, T3 ligase, hLig3 or any other ATP dependent DNA ligase or NAD+ dependent ligase such as Taq DNA ligase;
  (j) a choice of restriction endonuclease e.g. one or more of Esp3I, SapI, BbsI-HF; BspQI, HgaI, BsaBI, BsaJI, BsaI, BsaI-HFv2, BsiI, BsmAI, BsmBI, BsmFI, BsmI, Bsr DI, BsrI, BtgZI, BtsCI, BtsMutI, Btsv2, BspQI, BpiI, BfuI, BspMI, PaqCI and isochizomers of the same;
  (k) a preferred number of fragments;
  (l) a preferred incubation time; e.g., 1 hour, 5 hours, overnight;
  (m) a preferred incubation temperature, e.g., 37° C. or 45° C.;
  (n) preferred reaction conditions in addition to time and temperature;
  (o) a preferred overall ligation efficiency;
  (p) a minimum acceptable ligation efficiency;
  (q) maximum GC content;
  (r) maximum AT content;
  (s) acceptable bias.

Output may include one or more of the following:
(a) any of the above parameters described above not specified by the user;
(b) warnings if ligation fidelity determined from user input parameters is too low based on manual input of certain parameters where the warning might include internal RE sites, low efficiency junction sites formed from individual overhang pairs; excessive bias of some ligation events over others;
(c) matrix or tabular format for all specified overhang pairs showing strongly ligating Watson Crick pairs and mismatch overhang pairs with color coded frequency of occurrence;
(d) ligase fidelity viewer grid to show predicted fidelity for chosen set;
(e) provide alternative solutions with altered specified experimental parameters;
(f) graphical display of assembly design, annotated if using full sequence;
(g) exportable fragment/primer sequences for synthesizer.

The system then computes any of the above parameters not provided by the user to achieve the requested output using a database of n-base overhangs and 5'-3' ligation efficiencies under various reaction parameters to enable the user to create an ordered assembly of X number of fragments with a defined ligation efficiency.

Figure 9A:
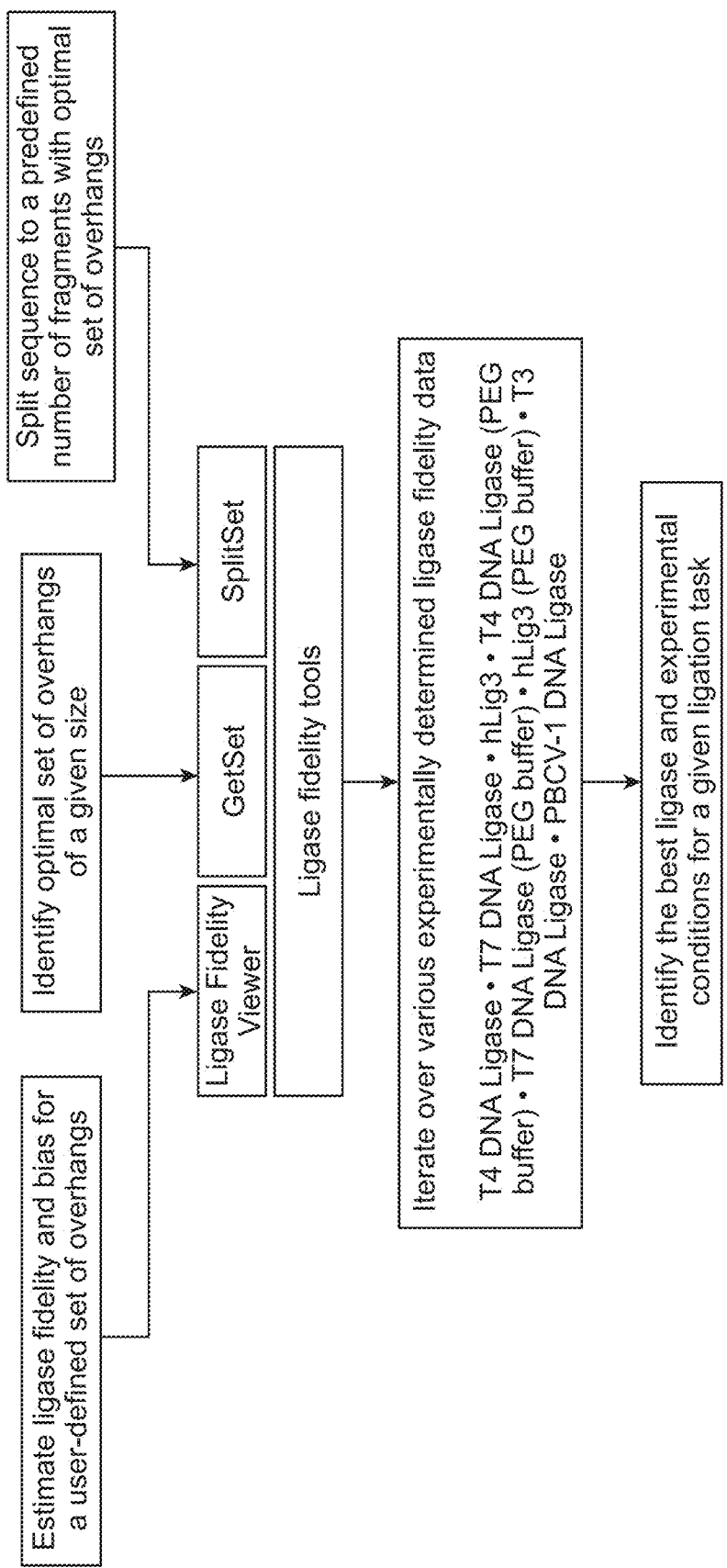

FIG. 9A-9D shows that how the data presented in FIG. 3Ai/3Aii-3Hi/3Hii) to FIG. 5A-5F can be integrated into a computer. In addition to the ligase fidelity viewer in WO 2020/081768 and a version that includes drop down menus for length of overhang and for user input of a predetermined selection of overhangs for assessment of frequency and fidelity parameters, additional parameters include use of PEG and/or aprataxin in the buffers selection. A further drop down menu for adding to the user interface page in FIG. 9B (Ligase Fidelity Viewer) is a drop down menu that permits choice of a ligase and this will influence the selection of overhangs based on frequency, bias and fidelity data described herein. FIG. 9C shows the drop down menus for GetSet, the interface that will inform the user as to how good their chosen set of overhangs will perform in a specified ligation assembly reaction and whether certain overhangs should be included or excluded from the set. FIG. 9D shows the drop down menu for SPLITSET which informs the viewer what sites should be included and which should be excluded in an in silico sequence for the production of fragments from the corresponding DNA by targeted cleavage or by DNA synthesis.

Figure 10:
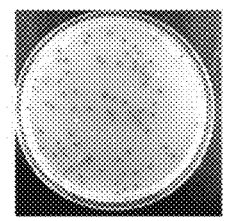

FIG. 10 shows that PEG increases the frequency of colonies obtained from multi-fragment assembly with T4 DNA ligase and BbsI-HF restriction endonuclease obtained for a particular concentration of DNA compared to the same DNA in the absence of PEG. All PEG sizes showed some improvement. Preferred embodiments included PEG 3350 and PEG 6000.

FIG. 11 shows that PEG 6000 enables the use of 10 fold less DNA to achieve substantial colony representation following assembly of 24 fragments of DNA using T4 DNA ligase and BbsI-HF.

FIGS. 12A and 12B shows that 50 DNA fragments having overhangs determined by the computer tool described in FIG. 9A-9D that included adjustments for the ligation preferences for T4 DNA ligase enabled improved efficiency of assembly of the T7 viral genome from the 50 fragments as determined by plaques on a lawn of bacteria.

Figures 13A, 13B:
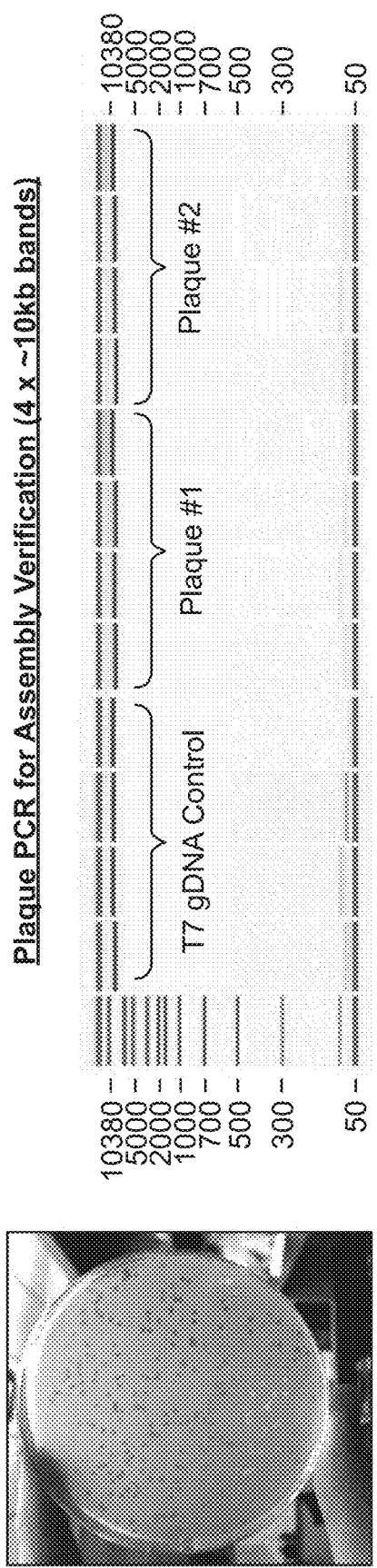

FIGS. 13A and 13B show that plaques obtained on a lawn of bacteria do indeed contain intact phage T7 DNA.

Figure 14:
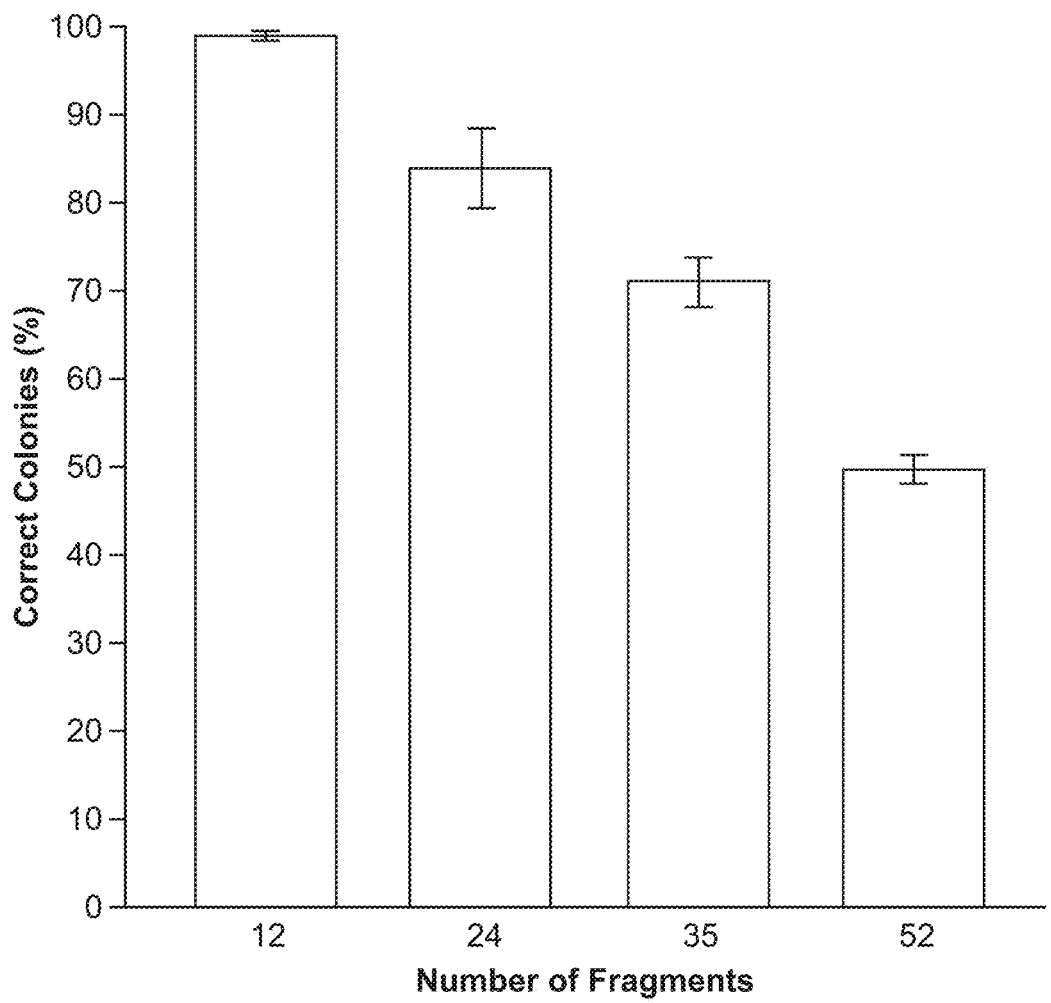

FIG. 14 shows that the percentage of colonies that contain correctly assembled constructs is maintained at least 50% for 52 fragments using the tools described herein to design overhangs for correct end joining. These results are obtained from one pot fragment assembly reactions.

Figure 15:
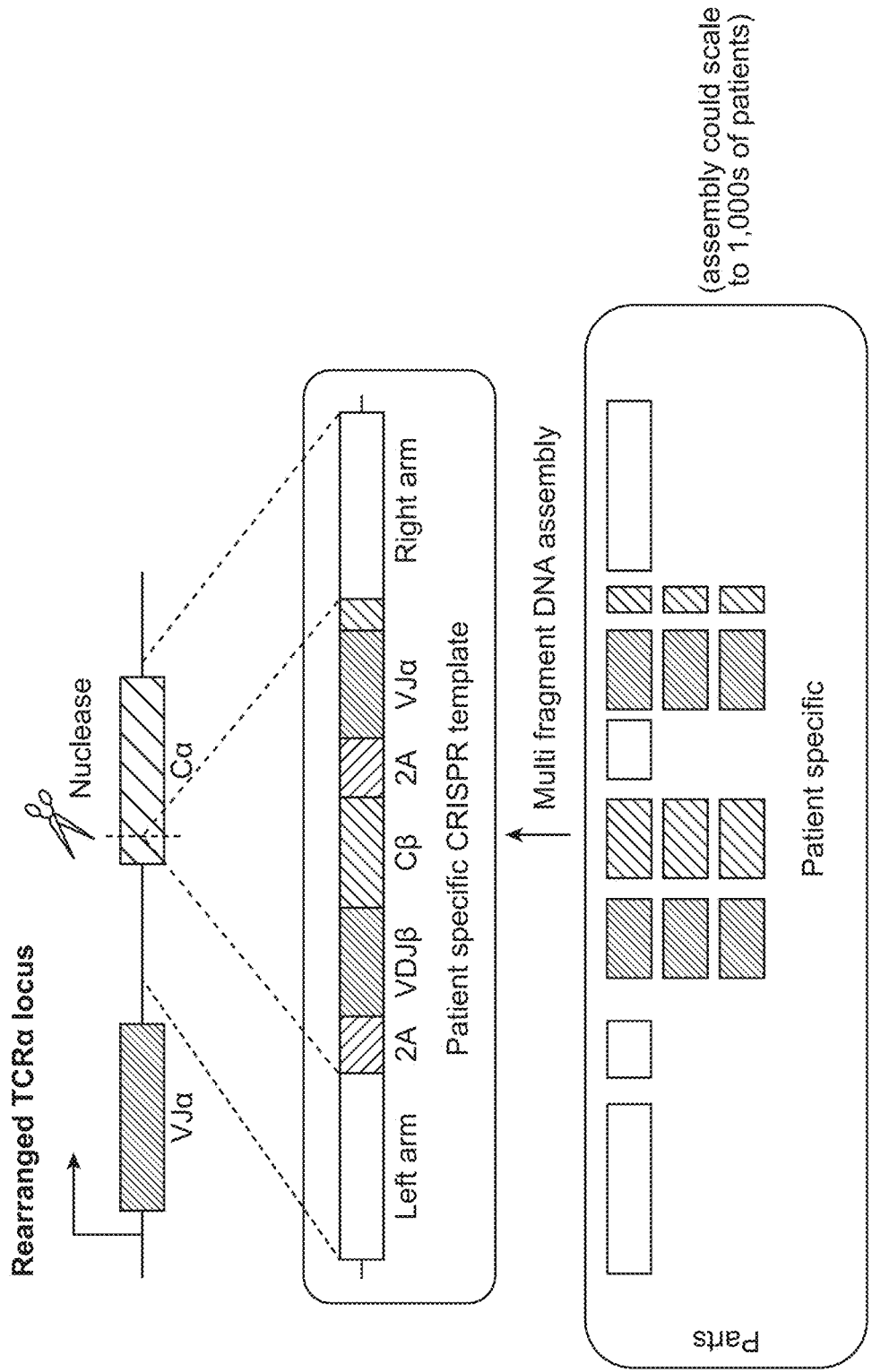

FIG. 15 shows a cartoon of how improved multi-fragment assembly methods can be used for scale-up for Car-T cell therapy for thousands of individual patients. Tumor cells from individual patients are analyzed to discover their unique tumor specific antigens and the DNA sequences for genes that encode these neoantigens containing mutations. The patient's own T-cells are removed and engineered to insert an assembled gene at a target site in the genome that has been recognized and cleaved by CRispR. The T-cells can then be reintroduced into the patient to destroy the tumor cells. Here a subset of multiple components required to synthesize a tumor antigen will be conserved and a subset of components will not be conserved. The entire region of interest may be maintained in plasmid libraries ready for use and individual non conserved fragments where the mutation is identified can be used in the assembly reaction. In this way, the entire gene need not be made de novo for each patient allowing for higher throughput of samples in the workflow.

Figure 16:
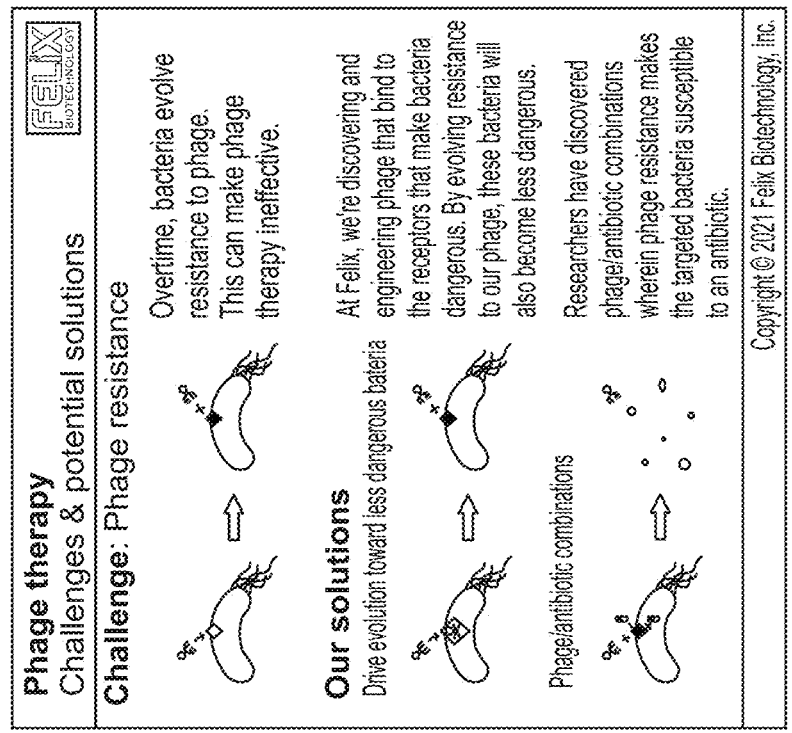

FIG. 16 shows a cartoon of phage engineering to treat drug resistant bacterial infections for potential antibiotic solutions. Here a phage genome is divided into small pieces and various mutations introduced into any one or more fragment. Once assembled using the multi-fragment system described herein, the engineered phage can be assayed for their ability to invade and destroy the target bacteria.

DESCRIPTION OF EMBODIMENTS

Unless defined otherwise, all technical and scientific terms used herein in the molecular biology field have the same meaning as commonly understood by one of ordinary skill in the art to which this invention belongs. Singleton, et al., DICTIONARY OF MICROBIOLOGY AND MOLECULAR BIOLOGY, 2nd ED., John Wiley and Sons, New York (1994), and Hale & Markham, THE HARPER COLLINS DICTIONARY OF BIOLOGY, Harper Perennial, N.Y. (1991) provide one of skill with the general meaning of many of the molecular biology-related terms used herein. Certain terms are used herein for which explanations are provided below.

As used herein, the term "target polynucleotide" (or "large DNA") refers to the end product of a ligation based ordered assembly of fragments that may be DNA, RNA or a mixture thereof.

As used herein, the term "polynucleotide fragments" (or "DNA fragments") refer to the building blocks that when assembled, create the target polynucleotide. These building blocks may be derived from sequence databases and may contain promoter sequences, enhancer sequences, coding sequences etc. Polynucleotide fragments may be made by chemical synthesis (IDT, Coralville, IA) or by enzymatic synthesis using for example, a terminal transferase-based synthesis. The fragments made in this way may be assembled in a preliminary step from the products of chemical and/or enzymatic synthesis to form larger polynucleotide fragments suitable for assembly into a gene. Where individual polynucleotide fragments are amplified from a template, e.g., by PCR their length does not exceed the processive capability of the polymerase used in amplification. For example, for Taq polymerase, amplicons rarely exceed 5 kb-10 kb and may have a minimum length of 15 nucleotides in length.

As used herein, the term "oligonucleotide" in the intended context refers to a multimer of at least 10, e.g., at least 15 or at least 30 nucleotides. In some embodiments, an oligonucleotide may be in the range of 15-500 nucleotides in length, or more. Any oligonucleotide used herein may be composed of G, A, T and C, or bases that are capable of base pairing reliably with a complementary nucleotide.

As used herein, the term "sequence" refers to a series of letters each letter corresponding to a base e.g. A=adenine, T=thymine, U=uracil, G=guanine and C=cytosine. Modified nucleotides (nucleoside (base and deoxyribose) and a phosphate) may optionally be included in an overhang sequence and hence in a ligation efficiency database. A plurality of letters in a specific order describes figuratively the base (also referred to as nucleotide) composition of a molecule.

As used herein, the terms "perfect match", "complementary" and Watson and Crick pairs each refer to the pairing by hydrogen bonds of bases on separate strands of a duplex DNA where A is matched to a T or U and G is matched to a C.

As used herein, the term "junction" refers to a position in a target polynucleotide where component polynucleotide fragments have been joined by a ligase. The term "junction" also refers to a position in a sequence of a target polynucleotide in a database where fragmentation is recommended for assembly of a target polynucleotide from an optimized set of fragments. The context of the word "junction" will make clear which of the two meanings is intended. The assembly methods described herein may be used to create scarless junctions in the target polynucleotide meaning that the junction in the target polynucleotide would be indistinguishable from the corresponding position in the original polynucleotide sequence.

As used herein, the term "overhang" refers to a single stranded region at the end of a double stranded fragment polynucleotide for example DNA. The overhang is preferably formed by an enzyme that creates a staggered cleavage of the nucleic acid on both strands of the duplex outside the recognition region. The overhangs are generally 5' overhangs. The overhang can be defined by its length and its sequence. For example, there are 256 different possible 4-base overhangs ($4^4$). Overhangs of 2-bases, 3-bases, 4-bases and 5-bases are exemplified here, generated by restriction endonuclease cleavage. The overhang can contain 2-8 bases although 3 or 4-base overhangs are generally preferable. The preference derives from the availability of restriction endonucleases that cleave double stranded DNA outside the recognition site to produce 3 or 4-base overhangs and from the number of possible overhang pairs in a set which is sufficient to optimize ligation of a plurality of polynucleotide fragments to form a target polynucleotide.

Matching the overhang from one polynucleotide fragment with a second complementary overhang on a second polynucleotide fragment results in a junction if a ligase is added to the mixture and ligation occurs depending on the ligase preferences for the overhang sequence and its complement. The first overhang and the second complementary overhang are referred to as overhang pairs or complementary overhangs. While not wishing to be limited by theory, it is proposed here that combining the ligase with the restriction endonuclease in a single assembly reaction mixture results in a significant reduction in inappropriate hybridization and ligation events. These inappropriate events occur when a cleavage product that consists of an overhang and the restriction endonuclease recognition sequence reconnects with the assembly fragment from which it has been cleaved or reconnects with another cleavage product. In both scenarios, the sequences are cleaved again by restriction endonucleases in the reaction mix to liberate the polynucleotide overhangs for proper ligation to the compatible polynucleotide fragment partner. Other inappropriate events may occur when non complementary overhangs anneal, resulting in mismatches. This generally occurs only with one or two mismatches and can affect the order of assembly unless the occurrence of mismatches of annealed overhangs in factored into the assembly strategy.

As used herein, the term "inputs" refers to the information the user enters into the computer. These may include: specified reaction conditions, a target polynucleotide sequence that can be divided into polynucleotide fragments, excluded overhangs, included overhangs, and the number of desired fragments or overhangs. Input parameters are received by the computer.

As used herein, the term "outputs" refer to instructions from the computer that enable the user to make the desired target polynucleotide. These may include: overhang sets with preferred ligation fidelity scores for a specified number of junctions, and/or full polynucleotide fragment sequences based on input of the target polynucleotide. Where polynucleotide fragment sequences are entered by user, then the computer output may include pairs of overhangs that avoid internal sites, palindromes and repeat overhangs and provide a high overall fidelity score for the specified reaction conditions including cycling conditions, incubation time and temperature and recommended enzymes for optimizing ligation fidelity. Computer outputs may further provide graphical display of fragment assembly design and fragment sequences or link to the same. A computer output may also provide a matrix of ligation frequencies for all combinations of the selected overhangs in order to graphically illustrate the predicted fidelity for a chosen set of overhangs and their complements or link to the same.

By default, the tool can provide ligation data in a graphical output, indicating the general efficiency of each connection. For example, in FIG. 11A-11B, the checkbox can be toggled to display normalized ligation counts. In multiplex ligation assay, the relative ligation frequency was experimentally determined for all 256 4-base overhangs in a single experiment. Total ligation events for each experiment were normalized to 100,000; in this case, a typical frequency for any single Watson-Crick pair was 300-400 observations per 100,000 ligation events. Further details are provided in: Potapov, et al. Nucleic Acid Research, 46, e79 (2018); Potapov, et al. Cold Spring Harbor Laboratory, bioRxiv, doi: https://doi.org/10.1101/322297 (2018); and Potapov et al. ACS Synthetic Biology 711, 2665-2675 (2018).

As used herein, the term "experimental conditions" refer to choices of a ligase, endonuclease and/or other enzymes as desired for the workflow and their unit ratio. The conditions also refer to buffers and cofactors in the buffers. For example, the ligase to restriction endonuclease unit ratio may be within the range of 1:10-1:1000 regardless of the type of DNA ligase or Type IIS restriction endonuclease selected. Experimental conditions may include salt concentrations, temperature and time used to complete ligation of overhangs and may further include cycling conditions for ligation reactions. Experimental conditions may be selected to reduce the assembly time for large numbers of fragments, improve the fidelity score of the selected set of overhangs, improve the activity of the cleavage endonucleases while retaining ligase activity and performance and/or reduce background of incorrect assemblies. Experimental conditions may also affect removal of mismatches in the target polynucleotide. Watson/Crick perfect matches may be preferred although in some cases a single base mismatch in the overhang may provide a higher fidelity score for ordered assembly than a perfect match of bases that do not readily hybridize as deduced from the ligation frequency tables. Alternative splicing may also occur during assembly resulting in a mismatch at a junction. Mismatches can be removed using EndoMS or T7 Endo I, or other repair enzyme that identifies mismatches, to cleave the DNA at the mismatch. The term "experimental conditions" includes ligation conditions and the context will determine if these terms are interchangeable.

As used herein "ligation frequency" refers to the number of times an overhang will ligate to another overhang out of a total number of ligations (e.g. 100,000 ligations).

As used herein, the term "ligation fidelity" refers to a numerical assessment of discrimination against the ligation of substrates containing mismatched base pairs bias (preferential ligation of particular sequences over others). Ligation fidelity also refers to the fraction of ligation events that are correct (Watson-Crick ligation products) versus incorrect (mismatch products). In a 4-base overhang, the possibilities are that no base is mismatched (Watson-Crick ligation product), there is a 1-base mismatch, 2-base mismatch, 3-base mismatch or all 4-bases are mismatched.

As used herein, the term "ligation fidelity by overhang" or "ligation fidelity score for an individual overhang" refers to the frequency at which an individual overhang and its complement independently ligate to a perfectly complementary overhang relative to all overhangs in a set and their complements. A fidelity score can be calculated by consulting a ligation frequency table, which comprising individual experimentally defined measurements of the number of ligation events for each overhang to all overhangs of the same length (including itself). A ligation fidelity score for an individual overhang is calculated as the number of ligation events that occur between the individual overhang and its complement relative to the total number of ligation events that occur between (i) the individual overhang and all of the overhangs in the set and their complements; and (ii) the complement of the individual overhang and all of the overhangs in the set and their complements.

As used herein, the terms "ligation fidelity of an entire set" and "overall fidelity score" refer to the expected ratio of correctly ligated assemblies to incorrectly ligated assemblies based on the individual ligation fidelity scores for each member of a given set of overhangs. An overall fidelity score for a set of overhangs can be calculated by multiplying the individual ligation fidelity scores for the overhangs in the set together.

As used herein, the term "overall assembly fidelity" refers to the actual number of correctly assembled target nucleic acids compared to the predicted number of correctly assembled target nucleic acids. For example, the assembly efficiency of 10 polynucleotides with overhangs can be determined by the number of times all 10 junctions are ordered correctly in the population of target polynucleotides. Assembly fidelity may be greater than 20%, 30%, 40%, 50%, 60%, 60%, 70%, 80%, or 90%.

The term "ligation efficiency" refers to the number of correct assemblies as a function of time. As used herein, the term "assembly efficiency" refers to the rate at which full length ligation products (complete target nucleic acids as determined by size or colony formation or sequencing) accumulate in a particular assembly reaction after a particular time period. An arbitrary unit of time may be selected which will provide an overall average/unit time for ordered assembly of a target polynucleotide. However, the ligation efficiency may not be linear over a selected incubation period.

The term "ligation yield" refers to the number of correct assemblies.

The term "ligation accuracy" refers to the number of correct end joining of fragments over number of total assemblies. This may be determined by sequencing.

The use of the term "ligation" above refers to the product of assembly which requires a DNA ligase to join fragments. The use of the term "ligation" below is attributable to specific features of bias and/or fidelity of the ligation event for different ligases where it was found that variability existed in a manner that could be useful or detrimental to a planned assembly.

The term "ligase" refers to an enzyme that is capable of joining two polynucleotides covalently. Many different ligases have been described in the art and are widely known (see Ellenberger et al. Annual Review in Biochemistry, 77, 313-338 (2008); Bauer et al. PLOS ONE, 10, 12:e0145046 (2017)). Ligases for use in assembly reactions may include ATP ligases and NAD+ ligases such as T4 DNA ligase, T7 DNA ligase, Taq DNA ligase, viral ligases such as chlorella virus DNA ligase (e.g., PBVC-1 ligase), bacterial ligases such as bacterial LigA (e.g., *E. coli* DNA ligase) and LigD; archeal ligases such as *Thermus thermophilus* (Tth) Ligase and eukaryotic ligases such as Mammalian Lig1 and hLig3.

The term "multi-fragment assembly" refers to multiple DNA fragments or a set of DNA fragments of any size greater than about 15 nucleotides that have been synthesized chemically or within plasmids in a library of bacteria containing plasmids with different inserts. The fragments may be all a similar or the same size or may have various sizes.

The term "PaqCI" refers to a 7-base cutter restriction endonuclease derived from *Pauciibacter aquatica*. The endonuclease identified here as PaqCI includes any variant having at least 80%, 85%, 90%, or 95% sequence identity to SEQ ID NO: 1.

In one embodiment the ordered assembly of multiple polynucleotide fragments into a single DNA relies on the use of two different enzymes, namely a Type IIS restriction endonuclease and a ligase. Type IIS restriction endonucleases recognize 4, 5, 6 or 7-bases in a DNA and cleave outside the recognition sequence to provide polynucleotide fragments with overhangs that may be 2-bases, 3-bases, 4-bases or 5-bases in length. These fragments become joined when complementary overhangs anneal and a ligase seals the join.

An increasing number of different Type IIS restriction endonucleases are being described that recognize up to 6-bases and cleave the DNA outside the recognition sequence to create 2-4 base overhangs. Many of the current endonucleases may be found in the commercial literature (including www.neb.com) provided by New England Biolabs (NEB), Ipswich, MA, including recognition sequences and length of overhang generated by cleavage. New endonucleases are listed in a regularly updated database (see REBASE® on www.neb.com from New England Biolabs). For example, this includes: AcuI, AlwI, BaeI, BbsI, BbnI, BccI, BcgI, BciVI, BcoDI, BspMI, BfuAI, BmrI, BpmI, BpuEI, BsaI, BsaXI, BseRI, BsgI, BsmAI, BsmBI, BsmFI, BspCNI, BspMI, BspQI, BsrDI, BsrI, BtgZI, BtsCI, BtsI-MutI, CspCI, EarI, EciI, Esp3I, FauI, FokI, HgaI, HphI, HpyAv, MboII, MlyI, MmeI, MnII, NmeAIII, PleI, SapI, and SfaNI. Only SapI has a 7-base recognition sequence and cleaves DNA to produce a 3-base overhang. These endonucleases are all available from New England Biolabs, Ipswich, MA The recognition sequences and overhangs are described by NEB along with reaction buffers, reaction temperatures and storage conditions. Isoschizomer information is also provided.

Described herein is a novel Type IIS restriction endonuclease (PaqCI) that has a specific 7-base recognition sequence and cleaves the double stranded DNA to completion and without star activity (see FIG. 1C and FIG. 1D) preferably with the assistance of a synthetic oligonucleotide, to produce a four base overhang. A significant advantage of PaqCI for polynucleotide assembly reactions is the reduced likelihood of a 7-base recognition sequences within a polynucleotide fragment sequence. Internal recognition sequences are undesirable as the polynucleotide fragment would be cleaved and thereby disrupt the ordered assembly of the set of fragments.

Recognition sequences for PaqCI are added to the termini of fragments by primer dependent amplification or by chemical nucleic acid synthesis. The sequences adjacent to the restriction endonuclease recognition sequence create the overhangs. Preferably, these are selected so as to optimize joining of an ordered set of fragments that comprise a target polynucleotide or large DNA.

Although the use of PaqCI is described here in the context of ordered polynucleotide fragment assembly, this enzyme may also be used in a variety of other bioengineering methods and analysis of genomic DNA including chromatin where endonucleases with recognition sequences of six or more bases are preferred.

In an embodiment of the invention, the ordered assembly of multiple polynucleotide fragments into a single DNA may rely on the use of a ligase but not require a restriction endonuclease. Restriction endonucleases are not required when the polynucleotide fragments with designed overhangs are generated by chemical synthesis instead of endonuclease cleavage. However, an advantage of the two enzyme system is that a polynucleotide fragment can be inserted into plasmids that are retained in bacteria and stored indefinitely for future use. When needed, the bacteria can be readily grown to produce the desired quantity of substrate for endonuclease cleavage and ligation.

Ordered assembly of multiple polynucleotide fragments that relies on ligation of annealed overhangs has been greatly improved by the systematic analysis of frequency of overhang ligation, bias and fidelity. Factors that have been identified include the length of the overhang, the number of different overhangs in a set of overhangs, the GC content of the overhangs, the bases that arise at the edges of the overhang sequence, the ligation reaction conditions and the type of restriction endonuclease that generates the overhang (see WO2020/081768).

In present embodiments, surprisingly the sequence preferences of various ligases with robust end joining activity have been identified and found to contribute in significant ways to the frequency and fidelity of the ligation product. Differences and similarities of various ligases have been identified including the extent of mismatches tolerated between annealed overhangs, and the preference for certain patterns of A, T, G and C bases in an overhang.

The ligases described in the examples are all end joining ligases catalyzing the formation of a phosphodiester bond between the 3'-hydroxyl of one DNA strand and the 5'-phosphorylated termini of another DNA strand. They all contain at least two domains corresponding to: a nucleotidyl transferase domain (NTase) with a catalytic lysine residue; and an oligonucleotide binding domain (OBD) having a DNA binding surface. The ligases also optionally contain a third domain. For example, T4 DNA ligase and T3 DNA ligase both contain an N-terminal DNA binding domain while Human ligase 3 (hLig3) contains an N-terminal poly ADP-ribose polymerase-like zinc finger domain and the chlorella virus DNA ligase (PBCV-1) contains a latch domain. However T7 DNA ligase does not contain a third domain. While not wishing to be limited by theory, the presence or absence of a third domain may play a role in ligation bias, promiscuity and/or fidelity.

End joining activity was analyzed for each of 256 combinations and permutations of the four base overhangs. Using the assay schematically described in FIGS. 2A and B, matrices of 256×256 sequences were constructed from sequencing data obtained from ligated overhangs. (see FIG. 3Ai/3Aii-3Hi/3Hii). The data from these assays were added to a computer design tool described in FIG. 6, FIG. 7, FIG. 8 and FIGS. 9A and 9B that allows a user to select a set of optimized overhang sequences for ordered assembly of a set of polynucleotide fragments.

The computer tool described in WO 2020/081768 provides access to optimized sets of overhangs based on their annealing patterns. A restriction endonuclease can be selected from a menu of options for cleavage to generate overhangs. Metrics of ligation frequency and fidelity are provided for different overhangs using a single ligase, namely T4 DNA ligase, under assembly conditions that can be also selected from drop down menus containing buffer options and temperature and incubation time options.

The ligation data described herein and in WO 2020/081768 captures ligase-substrate preferences and further enhances the precision of the previously described assembly options. This is especially important when large number of polynucleotide fragments (greater than about 20 fragments) are used for ordered assembly of a large DNA. The computer tool provides a suitable user interface for informing the user about the predicted efficiency (frequency) and fidelity profile for any fragment overhang or set of fragment overhangs under various experimental conditions. The data obtained on the ligation preferences of different ligases extends the menu of experimental conditions. The interface for the Ligation fidelity Viewer, GetSet and SplitSet containing drop down menus allows the user to select a suitable ligase for design of fragments with overhangs from a large DNA sequence in silico. Alternatively, the user can select a suitable ligase for a fixed set of overhangs. The different sequence preferences for ligation that result in ligation frequency and mismatch frequencies, and different fidelity profiles adds a further layer of refinement and efficiency of multiple fragment assembly. Modifications to standard ligase buffers that affect ligase activity such as polyethylene glycol are also described herein.

Tools and methods are provided to enable the assembly of larger number of fragments with greater fidelity in the assembled sequences and higher frequency of bacterial colonies transformed with destination vectors that include the assembled DNA or packaged viruses that infect lawns of bacteria. With the benefit of improvements, an intact T7 viral genome was assembled from 50 fragments. The newly synthesized virus was shown to produce viral plaques on a lawn of bacteria. The availability of the ligase data offers improvements in 24 fragment and 50 fragment assembly of at least 10%, 20%, 30%, 40% or 50% more colonies than would be possible otherwise.

The ability to assemble small numbers of polynucleotide fragments into a larger DNA (for example, less than 10 fragments) can be performed relatively efficiently without additional refinements. However, there are advantages associated with the assembly of larger numbers of smaller fragments (such as greater than 10 fragments or as many as 20 fragments or as many as 50 fragments or greater numbers such as up to 100 fragment or more) to create a similar size DNA. Such advantages include: less incidence of error occurring in small synthetic oligonucleotides than in large synthetic oligonucleotides, and the ease of stably maintaining bacterial clones that have plasmid inserts of a small size where these clones can be stored and used as needed for various assembly projects to make large DNA. This avoids problems of toxicity that may arise as larger fragments may be expressed in the bacterial clones and affect viability of the clones thereby reducing the quality of the library of stored fragments. Moreover, assembly reactions that involve large numbers of fragments offer the ability to create libraries of variant polynucleotides that may prove useful for vaccine development, car-T therapy and antibiotic development using phage as outlined in FIGS. 15 and 16 and in the examples.

A Novel Type IIS Restriction Endonuclease—PaqCI

PaqCI is characterized by a protein having at least 80% sequence identity to SEQ. ID NO: 1. PaqCI as used herein is intended to encompass variants that have at least 90%, at least 92%, at least 95%, at least 99% sequence identity to SEQ ID NO: 1. PaqCI relies on multiple subunits to interact with two recognition sites in order to cleave a single target site on each strand of the DNA duplex.

```
PaqCl sequence, 510 aa (SEQ ID NO: 1):
MPYDHNAEADFAASEVARMLVADPGLCYDAASLPASISASASYEPSAA

GWPKADGLVSVLEGGTSTQRAIALEYKRPQEGIHGLLTAIGQAHGYLH

KGYSGAAIVIPGRYSSHPTPAEYVRDVLNAISGSRAIAVFSYSPPDTT

SPTPFAGRIQCVRPLVFDAGRVHLRPANQGPKTQWVHMREGSTTRDAF

FRFLQVAKRLSADPTAPRPTLRSELVAAIGRLAPGRDPIEYITNTADN

KFLTKVWQFFWLEWLATPAVLTPWKLEAGVYSAPGARTRILREDGTDF

SQLWEGRVNSLKETIAGMLNRGEISEAQGWEAFVGGISATGGGQDKQG

VRARAHSYREDIDSALAQLRWIEDDGLPTDQGYRFMTICERYGGANSR

AAIDYMGATLIQTGRYASFLHYINRLSERKFAENPLAYTKPGPGGMPV

FTEESYWEYLQDLETKLTDELRVMRKVSGRARPRVRTTFQVELTLLRN

YGFVSSTRHRLGVGIPIDWEQVVQALNVDL
```

The recognition sequence of PaqCI is (5'-CACCTGC-3'/3'-GCAGGTG-5') and it cuts asymmetrically 4-bases from the recognition sequence in the 3' direction and eight basses from the complement of the recognition sequence in the 5' direction resulting in a 4-base overhang (see FIG. 1C)

Also described herein is a PaqCI activator oligonucleotide that was found to improve the activity of PaqCI. The activator oligonucleotide is a synthetic self-complementary single strand oligonucleotide that is folded so as to comprises a double-stranded DNA region and a single stranded DNA loop, for example a hairpin structure. An advantage of a hairpin over two single strands includes more complete annealing since the two ends of the single synthesized DNA strand are at exactly the same concentration.

The double-stranded region of the activator oligonucleotide contains a binding (recognition) sequence for PaqCI and the oligonucleotide comprises unligatable 3' and 5' ends, and cannot be cleaved by PaqCI, meaning that the double stranded part of the oligonucleotide does not extend far enough beyond the recognition site to provide a cleavage site for PaqCI. The self-complementary oligonucleotide that comprises a double-stranded region and a loop is preferably less than 100 nucleotides in length and contains the recognition sequence (5'CACCTGC/3'GTGGACCG) for PaqCI and extends no more than 0-4 bases or 1-4 bases downstream from the 5' recognition sequence. One unnatural extension of a blocking moiety on each strand may be added so that that there are no correctly positioned phosphodiester bonds in a double-stranded region for the enzyme to cleave. Alternatively, the activator oligonucleotide may contain an uncleavable linkage. The 5' and 3' ends of the oligonucleotide may be flush or recessed by 1, 2, 3, 4, 5, 6, or more nucleotides, where either the 3' end or the 5' end can be recessed. The loop of the oligonucleotide is not critical and may be 4-20 nucleotides in some cases. The double-stranded region may be 10-50 base pairs in length, e.g., 10-30 base pairs in length e.g., 15-30 bases.

The activator oligonucleotide has unligatable 3' and 5' ends that cannot be ligated to another substrate (polynucleotide fragment or activator oligonucleotide) by T4 DNA ligase or other ligase in a T4 DNA ligation buffer or other suitable ligase buffer. Examples of unligatable 3' and 5' ends are; a 3' end that does not contain a 3' hydroxyl and a 5' end that does not contain a 5' phosphate; a 3' end that contains a 3' phosphate and a 5' end that contains a C3 spacer; or alternatively a ligation block at the 3' end such as a 3' dideoxy-C, 3' C3 Spacer (C3-OH), a C6 spacer or 3' Amino Linker (C6-NH2) and a ligation inhibiting modified base at the 5' end such as an inverted dideoxy thymine (invddT). Accordingly, ligation of the activators to each other or to the polynucleotide fragments is prevented.

A reaction mixture containing PaqCI also includes one or more activator oligonucleotides for adding to target double stranded DNA intended for cleavage.

It is within the scope of these embodiments to utilize a mixture of PaqCI and one or more variants of PaqCI in the same reaction mixture with one or more activator oligonucleotides. In certain embodiments, methods are provided that additionally include one or more ligases. In certain embodiments, PaqCI may be used in a mixture with other restriction endonucleases having different or the same specificities.

The amounts of PaqCI and activator have been optimized to fall within a range that produces substantially complete cleavage of DNA substrate by PaqCI but no star activity. The ratio of PaqCI to activator was found to be more significant for optimization of enzyme activity than the ratio of activator to the recognition site on the target oligonucleotides. Insufficient concentrations of activator relative to Pap resulted in incomplete cleavage of the target DNA and star activity. Too much activator resulted in incomplete cleavage. Without wishing to be limited by theory, it is believed that incomplete cleavage was the result of binding of PaqCI exclusively to activator molecules instead of target DNA.

The optimal amount of the activator for a certain amount of PaqCI may vary according to its intended use. Standard restriction digest with PaqCI that does not involve complex assembly reactions in the same tube can be achieved using 1 μl of the enzyme (10 U) and 1 μl of the activator (20 pmoles). In these reactions, once the DNA substrate has been cleaved, it does not readily reassemble.

However, when PaqCI is used in multi-fragment assembly methods, overhangs generated by endonuclease cleavage can sometimes be reannealed and ligated, reconstructing the original recognition site. In this dynamic situation, any one DNA cut site can require being cut more than once throughout the assembly reaction. Consequently, the endonuclease to activator ratio was modified according to the number of fragments in an assembly reaction Consequently, it was determined that 0.75 pmole to 9 pmole activator (15 nM-180 nM in a standard 50 ul reaction volume)/Unit of PaqCI endonuclease was preferable where below 0.75 pmole activator/Unit of PaqCI, some small amount of star activity could be observed while at 10 prole activator/Unit of PaqCI, a start of inhibiting activity could be observed. In certain embodiments, the range may be selected from any of 0.75 pmole to 9 prole activator/Unit PaqCI, 1 prole to 7.5 pmole activator/Unit PaqCI, 1 pmole to 5 prole activator/Unit PaqCI, 1.5 pmole to 7.5 prole activator/Unit PaqCI, 1.5 pmole to 5 pmole activator/Unit PaqCI, 1.5 pmole to 4 pmole activator/Unit PaqCI, 2 pmole to 5 pmole activator/Unit PaqCI or 2 pmole to 4 pmole activator/Unit PaqCI.

One unit is defined for this ratio as the amount of enzyme required to digest 1 µg of λ DNA in 1 hour at 37° C. in a total reaction volume of 50 ul in 1× rCutSmart™ Buffer (50 mM Potassium Acetate, 20 mM Tris-acetate, 10 mM Magnesium Acetate, 100 µg/ml Recombinant Albumin (pH 7.9 @ 25° C.). The unit definition and description of buffer is not intended to be limiting but rather to serve as a guideline for developing the appropriate ratios of activator/PaqCI. Other buffers may be utilized depending on uses including selected ligases. For example, a commercial T4 DNA ligase buffer may be preferable for DNA fragment assembly methods. In one embodiment of an assembly method, a standard reaction volume is 50 ul and contains 1 pmole-8 pmole activator (20 nM to 160 nM) per unit of PaqCI endonuclease or 10 pmole-80 pmole (200 nM to 1600 nM) of activator for 10 units of enzyme. The DNA in the reaction mix was 1 ug of lambda DNA. In another embodiment, the activator concentration is at 20 uM with an enzyme concentration at 10 units/ul such that the optimum enzyme and activator in a 50 ul reaction resulting in a 1:1 ratio using 1 ul of each. For typical PaqCI reaction conditions this results in complete cutting of the DNA substrate recognition sites, even though the concentration of the substrate sites will vary depending on the DNA being cut. For ligation of multi-fragments for assembly of a polynucleotide, a lower ratio of activator to enzyme could be used (for example, 1:2, 1:3, 1:4, or 1:5) where the concentration of substrate sites is higher compared to typical reaction conditions. By lowering the activator amount an optimal ratio of enzyme to total recognition sites (substrate plus activator sites) can be maintained.

The recommended component concentration ranges described herein was also determined for multi-fragment assembly methods containing different numbers of insert clones resulting in simple to complex assemblies.

For example, PaqCI or a variant thereof may be combined with an activator, a ligase and a plurality of DNA substrates in a reaction mix. In one embodiment, the DNA substrates are contained in plasmids that contain PaqCI recognition sequences at the insertion sites with adjacent plasmid sequences that have been designed for ligation assembly of the substrates. During multi-fragment assembly, every insert and every destination plasmid has an assembly active DNA fragment flanked by two sites. The reaction mix may be incubated at a time and temperature suitable for endonuclease cleavage and ligation of fragments (for example at 37° C. and 60° C. for 30-60 ligation cycles where each cycle is 1-5 minutes depending on the number of fragments in the mix). The desired reaction product is a large DNA molecule formed from the plurality of DNA substrates. Different levels of complexity of fragment assembly calls for different levels of PaqCI and DNA ligase as described above. As assembly reactions increase in complexity, more units of enzyme are required for maximal performance; for example, using T4 DNA ligase, 2.5 to 20 U of PaqCI can be used with 200-800 U of the ligase with the upper range of 10-20 U of PaqCI and 400-800 of DNA ligase being preferred for assembly of 20 or more fragments.

PaqCI cuts to completion and does not have star activator when combined with activator (see FIG. 1D). It has greatly improved performance when compared with AarI (see FIGS. 1A and 1B).

In embodiment, kits are provided containing reagents in a mixture or in one or more containers, the reagents including PaqCI or variants thereof ("PaqCI") and activator molecules. The kits may further include a ligase. The kits may include the reagents in a reaction buffer or one or more of the reagents may be lyophilized and/or immobilized on a suitable substrate such as beads or a polymer matrix together or separately. The kit may additionally contain reaction buffer in a separate container for adding to the reagents.

Ligation Frequency and Fidelity for Various Ligases

Multi-fragment assembly can be achieved by combining PaqCI with a selected ligase to generate fragments with 4-base overhangs. The ordered assembly depends on the fidelity of annealing of the overhangs and the promiscuous nature of ligation by ligases of all annealed overhangs which in turn depends on the conditions of ligation including the number of fragments to form a scarless contiguous DNA. Embodiments of the invention establish the role of various ligases in intrinsic ligase preference versus ligation associated annealing.

T4 DNA ligase is the standard ligase for end ligations and large DNA assembly. However, it was unknown whether this ligase had sequence preferences that contributed to variable ligation profiles observed for end joined fragments having certain 4-base overhangs. Moreover, it was unknown how T4 DNA ligase compared in this respect to other ligases.

Methods have been developed here to analyze this question and use the results of the analysis to improve selection of overhangs to minimize bias, enhance yield assembled fragments and optimize fidelity as needed. A detailed analysis of the properties of 5 ligases is provided in the Figures and Examples (T4 DNA ligase, T3 DNA ligase, T7 DNA ligase, hLig3 DNA ligase and PBCV-1 DNA ligase). In addition, certain improvements are described in the Examples that were observed by adding PEG and/or Aprataxin to the ligation buffer.

In Example 1, the frequency of ligation, bias and fidelity profiles of DNA ligases T4 DNA Ligase, T3 DNA Ligase, T7 DNA Ligase, PBCV-1 DNA Ligase, and hLig3 were determined using a library of end-joining hairpin DNA substrates containing degenerate 5'-four-base overhang ends. The ligation products of these libraries were analyzed by sequencing. The number of reads for each overhang provided a value for ligation efficiency; the sequence bias for each ligase was inferred from the relative frequency of each overhang appearing across all ligation products.

The hairpin substrate in the assay presents a complex equilibrium system that mimics the actual assembly of multi-fragments wherein ligation requires a ligase finding complementary ends of fragments. A rapid conversion to ligated product would be predicted if there were only two Watson-Crick binding partners in the reaction. The assay method provided a depth of information not available by separately examining individual overhangs and permitted a more rapid appraisal of fidelity and bias than would have been possible through testing each pairing in parallel. The raw data for the frequency of each ligation of every complementary 4-base overhang is presented in a heat map (matrix) in FIG. 3Ai/3Aii-FIG. 3Hi/3Hii for different ligases under the same assay conditions. This data showed that library ligation frequency and fidelity varied significantly among ligases tested. T4 DNA ligase, T3 DNA ligase, and hLig3 all yielded greater than 55% ligation product. PBCV-1 ligase had a slightly lower yield (50%). T7 DNA ligase had by far the lowest yield, only reaching 20% ligation product.

Varying overall degrees of bias, as well as intrinsically different preferred sequences between ligases were observed (see FIG. 3Ai/3Aii-FIG. 3Hi/3Hii). T7 DNA ligase showed the highest degree of sequence bias preferring to ligate perfect matches of bases in the 4-base overhangs. All other ligases examined had a much tighter distribution of ligation frequencies, but with differences in how tightly the data points are clustered around the average (see FIG. 4A). Both T4 DNA ligase and hLig3 showed the least amount of bias with the range of values more than two-fold smaller compared to T7 DNA ligase. PBCV-1 and T3 had a similar average ligation frequency but a slightly larger range of observed ligation frequencies.

The ligases examined here showed extremes of fidelity with T7 DNA ligase displaying the highest fidelity (89% correct ligation products), while hLig3 had the lowest fidelity (56% correct ligation products). T4 DNA ligase displayed moderate fidelity (72% correct ligation products). T4 DNA ligase, T3 DNA ligase, PBCV-1 ligase and hLig3 had a broad range of fidelity for individual overhang sequences, with some overhangs having very few mismatch ligation events and others with frequent mismatch ligations (FIG. 4B). For many overhangs, even when presented with all possible partners, ligation products were almost exclusively with the Watson Crick partner. Where specific mismatch base pairs tolerated by each ligase occurred, these was more commonly at the 5' terminal nucleotide ('edge') rather than in the middle of the overhang ('middle'). Some frequent mismatches, notably G:T mismatches, were common among all tested ligases; however, there were also distinct mismatch pairings observed among the ligation products of each ligase.

For example, when T4 DNA ligase was presented with all possible ligation partners, several overhangs paired with their Watson Crick partner in over 90% of ligation products (e.g. AAAA; AAGA, ACAA, GAAA). Other overhangs ligated to a partner containing at least one mismatch; several overhangs paired with a mismatch-containing partner more than 60% of the time (e.g. GGCG, GGCC, GGGC, GGGG).

Although for certain multi-fragment assemblies, it may be desirable to maximize the Watson-Crick matches to provide perfectly correct sequences, in other circumstances it may be desirable to introduce errors in fragment assembly to establish variable large DNAs. For example, hlig3 may be selected to increase the chance of a fragment in a set of fragments, ligating to another fragment in an incorrect order because of the promiscuity of the ligase. Alternatively if maximum fidelity of assembly is desired and frequency of ligation is not as important, T7 DNA ligase may be the enzyme of choice. However as shown below, additives to the ligation buffer such as PEG may somewhat enhance frequency of ligation without significant loss of fidelity so that T7 DNA ligase might be the ligase of choice for a 20+ fragment assembly workflow where otherwise this ligase might be less desirable.

Addition of Ligation Enhancer PEG Reduces Ligation Bias but Also Reduces Fidelity Polyethylene glycol (PEG) (Millipore Sigma, Burlington, MA) may also be used to enhance ligation. The examples show that PEG having a molecular weight in the range of 600-6000 enhances DNA assemble. For example, PEG MW may be selected from 500, 600, 800, 1000, 1500, 2000, 2500, 3000, 3500, 4000, 4500, 5000, 5500, 6000, 6500, 7000, 7500, 8000, 8500, 9000 and 10,000. Example 4 shows results with PEG 600, PEG 3350 and PEG 6000 at 6.8% w/v.

The addition of PEG increased the overall library yield for both T4 DNA ligase and T7 DNA ligase (from 61% to 73% and from 20% to 45%, respectively) and there was a slight decrease in the yield of hLig3 (from 77% to 72%). The addition of PEG moderately decreased the overall fidelity of the multiplex ligation reaction for T4 DNA ligase from 72% correct ligation events in the absence of PEG to 67% in the presence of PEG (see Table 2, FIG. 5A-5E). The addition of PEG decreased fidelity by the same amount regardless of GC content, except for overhangs with 100% GC content which did not see a change in average fidelity. The fidelity of T7 DNA ligase also significantly decreased from 89% to 78% in the presence of PEG and the overall ligation fidelity of hLig3 had a small decrease upon addition of PEG (56% and 51%, respectively) (Table 2). Notably, the addition of PEG did not change the identity of the specific mismatches tolerated for any of the ligases tested. Addition of PEG also produced modest changes in the bias of T4 DNA ligase. A boost in efficiency for the ligation of overhangs with less than 50% GC content was observed. Interestingly, the extreme bias of T7 DNA ligase was reduced by the addition of PEG, and overhangs which were previously not ligated at all had significant product accumulation (FIG. 5A-5E). The results obtained from PEG of different sizes is provided in Table 6.

Typical reaction conditions and additives may impact different DNA ligases and provide insight on modifications that might improve particular application outcomes. For example, for applications such as cloning or adaptor ligation, the boost in ligation product yield for from adding PEG will likely outweigh the moderate loss of fidelity for T4 DNA Ligase and T7 DNA Ligase. However, for applications involving highly complex multi-fragment assembly, the loss of fidelity observed when adding PEG may require more consideration of the particular overhangs used to limit potential mismatch ligation among a particular overhang set. The addition of PEG makes T7 DNA ligase a more attractive candidate for large multi-fragment assemblies. The observed gains in efficiency for additional overhangs expands the pool of efficient potential overhang sequences, while the small loss in fidelity is tolerable due to the high overall fidelity of this enzyme.

Data Optimized Assembly Design.

Ligase Fidelity Viewer, GetSet and SplitSet tools are described here and in WO 2020/0181768 that provide data optimized assemble design that greatly improve the success of ordered assemble of fragments. These tools rely on menu choices to assist the user. The experimental conditions described below each result from a 256×256 data matrix of ligation frequency and fidelity. The computer tool can utilize this data to generate optimized overhangs for the desired number of fragments and type of overhang.

Selection of a set of overhangs suitable for assembling a selected number of polynucleotide fragments into a target polynucleotide can be achieved by means of these tools to test and arrange in suitable order, useful overhangs that cannot be achieved by a mental act. In one embodiment, the identification of suitable overhangs include one or more steps. Certain rules have been applied that include no palindromic overhangs, no duplicate overhangs, no overhangs with 3-bases in a row e.g., ACCA and ACCG; no more than 2-bases in the same position e.g., (ACGC and ATGG) and avoidance of overhangs with 0% GC overhangs and 100% GC overhangs (Nilsson et al. Nucleic Acids Res., 10, 1425-1437 (1982); Goffin et al. Nucleic Acids Res., 15, 8755-8771 (1987); and Wu et al. Gene, 76, 245-254 (1989)). However the optimized data sets determined by data optimized assembly design exemplified herein have no such rule based limitations providing more flexibility in the choice of overhangs. For example, temperature plays a role in the overall degree of annealing of overhangs according to AT and GC content. The preferred locations of the A, T, G or C bases in the overhang has been found to vary depending on the ligase used. Very few mismatches occur within the 4-bases overhang but different preferences for various ligase are found for bases at either edge of the overhang.

Embodiments describe how to obtain an optimized data set by profiling end-joining hybridization and ligation fidelity and bias to predict highly accurate sets of connections for ligation-based DNA assembly methods. This presents a significant improvement over the prior art rules that restrict the user to a limited number of 4-base overhangs, which is particularly constraining when sequences may not be chosen arbitrarily (e.g., when assemblies must break within coding sequences). Application of the ligation fidelity profile permitted an informed choice of junctions and enabled a highly flexible assembly design using more than 20 fragments in a single reaction.

In one embodiment, the computer design tool provides a selection of overhangs after the user inputs various requests. For example, the computer tool receives selection or input of experimental conditions under which the assembly reaction is expected to occur (see for example Table 1). The experimental conditions will change the choice of ligation frequency tables and individual overhang ligation fidelity determinations accessed by the computer.

The computer tool will also receive numbers, for example: (i) a desired number of overhangs for an assembly reaction; (ii) a length of the overhangs; (iii) the nucleotide sequence of the assembly; (iv) the set of intervals in which the nucleotide sequence of (iii) can be cleaved, causing the method to be executed and then receiving as output, an identified set of overhangs and/or receiving a set of fragments for the assembly, where the ends of the fragments are defined by the identified set of overhangs, depending on which information is input into the interface.

This method may further include receiving instructions regarding the ligation conditions for ligating the set of overhangs or fragments containing the same. Ligation conditions may include one or more of a desired ligase, buffer conditions such as salt concentration, a temperature, temperature range and/or thermocycling times and temperature (which may be used for cleavage and ligation) and restriction endonuclease if used for generating overhangs. Where ligation conditions (in addition to the desired number of overhangs for an assembly reaction and the length of the overhangs) are received in the interface, the overall fidelity scores are calculated for the overhangs in ligations that were performed in the specified ligation conditions. Hence a ligation frequency table that corresponds to the specified conditions may be selected from multiple ligation frequency tables, each for a different ligation condition. After the ligation frequency table is selected, then the ligation fidelity scores can be calculated using data in that table.

In some embodiments, the number of overhangs may be in the region of 5-200, e.g., 10-100, e.g. 10-50, although the number of overhangs can be outside of these ranges in some circumstances. The length of the overhangs may be 2, 3, 4 or 5 nucleotides, where the length of the overhangs is limited only by the choice of restriction endonuclease or other means for generating the overhang and the frequency and fidelity of possible ligation reactions. The choice regarding the preferred length of overhang may be subject to the number of possible overhangs for any combination of nucleotides in the overhang where this number should exceed the number of fragments to be joined. After the desired number of overhangs for an assembly reaction and the length of the overhangs have been received, the computer provides a set of overhangs from an overhang table, of the selected length (e.g., 2, 3, 4 or 5-bases). For example, if a user were to input, into the computer, 20 overhangs each 4-bases long, then the computer would output a set of 20 unique overhangs that did not include duplicates, complements, palindromes (e.g. GATC) or excluded sequences. GATC is an example of a palindromic sequence since its reverse complement is GATC. Palindromes should be avoided because any one fragment with palindromic ends could anneal to another identical molecule resulting in the disruption of ordered assembly. The interface may permit receiving a list of one or more overhangs that should be excluded or included. Overhangs that are excluded may be selected because of poor fidelity or frequency of ligation profiles or because the overhangs have been used elsewhere in a reaction. Included overhangs may be selected on the basis of experimental findings of their high fidelity and/or frequency values.

As would be apparent, the overhang ligation frequency table may be stored in computer memory and can include all possible overhangs of the desired length or a subset of the same. For example, for a 4-base overhang the overhang table may contain 256 4-base sequences for a 3-base overhang the overhang table may contain 64 3-base sequences. The overhangs may be selected in any particular order. For example, in some embodiments the overhangs may be selected randomly whereas in other embodiments the overhangs may be selected in a defined order.

Based on the user selection from the menu, the computer calculates a ligation fidelity score for each individual overhang and its complement in the set. For example, if there are 20 overhangs in the set, then there should be 20 ligation fidelity scores, where the ligation fidelity score of each individual overhang represents the frequency at which the individual overhang and its complement independently ligate to a perfectly complementary overhang relative to all overhangs in the set and their complements. For example, if a particular overhang and its complement ligate together with perfect complementarity 90% of the time relative to all overhangs in the set and their complements, then that overhang may have a calculated ligation fidelity score of 0.9. If a particular overhang and its complement ligate 95% of the time, then the discrepancy suggests a calculatable rate of ligatable mismatches. These values result from the ligation fidelity/frequency tables described obtained by methods described herein where each entry consists of individual experimentally-defined measurements of the number of ligation events that factor in different experimental conditions.

Ligation Conditions

Ligation conditions can be selected using a drop-down menu, where the ligase options laid out in the drop-down menu include different ligation frequency tables. Examples of experimental conditions that were found to affect ligation efficiency, fidelity and yield to which selection of ligase is added affect experimentally determined values for frequency and fidelity of overhang ligation for ordered assembly of fragments.

Temperature conditions for ligation including static temperatures and cycling between high and low temperatures using drop-down or touch-down cycling. These terms are explained in Example 2:

(a) Number of fragments for ordered assembly;
(b) Length of overhang;
(c) Time of incubation of the restriction endonuclease/ ligation reaction;
(d) Types of restriction endonuclease and ligase;
(e) Buffer types including salt concentrations;
(f) Cofactors such as crowding agents, repair enzymes and/or deadenylases (also see Tables 4 and 5);
(g) Choice of ligase;
(h) Acceptable ligase bias for or against certain 4-base sequences, tolerance of mismatches and fidelity profiles;
(i) Unacceptable ligase bias for or against certain 4-base sequences, tolerance of mismatches and fidelity profiles;

In one embodiment, a pull down menu for experimental conditions in the user interface for Ligation Fidelity Viewer, GetSet and SplitSet in FIGS. 9B-9D are shown in Table 1.

TABLE 1

T4 DNA Ligase, 25° C., 1 h incubation (4-base substrate) BsaI-HFv2
T4 DNA Ligase, 25° C., 18 h incubation (4-base substrate) BsaI-HFv2
T4 DNA Ligase, 37° C., 1 h incubation (4-base substrate) BsaI-HFv2
T4 DNA Ligase, 37° C., 18 h incubation (4-base substrate) BsaI-HFv2
T7 DNA Ligase, 25° C., 18 h incubation (4-base substrate) BsaI-HFv2
T7 DNA Ligase, 37° C., 18 h incubation (4-base substrate) BsaI-HFv2
T7 DNA Ligase, 25° C., 1 h incubation (4-base substrate) BsaI-HFv2
T3 DNA Ligase, 25° C., 1 h incubation (4-base substrate) BsaI-HFv2
Hlig3 DNA Ligase, 25° C., 1 h incubation (4-base substrate) BsaI-HFv2
PBCV-1 DNA Ligase, 25° C., 1 h incubation (4-base substrate) BsaI-HFv2
T4 DNA ligase BsaI-HFv2 37-16 cycling
T4 DNA ligase BsaI-HFv2 37 static
T4 DNA ligase BsmBI-v2 42-16 cycling
T4 DNA ligase BsaI-HFv2, 1x NEBridge Ligase Master mix (MM), 37-16 cycling
PaqCI, 1x T4 DNA Ligase buffer, 37-16 cycling
PaqCI, 1x NEBridge Ligase MM, 37-16 cycling
BsmBI-v2, 1x NEBridge Ligase MM 42-16 cycling
BbsI-HF, 1x NEBridge Ligase MM, 37-16 cycling Each entry had a 256×256 data set entered into the data tool for integration into the calculation of optimum overhangs. Example 1 describes in detail how the data was collected for a comparative study of 5 ligases.

A ligation frequency table for a 4-base overhang should have an experimental value for each of all possible combinations of overhangs, i.e., 256×256/2 datapoints, each value indicating the frequency of ligation of two overhangs under the defined experimental conditions. Details for how this data can be obtained is described in Example 1 as well as in Potapov, V. et al. (2018), ACS Synth. Biol., vol 7, p 2665-2674; Potapov et al. Nucleic Acid Res 2018, 46 e79; Potapov et al. (2018) BioRxiv; Pryor, J. M. et al. (2020) PLoS One, e8592; Pryor, J. M. et al. (2020) BioRxiv, e4019. The ligation fidelity score for an individual overhang can be calculated as the number of ligation events that occur between the individual overhang and its complement relative to the total number of ligation events that occur between (i) the individual overhang and all of the overhangs in the set and their complements; and (ii) the complement of the individual overhang and all of the overhangs in the set and their complements.

The overall fidelity score for the set of overhangs can then be generated based on the calculated ligation fidelity score for each of the individual overhangs, as output above. In some embodiments, the individual ligation fidelity score may be multiplied together to obtain the overall fidelity score. For example, if there are 20 overhangs that each have a fidelity of 0.950, then the overall fidelity score for that set of overhangs may be 0.36 (i.e., $0.95^{20}$). In some embodiments, this calculation may, in addition, weight overhangs by how efficient an overhang is at ligating to its complement. For example, in some cases, two overhangs may have equal fidelities, but one ligates to its complement more efficiently than the other under the conditions used. In this case, the overhang that ligates with a higher efficiency may have a higher weight than the other. As such, in some embodiments, the overall fidelity score may be calculated using (i) the calculated ligation fidelity score for each of the individual overhangs and (ii) the yield that each of the individual overhangs ligates to a perfectly complementary overhang.

After an overall fidelity score for the selected set of overhangs has been calculated, the process may be repeated for another set of overhangs to calculate a plurality of overall fidelity scores, each for a different set of overhangs. In this step the sets of overhangs selected in the iterated steps are different from one another (and different from the first set of overhangs). Again, in the iterated steps the selection may be random or in a defined order. In some embodiments, these steps may be iterated using a Monte Carlo simulation. In this method, at least 100, at least 1,000 or at least 10,000 overall fidelity scores may be generated, each for a different set of overhangs. This part of the method repeated until an overall fidelity score has been assigned to all possible combinations of overhangs or until one or more overhangs have been identified that overall fidelity score that is above a threshold.

After the overall fidelity scores have been calculated, then the method may comprise identifying the set of overhangs that has a suitable overall fidelity score (Examples of sets of overhangs are provided in Table 7 and Example 5). In some embodiments, the identified set of overhangs may have an overall fidelity score that is in the top 50%, top 20%, top 10% or top 5% of overall fidelity scores. In some embodiments, the identified set of overhangs may have the highest overall fidelity score or a score that is in the top 10% or top 5% highest fidelity scores. The selected set of overhangs may be output from the computer onto, e.g., a display (see Example 5 and FIGS. 9B-9D).

In further embodiments, the method may comprise a user inputting into an interface, one or more of the following: (i) the desired number of overhangs for an assembly reaction; (ii) the length of the overhangs; optionally, (iii) the nucleotide sequence of the assembly; (iv) the set of intervals in which the nucleotide sequence of (iii) can be cleaved, causing the method to be executed and then receiving as output, an identified set of overhangs and/or receiving a set of fragments for the assembly, where the ends of the fragments are defined by the identified set of overhangs, depending on which information is input into the interface. This method may further include receiving instructions regarding the ligation conditions for ligating the set of overhangs or fragments containing the same, and, optionally, thermocycling conditions for producing the fragments and ligating them together. In these embodiments, the method may comprise making a set of double stranded nucleic acids that have a set of overhangs that has an overall ligation score that is at or above a threshold, and their complements, and then ligating the fragments together in a single reaction to produce an assembly, wherein in the reaction the overhangs determine the order of the fragments in the assembly. The ligating may be done by overhang-directed ligation, which will be explained in greater detail above and/or below. As would be apparent the method may further comprise receiving selected experimental conditions for ligation.

Implementation of the above embodiments are illustrated by the Ligation Fidelity Viewer, GetSet and SplitSet that have been described in detail in WO 2020/081768. The user interface for each of these applications is provided in FIGS. 9A-9D. The ligase data provided in the examples is an additional feature of the experimental conditions as discussed above that enables refinement of the optimized set of overhangs. This is particularly useful for large sets of overhangs with corresponding large sets of fragments for ordered assembly.

In GetSet (see FIG. 9C) the overhang length is selected, the total number of overhangs is entered, those overhangs that are required are entered and excluded overhangs can also be added and experimental conditions can be selected including the use of PaqCI and a selection of ligases. GetSet will then provide a set of overhangs best suited for the ligation conditions specified.

In SplitSet, a first step may include receiving a nucleotide sequence of an intended assembly and a set of intervals (e.g., at least 5, at least 10, at least 20 or at least 30, up to 50 or more intervals) in which the nucleotide sequence can be cleaved (in addition to the desired number of overhangs for an assembly reaction and the length of the overhangs). The input sequence may be, for example, any sequence that is at least 500 bases in length, although sequences as short as 25 nucleotides could be selected providing a Type IIS restriction endonuclease recognition sequence is present at the beginning and end of that interval. For example, the method may include receiving a sequence and multiple sets of beginning and end coordinates, where each set of beginning and end coordinates defines an interval in which the sequence can be cleaved. In these circumstances, only overhangs that are in the intervals may be selected from the overhang table such that, together, each interval is represented by a selected overhang. A non-redundant set of sub-sequences are then identified in the intervals that are the same length as the received overhang length. These sub-sequences may be stored as the overhang table itself or only sequences from the non-redundant set of sub-sequences will be selected from an overhang table (see Tables 8 and 9). The intervals may be input into the computer by a user, e.g., by inputting the intervals into an interface (see FIG. 9D). Alternatively, a user may input a sequence and specify how many fragments are desired. In these embodiments, an algorithm may determine approximate positions at which the input sequence may be split to produce the desired number of fragments, and then identify intervals (which may be, e.g., 10-50 or 10-100 nucleotides in length) that contain the approximate positions. The intervals may be processed as described above. In these embodiments, the method may further comprise splitting the nucleotide sequence of the assembly at the identified overhangs, thereby producing a set of fragments of the assembly, where the ends of the fragments are defined by the identified overhangs. The SplitSet interface is shown in FIG. 9D where the desired overhang length is provided by selecting an item in the menu. Ligations conditions are then selected just as with the Ligation Fidelity Viewer, the nucleotide sequence is inputted, the number of fragments is entered. The computer will then provide the results for the optimized set of fragments for ordered assembly.

Embodiments are provided herein for enabling a user of a computer to review by means of a graphical representation, the ligation fidelity profile expected from a predetermined set of fragment overhangs under selected experimental conditions. Each of these features can be modified by adjusting any of the parameters described herein to provide a revised graphical representation and to determine whether the change improved the ligation fidelity profile for the selected number of overhang sequences using the graphical representation of the deviation from perfect score obtained for the set of overhang sequences.

Other embodiments are provided herein for enabling a user of a computer to rapidly and efficiently obtain from the computer an optimized set of overhang sequences suited for assembling multiple nucleic acid fragments into a target polynucleotide. The optimization can rely on two or more databases of ligation fidelity and ligation efficiency (frequency) values for all possible overhang sequences for a complete set of all possible sequence combinations of overhangs having a single length under selected experimental conditions. A first database may be the product of analysis of annealed overhangs where an example of an assay is provided in FIG. 2A-2C and Example 1. A second database may be derived using the same assay to provide data on frequency and fidelity of ligation by different ligases that recognize different 4-base overhangs and have different or similar biases. The complete set of overhangs may include overhangs of different sizes. The nucleic acids include DNA, RNA or DNA/RNA hybrids or chimera. While DNA may be specifically mentioned in the description, examples and claims for convenience, embodiments herein are not limited to DNA but may be applied to any type of nucleic acid as described above.

Factors for determining an appropriate length of overhangs include: how many fragments are desired to be joined where the longer the overhang, the larger the set of possible combinations. This enables more fragments, each with a unique overhang complementary to its adjacent fragment overhang, to be joined to form a target polynucleotide. Other factors include the efficiency of melting/annealing where shorter overhangs melt and anneal faster and longer overhangs require higher melting temperatures. Ligation efficiency is another factor where longer overhangs may ligate more efficiently than shorter overhangs. Ligation efficiency also depends on the characteristics of the nucleotides singly or together in the overhang where some sequences are more efficiently hybridized and/or ligated to form a junction than others, have reduced bias and do not favor or induce mismatches.

In one embodiment, the output from the system instructs the user which restriction endonucleases should be used to cleave the nucleic acid to generate overhangs having sequences that have been optimized for ligation fidelity or selected for a chosen ligation fidelity. However other cleavage enzyme systems can be used such as uracil-specific excision reagent (USER®, New England Biolabs, Ipswich, MA), argonautes, clustered regularly interspaced short palindromic repeats (CRISPR) or other cleavage enzymes can be used to generate overhangs.

The experimental conditions discussed above are offered by menu from the computer interface to the user and then selected by the user or selected by the computer that has computed all the various parameters for the assembly and provides the best conditions for efficient joining all the fragments in a set correctly. The use of a Type IIS restriction enzyme enables the precise selection of a site where the DNA will be broken and enables exclusion of the restriction enzyme recognition sequence from the final construct (thus enabling seamless one-tube assembly reactions) or certain types of nucleic acid assembly, for example for gene coding regions, scarless junctions which do not alter the DNA sequence are important. In other applications, for example, cistron formation, additional or altered nucleotides that may remain from an assembly reaction may not interfere with the gene expression of the target nucleic acid. In one embodiment; the endonucleases suitable for use in generating overhangs and scarless junctions include:

2-base overhang generators (e.g. BtsI and isoschizomers thereof, AcuI and isoschizomers thereof),
3-base overhang generators (e.g., SapI and isoschizomers thereof and BspQI and isoschizomers thereof (both 7-base recognition)),
4-base overhang generators (e.g., BsaI-HFv2 and isoschizomers thereof (6-base recognition), BbsI and isoschizomers thereof (6-base recognition), BsmBI and isoschizomers thereof (6-base recognition), PaqCI (7-base recognition) and
5-base overhang generators (e.g., HgaI and isoschizomers thereof with a 5-base recognition site).

Other restriction endonucleases as described in the New England Biolabs 2017/2018 catalog and isoschizomers thereof may be used for those assembly reactions that are not required to be scarless.

2-base overhangs generate a 16×16 matrix data table, 3-base overhangs generate 64×64 matrix data table, 4-base overhangs generate 256×256 matrix data table, 5-base overhangs generate a 1024×1024 matrix data table, 6-base overhangs generate a 4096×4096 matrix data table. The upper limit of overhang length using a Type IIS restriction endonuclease may be 5, 6, 7 or 8-bases in length. For a nicking agent such as USER, the number of bases in an overhang may be as much as the user desires based on the positioning of a uracil. The optimized sets of Watson crick pair overhangs include overhang pairs that can ligate with their exact complementary partner efficiently, are not palindromes, and are unique within the set. Other overhang pairs are acceptable as long as preferably no individual overhang forms a ligation product with an overhang partner containing one or more mismatches but preferably no more than one mismatch. The highest fidelity set of overhangs with good ligation fidelity can be provided by the computer for any chosen number of junctions (such as 10 junctions, 12 junctions, 15 junctions, 20 junctions etc.). The greater the number of junctions the lower the mean maximal ligation fidelity for the set of overhang pairs.

In some embodiments, overhangs are created using alternate enzymes such as nicking agents for example, USER (also see for example U.S. Pat. No. 7,435,572), or EndoMS suitable for creating overhangs in DNA fragments; and argonautes and Cas cleavage enzymes suitable for overhangs in DNA and RNA, where these enzymes utilize guide DNAs or RNAs.

Embodiments of the methods permits the user to receive a computational output that provides optimized sets of overhangs based on a measure of the net effect of cutting, melting, annealing, and ligation for a particular combination of cleaving enzyme and one or more ligases under a given set of cycling conditions where some or all of these features are provided by the user. The output can then provide a relative ligation efficiency and/or ligation fidelity value for every overhang pairing.

The computational output may additionally provide for the user an optimized protocol for performing an assembly to obtain a desired overall ligation fidelity detailing at least one of temperature, time for hybridization, cycling conditions for ligation, and buffer.

The computational output may include a graphical output of features that include one or more of the following: (1) the entire assembled sequence with the junction sites highlighted; (2) a map of input fragments with individual cut sites indicated on the fragment where the set of cut sites have been determined computationally to yield the optimal set of overhangs for fragment assembly to form the desired product; (3) a matrix of ligation fidelity of the selected overhangs under the user specified conditions or the computer optimized experimental conditions; and (4) a set of primer sequencers that contain selected Type IIS restriction endonuclease recognition sequences and overhang sequences plus any additional target fragment sequences for directing automated oligonucleotide synthesis. The set of primer sequences can be forwarded electronically to a receiving location for instructing a DNA synthesis instrument to make such primers.

In one embodiment, the results for a user's chosen set of overhangs can be optimized by the user providing the preferred set of conditions to achieve efficient and accurate hybridization. Short linkers of arbitrary sequences are preferred for large numbers of fragments (e.g., ≥20). Multiple data sets can be accessed that provide overhang optima under different conditions. Such assays enable the user to select a set of enzymes and reaction conditions that would give the highest possible fidelity and efficiency for a selected set of overhangs.

In another embodiment, partial overhang pair reaction parameters and data sets could be selected by the user and partial overhang reaction parameters and optionally data sets could be selected by the computer to provide the optimal ligation efficiency and fidelity possible to create the desired number of ligated fragments. For example, 15 junction pairs might be required in total to join 16 fragments of double stranded nucleic acid fragments where 6 overhang pairs had been selected by the user and the remainder of overhangs are provided in a computer-generated output optionally with preferred experimental conditions including choice of ligase. The user could then be enabled to receive an additional optimized 9 overhang pairs with optional choice of reaction components such as restriction enzyme, ligase and optional choice of other reaction conditions including cycling time and temperature that would provide the highest ligation fidelity and efficiency possible for the 15-member final set.

In another embodiment, the user inputs into the computer, a gene, gene pathway, plasmid or chromosome sequence for dividing into fragments suitable for efficient assemble with high fidelity using an optimized set of overhangs. The user may specify the target nucleic acid and the desired number of fragments. The webtool or graphical interface provides the sequence for the desired number of fragments at the optimal junctions that satisfy the hybridization parameters of the associated overhangs that when ligated, form scarless junctions thus enabling to the user to make the target polynucleotide in the desired manner. If the user additional specifies the minimum acceptable fidelity, the sequence specification for the desired number of fragments may be altered and indeed the number of fragments provided to the user might change to provide the maximum number of sequences possible with junctions that provide the specified minimum acceptable fidelity.

In another embodiment, the user may provide the target sequence and additionally may specify some junctions to be included in the design of constituent fragments with predetermined overhangs, and some subset of reaction conditions (or all reaction conditions). The computer provides to the user, a list of overhangs for efficient ligation to supply the best additional junctions and/or reaction conditions.

The assembly proceeds at either a single temperature suitable for all types of enzyme activities used in a reaction (e.g., cleavage enzymes and ligation enzymes) or any number of cycling conditions varying between an optimal cutting/melting temperature and an optimal annealing/ligation temperature. Thus, overhangs are generated and sealed in one pot, and multi-fragments can be joined together in one experiment.

Implementation of Nucleic Acid Assembly Using a Computer Program and a General-Purpose Computer System The various components of the various systems described herein may be implemented as a computer program using general-purpose computer systems. Such a computer system typically includes a main unit connected to both an output device that displays information to a user and an input device that receives input from a user. The main unit generally includes a processor connected to a memory system via an interconnection mechanism. The input device and output device also are connected to the processor and memory system via the interconnection mechanism.

One or more output devices may be connected to the computer system. Example output devices include, but are not limited to, liquid crystal displays (LCD), plasma displays, cathode ray tubes, video projection systems and other video output devices, printers, devices for communicating over a low or high bandwidth network, including network interface devices, cable modems, and storage devices such as disk or tape. One or more input devices may be connected to the computer system. Example input devices include, but are not limited to, a keyboard, keypad, track ball, mouse, pen and tablet, touchscreen, camera, communication device, and data input devices. The invention is not limited to the particular input or output devices used in combination with the computer system or to those described herein.

The computer system may be a general-purpose computer system, which is programmable using a computer programming language, a scripting language or even assembly language. The computer system may also be specially programmed, special purpose hardware. In a general-purpose computer system, the processor is typically a commercially available processor. The general-purpose computer also typically has an operating system, which controls the execution of other computer programs and provides scheduling, debugging, input/output control, accounting, compilation, storage assignment, data management and memory management, and communication control and related services. The computer system may be connected to a local network and/or to a wide area network, such as the Internet. The connected network may transfer to and from the computer system program instructions for execution on the computer, media data such as video data, still image data, or audio data, metadata, review and approval information for a media composition, media annotations, and other data.

A memory system typically includes a computer readable medium. The medium may be volatile or nonvolatile, writeable or non-writeable, and/or rewriteable or not rewriteable. A memory system typically stores data in binary form. Such data may define an application program to be executed by the microprocessor, or information stored on the disk to be processed by the application program. The invention is not limited to a particular memory system. Time-based media may be stored on and input from magnetic, optical, or solid-state drives, which may include an array of local or network attached disks.

System such as those described herein may be implemented in software, hardware, firmware, or a combination of the three. The various elements of the systems, either individually or in combination may be implemented as one or more computer program products in which computer program instructions are stored on a computer readable medium for execution by a computer or transferred to a computer system via a connected local area or wide area network. Various steps of a process may be performed by a computer executing such computer program instructions. The computer system may be a multiprocessor computer system or may include multiple computers connected over a computer network. The components described herein may be separate modules of a computer program, or may be separate computer programs, which may be operable on separate computers. The data produced by these components may be stored in a memory storage system or transmitted between computer systems by means of various communication media such as carrier signals.

Uses of Polynucleotide Ordered Assemblies

The improved methods, compositions and kits may be used in a number of diagnostic and medical contexts. Some examples are given below.

Example 5 describes the use of multi-fragment assembly methods for component sequences of Coronaviruses that can be engineered into novel virion sequences transcription into RNA and testing as potential substrates for vaccine development. FIG. 14 and FIG. 15 show the improved multi-fragment assembly described herein for CarT-cell therapy and for designing phage antibiotics. These methods rely on making large arrays of 25-50 fragments in a one pot reaction. These arrays can then be used to target multiple genes in a single one pot reaction. Alternatively, a single gene could be targeted multiple times and/or in multiple locations to enhance the efficiency of editing via homology directed repair. Another application of arrays is to create or alter gene pathways for, for example, metabolic pathways. These metabolic pathways may then be controlled by dcas9 to bind those genes it is desirable to turn off. Biosensor arrays may be designed (using for example Cas 13), to sense a wide range of nucleic acids at once, for example in a multi-pathogen sensor system).

In the applications listed above, overall design rules provided by the computer and summarized in FIG. 9A-9D facilitate creation of the 25-50 fragment arrays almost instantly. Using the computer tool, it would be possible to create arrays of fragments having relatively poor fidelity (see hlig3). hlig 3 would facilitate creation of libraries in which the number of included gRNA template sequences was varied by controlled deletions via mismatch ligation.

For those arrays that utilize fragments that are small (for example 30-70 nucleotides), these can be readily synthesized by oligonucleotide foundries using the information from the computer tool for the overhangs that work best for the subsequent assembly that relies solely on ligation. The designer could select the optimal ligase and also the preferred overhang length for the optimal frequency of the correctly assembled fragments and the desired fidelity of the assembled fragments in a single step reaction.

All publications, patents, and patent applications mentioned in this specification are herein incorporated by reference to the same extent as if each individual publication, patent or patent application was specifically and individually indicated to be incorporated by reference including U.S. Provisional Application No. 63/125,530 filed, Dec. 15, 2020; U.S. Provisional Application No. 63/213,807, filed Jun. 23, 2021; and U.S. Provisional Application No. 63/213,859, filed Jun. 23, 2021.

EXAMPLES

Example 1: Differences in Frequency of Ligation for Different Ligases Caused by Different 4-Base Sequences All enzymes (excepting hLig3) and buffers were obtained from New England Biolabs (NEB, Ipswich, MA). T4 DNA ligase reaction buffer (1×) is: 50 mM Tris-HCl (pH 7.5), 10 mM $MgCl_2$, 1 mM ATP, 10 mM DTT. NEBNext® Quick Ligation reaction buffer (1×) is: 66 mM Iris pH 7.6 @25° C., 10 mM $MgCl_2$, 1 mM DTI, 1 mM ATP, 6% Polyethylene glycol (PEG 6000). NEBuffer 2 (1×) is: 10 mM Tris-HCl (pH 7.9), 50 mM NaCl, 10 mM $MgCl_2$, 1 mM DTT. CutSmart® Buffer (1×) is: 20 mM Tris-acetate (pH 7.9), 50 mM Potassium Acetate, 10 mM Magnesium Acetate, 100 μg/ml BSA. ThermoPol® buffer is: 20 mM Tris-HCl (pH 8.8), 10 mM $(NH_4)_2SO_4$, 10 mM KCl, 2 mM $MgSO_4$, 0.1% Triton-X-100. Standard Taq polymerase buffer is: 10 mM Tris-HCl (pH 8.3), 50 mM KCl, 1.5 mM $MgCl_2$. All column cleanup of oligonucleotides and ligated libraries was performed using Monarch® PCR & DNA Cleanup Kit columns (New England Biolabs, Ipswich, MA), following the Oligonucleotide Cleanup Protocol. Oligonucleotide purity and sizing was performed using an Agilent Bioanalyzer® 2100 (Agilent, Santa Clara CA), using a DNA 1000 assay, following the standard protocols.

The hLig3 beta gene was synthesized by Biomatik (Ontario, Canada) and subcloned into a pET28 plasmid in frame with an N-terminal $His_6$-tag. The construct was expressed in T7 Express lysY/I$^q$ E. coli cells (New England Biolabs, Ipswich, MA).

The substrate for the four-base overhang ligation fidelity assay was produced according to WO 2020/081768 and Potapov et al. (2018) ACS Synthetic Biology, 7, 2665-2674. Briefly, initial PAGE-purified substrate precursor oligonucleotide contained a 5'-terminal region, a randomized four-base region, a BsaI-HFv2 binding site, a constant region, an internal 6-base randomized region as a control for synthesis bias, and a region corresponding to the SMRT-bell sequencing adapter for Pacific Biosciences SMRT sequencing. The precursor oligonucleotide was extended as described previously and purified using the Monarch PCR & DNA Cleanup Kit. The extended DNA was cut using BsaI-HFv2 to generate a four-base overhang.

For each ligation reaction, substrate (100 nM) was combined with the DNA ligase (either T4 DNA ligase, T3 DNA ligase, T7 DNA ligase, PBCV-1 DNA ligase, or hLig3 at 1.75 μM final concentration) in 1× T4 DNA ligase buffer (or NEBNext® Quick Ligation reaction buffer for reactions noted as containing PEG) in a 50 μL total reaction volume and incubated for 1 hour at 25° C. Reactions were quenched with 2.5 μL of ligase reaction quench (500 mM EDTA+2.5% v/v Proteinase K) and the sample was heated to 37° C. for 30 minutes to allow for ligase cleavage by Proteinase K DNA. The reaction was then purified using the Monarch PCR & DNA Cleanup Kit and following the Oligonucleotide Cleanup protocol. Each ligation was performed in a minimum of duplicates, and the ligation yield was determined by Agilent Bioanalyzer (DNA 1000) with error reported as one standard deviation. The ligated library was treated with Exonuclease III (50 U) and Exonuclease VII (5 U) in a 50 μL volume in 1× Standard Taq Polymerase buffer incubated for 1 hour at 37° C. The library was purified using a Monarch PCR & DNA Cleanup Kit, oligonucleotide cleanup protocol, including a second wash step, and then quantified by Agilent Bioanalyzer (DNA 1000). Typical concentrations of final library were between 0.5 and 2 ng/μL. Two replicate experiments were conducted for each ligase. Sequencing and analysis of sequencing data were performed as previously described in WO 2020/081768 and Potapov et al (2018) Nucleic Acids Research, 46, e79-e79. Consensus sequences for the top and bottom strand of the ligation product were generated, and actual overhang sequences in each strand were extracted. Frequencies of all observed overhang pairs in ligation products were tabulated and used to derive results. Data from replicates were combined before subsequent analysis. Full results from each experiment are provided in FIG. 3Ai/3Aii-3Hi/3Hii.

To determine the fidelity and bias profiles of DNA ligases in end-joining, sequencing libraries were prepared by mixing each DNA ligase (T4 DNA Ligase, T3 DNA Ligase, T7 DNA Ligase, PBCV-1 DNA Ligase, and hLig3) with a DNA hairpin substrate containing degenerate 5'-four-base overhang ends, allowing for every possible sequence context to be observed in a single reaction for each ligase (Potapov, et al. (2018) Nucleic Acids Research, 46, e79-e79). The ligase was present in a large excess compared to the DNA substrate to permit rapid ligation of short cohesive ends. Following the ligation reaction, the libraries were sequenced using PacBio SMRT sequencing and a summary of multiplex ligation data for each ligase, including the total number of ligation events, percentage of correct (Watson-Crick) vs incorrect (mismatch) ligations, and yield of ligation product obtained is provided in Table 2.

TABLE 2

| Ligase | Total ligations | Correct ligations | Mismatch ligations | Overall fidelity, %$^a$ | Yi |
|---|---|---|---|---|---|
| T4 DNA ligase | 158,614 | 114,783 | 43,831 | 72.4 ± 0.7 | 61± |
| T7 DNA ligase | 169,136 | 150,212 | 18,924 | 88.8 ± 0.2 | 20± |
| Human DNA ligase 3 | 321,746 | 180,316 | 141,430 | 44.0 ± 1.5 | 77± |
| T3 DNA ligase | 172,210 | 102,085 | 70,125 | 59.2 ± 1.6 | 55± |
| PBCV-1 ligase | 113,923 | 87,936 | 25,987 | 77.2 ± 0.6 | 50± |
| T4 DNA ligase (PEG) | 209,092 | 139,890 | 69,202 | 66.9 ± 0.7 | 73± |

TABLE 2-continued

| Ligase | Total ligations | Correct ligations | Mismatch ligations | Overall fidelity, %[a] | Yi |
|---|---|---|---|---|---|
| T7 DNA ligase (PEG) | 66,562 | 51,884 | 14,678 | 77.9 ± 0.2 | 45± |
| Human DNA ligase 3 (PEG) | 187,912 | 94,525 | 93,387 | 49.7 ± 0.7 | 72± |

[a]The overall fidelity was computed by combining all replicate ligation fidelity data. The standard deviation was computed based on overall fidelities per replicate. Two replicates were collected for each ligase with exception of Human DNA ligase 3 with 4 replicates, and T3 DNA ligase with 3 replicates Since the population of DNA hairpin substrates presents a complex equilibrium system and ligation required finding compatible ends, competing annealing partners were expected to limit ligation yields by the presence of annealed pairings that ligate with poor efficiency. Library ligation yields at 1 hour varied significantly among ligases tested. T4 DNA ligase, T3 DNA ligase, and hLig3 all yielded greater than 55% ligation product, and are generally among the most efficient end-joining ligases. PBCV-1 ligase had a slightly lower yield (50%), reflecting its less robust end-joining activity. T7 DNA ligase had by far the lowest yield, only reaching 20% ligation product.

The multiplex ligation data revealed ligation sequence bias in the preferred overhang sequences. In the present assay, the number of reads for each overhang was a proxy for its ligation efficiency; the sequence bias for each ligase was inferred from the relative frequency of each overhang appearing across all ligation products. Varying overall degrees of bias, as well as intrinsically different preferred sequences were detected between ligases (FIG. 4A). T7 DNA ligase showed the highest degree of sequence bias. All other ligases examined had a much tighter distribution of ligation frequencies, but with differences in how tightly the data points are clustered around the average. Both T4 DNA ligase and hLig3 showed the least amount of bias with the range of values more than two-fold smaller compared to T7 DNA ligase. PBCV-1 and T3 had a similar average ligation frequency but a slightly larger range of observed ligation frequencies.

When the ligation frequencies of individual overhangs were analyzed, the specific sequences that were preferred or disfavored varied between the enzymes. For most ligases, a weak general trend disposing higher GC content overhangs to more efficient ligation was observed (FIG. 4A). The bias in favor of high GC pairings was seen for both Watson-Crick ligations and pairings containing at least one mismatch, indicating a preference for more strongly annealed sequences in both cases. T7 DNA ligase was most vulnerable to this bias, with low GC overhangs (0% or 25% GC content) rarely ligated and high GC content (>50%) accounting for 96% of ligated products. These data indicate that for T7 DNA ligase, end-joining ligation efficiency is dominated by the GC content of the overhang. T4 DNA ligase, T3 DNA ligase, and PBCV-1 showed a less pronounced, but still observable dependence on GC content. Conversely, hLig3 ligation appears to be independent of GC content. Clearly, however, GC content is not the only factor contributing to differences in bias. While experimental replicates of each individual enzyme are consistent in the preferred overhang sequences, comparison of sequence preferences between different DNA ligases reveals additional complex differences which cannot be easily described by GC content or other simple trends.

The majority of correctly base-paired ligation partners were observed in a similar overall frequency for T4 DNA ligase, T3 DNA ligase, PBCV-1 ligase, and hLig3. Overhangs with the sequence TNNA were ligated inefficiently and reduced compared to the median (Table 2). The corresponding ANNT overhangs, despite being expected to be present in the same proportion of the substrate pool, did not show a reduced incidence compared to the other overhangs in the set. The data showed that there was a fundamental inefficiency in ligation of overhang pairs which both contain a 5'-T. In addition, overhangs containing a 5'-C were ligated by hlig3 with greatly reduced efficiency (FIG. 3Aii).

The ligases examined here showed extremes of fidelity with T7 DNA ligase showed the highest fidelity (89% correct ligation products), while hLig3 had the lowest fidelity (56% correct ligation products). T4 DNA ligase displayed moderate fidelity (72% correct ligation products). T4 DNA ligase, T3 DNA ligase, PBCV-1 ligase and hLig3 had a broad range of fidelity for individual overhang sequences, with some overhangs having very few mismatch ligation events and others with frequent mismatch ligations (FIG. 4b). For many overhangs, even when presented with all possible partners, ligation products were almost exclusively with the Watson Crick partner. Where specific mismatch base pairs tolerated by each ligase occurred, these was more commonly at the 5' terminal nucleotide ('edge') rather than in the middle of the overhang ('middle'). Some frequent mismatches, notably G:T mismatches, were common among all tested ligases; however, there were also distinct mismatch pairings observed among the ligation products of each ligase.

For example, when T4 DNA ligase was presented with all possible ligation partners, several overhangs paired with their Watson Crick partner in over 90% of ligation products (e.g. AAAA, AAGA, ACAA, GAAA). Other overhangs ligated to a partner containing at least one mismatch; several overhangs paired with a mismatch-containing partner more than 60% of the time (e.g. GGCG, GGCC, GGGC, GGGG).

T4 DNA ligase with an overall fidelity of 72%, had a median fidelity of 90% for overhangs with 0% GC content and decreases in average fidelity with each incremental increase in GC content, ultimately falling to 52% fidelity for overhangs with 100% GC content (FIG. 5A). Of the overall 28% of all ligation products containing a mismatch, 98% of these had only a single mismatch. Mismatch ligation at the edge position (N1) of the 4-base overhang were dominated by G:T and T:G mismatches, accounting for 65% of all mismatch ligations at the edge. The presence of a mismatch at middle positions (N2 and N3) of the overhang were less tolerated by T4 DNA ligase but were still dominated by G:T mismatches.

In contrast, hLig3, showed a broad range of ligation fidelity. Most overhangs ligated with <50% fidelity, and several overhangs (TAAG, AATA, TTAC, CCAA) ligated with >80% fidelity. The influence of GC content was weaker for hLig3, which had an average fidelity of 72% on overhangs with 0% GC content and an average fidelity of 32% for overhangs with 100% GC content (FIG. 5C). More than half of ligation products (56%) contain mismatch base pairs. hLig3 has a significant accumulation of mismatch products with more than a single base pair mismatch, and 8% of ligation products contain 2 mismatches. Of these double mismatches, the large majority (97%) involved at least one mismatch in the edge position and typically include at least one G:T mismatch. In addition, while G:T and T:G mismatches were well tolerated, hLig3, T3 DNA ligase, and PBCV-1 ligase are also more permissive of purine:purine mismatches at both the edge and middle positions, with G:A and G:G mismatches ligated almost as frequently as G:T mismatches.

In contrast, T7 DNA ligase had a tighter range of ligation fidelity, with only a handful of overhangs that ligated with less than 80% fidelity. T7 DNA ligase showed over 85% average fidelity regardless of GC content. T7 DNA ligase has an overall lower tolerance for mismatch ligation, and only 12% of ligation products contain a mismatch. Similar to T4 DNA ligase, single base pair mismatches account for nearly all (98%) T7 DNA ligase mismatch ligation products and the predominate mismatches are G:T and T:G at the edge position and G:T in the middle position of the 4-base sequence.

Example 2: Bioinformatic Tool for Designing Golden Gate Assemblies

The computer design tool for determining overhangs to optimize ligation fidelity in FIG. 9A has three components—the Ligase fidelity viewer (see FIG. 9B), the GetSet viewer (see FIG. 9C) and the SplitSet interfaces (see FIG. 9D) that together form the ligation fidelity tool (see for example WO 2020/081768). All three computer design tools have relied on a single ligase (T4 DNA ligase). The data obtained here add to these three tools by providing a choice of preferences under the menu of ligation conditions. A ligase can be selected having different base sequence preferences that affect the choice of overhangs. The benefit of this additional data will improve the accuracy of the tools for ordered assembly of multi-fragments. The data is obtained from 4-base overhangs but can be readily repeated for 2-base, 3-base and 5-base overhangs The data also provides the user with a refined estimate of assembly fidelity for a given set of user-supplied overhangs and identifies problematic overhang pairings with a high potential for mismatch ligation if this is undesirable.

The GetSet tool allows users to generate overhang sets with maximum assembly fidelity using automated overhang selection. GetSet returns a high-fidelity overhang set matching input criteria of number of overhangs, length of overhangs and ligation conditions. Users can specify overhang sequences that must be included or excluded from the results. Importantly, GetSet does not use pre-calculated results and instead identifies de novo high-fidelity overhang sets using a stochastic search algorithm. Consequently, the stochastic search algorithm may return different recommended overhang sets from the same input criteria, meaning repeating a search can result in different junctions with similar predicted fidelities. We have therefore included a feature to save and recall prior GetSet search results. As an example, the GetSet tool was used to expand a standard overhang set used in plant synthetic biology; the set size could be increased from 11 overhangs to 20 overhangs with only marginal decrease in the predicted assembly fidelity from 81% to 80%.

The SplitSet tool designs high-fidelity assembly fragments from a desired target DNA sequence. To use this tool, users input a DNA sequence, the desired number of fragments, ligation conditions and approximate search windows for fusion sites (by default, the program chooses equally spaced search intervals). The SplitSet tool divides the input DNA sequence at the highest fidelity set of junctions within the parameters chosen. In addition, users can exclude specific fusion site sequences to ensure compatibility with pre-existing modular cloning systems or include fixed sites by setting a narrow search window to cover which site or sites must be used.

Additional features include, checking the fragments for the presence of any internal sites that might affect the choice of Type IIS restriction enzyme to direct an assembly, or alert the user to remove such internal sites via domestication. The program can also automatically generate a set of primers for the DNA fragments to add the flanking bases and recognition sites required either for amplicon generation of inserts to be directly used or for pre-doffing purposes. Finally, a report can be generated describing the full assembly with a color-coded graphical read out, your final assembly sequence, and descriptions of each junction between inserts.

Example 3: Aprataxin/5'Deadenylase and PEG in Golden Gate Assembly

In reactions described in the Tables below as specified, ordered assembly reactions consisted of precloned DNA fragments (3 nM each) or PCR fragments (3 nM each) and the indicated amount of restriction enzyme and ligase in T4 DNA ligase buffer or Blunt T/A ligase buffer (New England Biolabs, Ipswich, MA). Assembly reactions were incubated as described in Example 3, using one of the three different ligation protocols, followed by a 5 minute final incubation step at 60° C. then a final 4° C. hold prior to transformation. Transformations were performed using 2 μl of each assembly reaction added to 50 μl competent T7 Express chemically competent E. coli (New England Biolabs, Ipswich, MA) plated on the appropriate growth media, and incubated at 37° C. to form colonies.

The correctly assembled target polynucleotides coded for a cassette of the lac operon (about 5 kb) so that blue colonies of correctly assembled fragments could be distinguished from white colonies containing incorrect assemblies on IPTG/Xgal/Chloramphenicol plates.

Generally, it was found that the addition of a 5' Deadenylase enzyme or PEG 600-6000 increased the yield of correct assemblies.

TABLE 3

5' Deadenylase increases assembly yield >2-fold in the optimized concentration range (dropdown cycling)

| Test System | Cycling | Temps | Ligase | Type IIS | Overhang | Time | Additive | Yield | Efficiency | [Protein] |
|---|---|---|---|---|---|---|---|---|---|---|
| 24-Fragment | Drop-down | 37/16 | wt T4 | BsaI-HFv2 | 4 bp | 5 hr | No | 60 | 12 | 1000/30 |
| | Drop-down | 37/16 | wt T4 | BsaI-HFv2 | 4 bp | 5 hr | 5'De-ad (1.5 U) | 87 | 17.4 | 1000/30 |

TABLE 3-continued

5' Deadenylase increases assembly yield >2-fold in the optimized concentration range (dropdown cycling)

| Test System | Cycling | Temps | Ligase | Type IIS | Overhang | Time | Additive | Yield | Efficiency | [Protein] |
|---|---|---|---|---|---|---|---|---|---|---|
| | Drop-down | 37/16 | wt T4 | Bsal-HFv2 | 4 bp | 5 hr | 5'De-ad (5 U) | 109 | 21.8 | 1000/30 |
| | Drop-down | 37/16 | wt T4 | Bsal-HFv2 | 4 bp | 5 hr | 5'De-ad (25 U) | 154 | 30.8 | 1000/30 |

TABLE 4

5' Deadenylase increases assembly yield ~7-10-fold (Static cycling)

| Test System | Cycling | Temps | Ligase | Type IIS | Overhang | Time | Additive | Yield | Efficiency | [Protein] |
|---|---|---|---|---|---|---|---|---|---|---|
| 24-Fragment | Static | 37 | wt T4 | Bsal-HFv2 | 4 bp | 24 hr | No | 12 | 0.5 | 1000/30 |
| | Static | 37 | wt T4 | Bsal-HFv2 | 4 bp | 24 hr | 5'De-ad (25 U) | 94 | 3.91 | 1000/30 |
| | Static | 42 | Hi T4 | Bsal-HFv2 | 4 bp | 24 hr | No | 2 | 0.08 | 1000/30 |
| | Static | 42 | Hi T4 | Bsal-HFv2 | 4 bp | 24 hr | 5'De-ad (25 U) | 20 | 0.83 | 1000/30 |

TABLE 5

5' Deadenylase increases assembly yield >3-fold (Touch-down cycling)

| Test System | Cycling | Temps | Ligase | Type IIS | Overhang | Time | Additive | Yield | Efficiency | [Protein] |
|---|---|---|---|---|---|---|---|---|---|---|
| 52-Fragment | Touch-down | 50/16 | Hi T4 | Bsal-HFv2 | 4 bp | 24 hr | No | 1.1 | 0.05 | 1000/30 |
| | Touch-down | 50/16 | Hi T4 | Bsal-HFv2 | 4 bp | 24 hr | 5'De-ad (25 U) | 4.3 | 0.18 | 1000/30 |

TABLE 6

PEG 600-6000 increases assembly yield ~2-5-fold

| Test System | Cycling | Temps | Ligase | Type IIS | Overhang | Time | Additive | Yield | Efficiency | [Protein] |
|---|---|---|---|---|---|---|---|---|---|---|
| 24-Fragment | Drop-down | 37/16 | wt T4 | Bbsl-HF | 4 bp | 10 hr | No | 296 | 29.6 | 1000/60 |
| | Drop-down | 37/16 | wt T4 | Bbsl-HF | 4 bp | 10 hr | PEG 600 (6.8%) | 557 | 55.7 | 1000/60 |
| | Drop-down | 37/16 | wt T4 | Bbsl-HF | 4 bp | 10 hr | PEG 3350 (6.8%) | 1421 | 142.1 | 1000/60 |
| | Drop-down | 37/16 | wt T4 | Bbsl-HF | 4 bp | 10 hr | PEG 6000 (6.8%) | 1157 | 115.7 | 1000/60 |

Yield-Total amount of positive assemblies or plaques.
Fidelity-Yield/total assemblies or product (blue colonies/white colonies)
Efficiency-Yield/hour
[Protein]-Ligase concentration (units) and Type IIS concentration (units)/20 µl reaction
Accuracy-Number of correct end joining of fragments over number of total assemblies
Hi-T4-Thermostable T4 DNA ligase variant
5' Deadenylase and protein concentration in units (U)

Example 4: Testing the Effect of Reaction Temperature on Multi-Fragment Assembly Fidelity and Assembly of the Lac Operon Cassette from 52 Fragments Multi-fragment assembly that relies on a two enzyme mix (restriction endonuclease and ligase) typically utilizes two step cycling protocols, alternating between a 16° C. incubation step to maximize DNA ligation efficiency and a 37-42° C. incubation step to maximize fragment digestion efficiency. The omission of 16° C. incubation was tested to determine the effect on multi-fragment assembly fidelity, as higher reaction temperatures have been shown to improve DNA ligase fidelity. The frequency of multi-fragment assembly errors at 37° C. or 42° C. was quantified in a multiplex high throughput DNA sequencing assay, and the results compared to reactions using traditional thermocycling protocols of 37/16° C. or 42/16° C. The reactions carried out at constant incubation temperatures were incubated for an extended duration, 16 hours, to compensate for decreased ligation efficiency. The results showed that the frequency of ligation errors was diminished >2-fold when the 16° C. incubation step was omitted, with every mismatch pair appearing less frequently.

Multi-fragment assembly reactions could exceed 50 fragments per reaction using a single temperature incubation (static). In this example using BsaI or BsmBI restriction endonuclease, the estimated assembly fidelity for traditional 37/16° C. or 42/16° C. cycling conditions dropped below 10% at 50 fragments, but the 37° C. or 42° C. static incubation protocols could allow >50 fragment to be assembled with >40% accuracy. The static 37° C. or 42° C. static temperature utilized longer incubation times to compensate for the efficiency loss caused by omitting the 16° C. incubation step.

Mismatch frequencies for assembly reactions were grouped according to nucleotide mispair (A:A, A:C, A:G, C:C, C:T, G:G, G:T, T:T). Assembly reactions were carried out with T4 DNA ligase and either BsaI-HFv2 at 37° C. or BsmBI-v2 at 42° C. For comparison, mismatch frequencies are shown for assembly reactions using traditional thermocycling protocols with T4 DNA ligase and either BsaI-HFv2 at 37° C. and 16° C. or BsmBI-v2 at 42° C. and 16° C. Mismatch frequency was significantly lower using BsaI-HFv2 (37° C.) or BsmBI-v2 (42° C.) at a single temperature than observed for cycling.

To test the predictions made herein, a 4.9 kb cassette of the lac operon was cloned into an E. coli destination vector from 52 constituent parts in a single assembly round. Importantly, the lac operon cassette system used here mimics a traditional cloning reactions wherein, upon transformation of the assembly reaction into E. coli cells, colonies harboring correctly or incorrectly assembled constructs can be readily observed. This test system provides a colorimetric readout to differentiate transformants harboring correctly and incorrectly assembled products.

Clonogenic Assays

Assembly reactions to reconstruct the lac operon cassette were transformed into chemically competent E. coli cells, and colony forming units were scored as harboring correctly or erroneously assembled constructs by a reverse blue-white screen as described previously. Briefly, transformations were performed using 2 µL of each assembly reaction added to 50 µL of T7 express competent cells as per manufacturer's instructions. The resulting outgrowth was plated onto agar plates (Luria-Bertani broth supplemented with 1 mg/mL dextrose, 1 mg/mL MgCl2, 30 µg/mL Chloramphenicol, 200 µM IPTG and 80 µg/mL X-gal). Importantly, transformants harboring correctly assembled constructs turn blue after incubation on media containing IPTG and X-Gal, while transformants harboring constructs with assembly errors form white colonies.

Verification of the 52 Fragment Lac Operon Cassette Assembly

Plasmid DNA was isolated from 18 blue colonies using the Monarch Plasmid Miniprep kit (New England Biolabs, Ipswich, MA). Twelve of the resulting constructs were subjected to PCR with amplification primers that flank the desired insertion site. Every construct yielded an amplicon size consistent with assembly of all 52 fragments, demonstrating that blue colonies contained the desired number of inserts. Six of the isolated constructs were sequenced using nine different sequencing primers to cover the entire 4.9 kb expected insert. All 6 constructs contained ordered error-free assembly of all 52-inserts.

52-Fragment Lac Assembly: 4-Base Overhang (BsaI-HFv2): Overhangs:

GGAG, CCAG, ATGT, TACA, GGCA, TATC, TAAG, CAGC,

GAAC, CAAC, GCTT, TAGT, CTAT, GGAA, TTCG, AGAC,

GTAT, GCGT, GATT, TTAC, TATT, TCGT, CAGA, GGGA,

CTCA, GCAA, TGGA, CGTC, AACC, AGTA, TAGA, GAAA,

-continued

AGGG, TTCT, ACAA, AGGT, TGTT, GAGT, TGGC, ACCG,

ATTA, GTGC, AGCG, TCTT, CGTG, CCGA, ATCA, TCTC,

CAAA, TTCA, TAGG, TATG, CCAT (Fragment sizes (base pairs): 83, 125, 103, 45, 114, 83, 122, 81, 89, 139, 81, 119, 62, 96, 92, 92, 107, 113, 85, 82, 113, 95, 110, 78, 96, 78, 101, 103, 115, 75, 113, 98, 115, 63, 99, 126, 93, 69, 102, 86, 139, 56, 121, 73, 128, 110, 67, 93, 144, 90, 96, 77)

It was found that 49% of the observed transformants harbored correctly assembled constructs, in close agreement with the predicted fidelity of 40%. To further confirm successful assembly of all 52 inserts, constructs were purified from a subset of colonies and the inserts analyzed by PCR and Sanger sequencing; all colonies subjected to additional screening were found to harbor constructs with inserts of the anticipated size and sequence.

Plasmid DNA was isolated from 18 blue colonies using the Monarch Plasmid Miniprep Kit (New England Biolabs, Ipswich, MA). Twelve of the resulting constructs were subjected to PCR with amplification primers that flank the desired insertion site. Every construct yielded an amplicon size consistent with assembly of all 52 fragments, demonstrating that blue colonies contained the desired number of inserts. Six of the isolated constructs were sequenced using nine different sequencing primers to cover the entire 4.9 kb expected insert. All 6 constructs contained ordered error-free assembly of all 52-inserts.

In summary, the one step assembly of phage T7 DNA and the lac operon cassette demonstrate an efficient and cost-effective means to create and engineer variants of large/complex DNA constructs that are difficult to obtain and manipulate by current cloning and gene synthesis methodologies. Multi-fragment assembly is shown here for rapid assembly of toxic and/or high molecular weight DNA constructs from dozens of smaller constituent parts that are easily manipulated and propagated using standard molecular biology techniques. These findings dramatically reduce the number of hierarchical assembly rounds required to produce large constructs by in vitro assembly and can be utilized to assemble entire metabolic pathways and even small genomes in a single reaction.

Example 5: Rapid One-Pot DNA Molecule Construction from 50 Fragments of 40 Kb T7 Phage DNA Enzymes, buffers, and media were obtained from New England Biolabs, Ipswich, MA (NEB, Ipswich, MA), unless otherwise noted. Synthetic oligonucleotides were obtained from either Integrated DNA Technologies (IDT, Coralville, IA) or Sigma Aldrich (Sigma, St. Louis, MO). As the phage genome contains many genes that are toxic to E. coli cells, the phage gDNA was reconstructed from PCR-generated DNA fragments to avoid subcloning toxic genes. Using this strategy, 16 silent mutations were introduced into the phage genome to remove pre-existing BsmBI Type IIS restriction sites within the genome. These changes served the dual purpose of both permitting Type IIS assembly and acting as marker mutations for assembly verification.

Assembly of large targets in a single round from many small fragments was tested as follows: 52 fragments were used to construct the 38 kb T7 bacteriophage genome 52 different optimized 4-base overhangs were selected from the intact T7 viral genome by SplitSet and the selected set of 4-base overhangs verified by GetSet using ligation conditions in the drop down menu for the conditions specified below.
Overhang Sequences Obtained by Data Optimized Assemble Design
52 Fragment T7 Phage Assembly (BsmBI) Overhangs:

AAAT, AGAA, AGCG, ATGT, TAGT, TCGC, CTGG, ACAA,

AGAC, GCTG, GGCA, ACCC, ACCG, AAGC, TACT, AATC,

AAGG, GAAA, GGTT, CAAC, CGTC, CCTA, TGGG, TAAG,

TCAT, ACGG, GTAA, CATT, TATC, TGAG, GCAC, CCAC,

TTCG, TCTG, AGGA, ACGC, TGGC, GTAT, CGTG, CTAT,

GAGA, ACTC, GGTG, TCCA, GGGA, GTTC, TTGC, GAAG,

GGAA, CAAA, ATCA, TGTT (Fragment sizes (base pairs): 779, 918, 512, 465, 810, 756, 731, 820, 690, 759, 813, 743, 644, 1043, 494, 887, 526, 918, 854, 837, 540, 880, 678, 812, 732, 802, 976, 530, 745, 568, 885, 1130, 148, 1008, 847, 667, 748, 831, 842, 753, 947, 428, 928, 411, 301, 1383, 424, 1056, 893, 653, 815, 1735)
Multi-Fragment Assembly Reactions Assembly fragments were generated by PCR (Q5® Hot-Start High-Fidelity 2× Master Mix (New England Biolabs, Ipswich, MA)) with oligonucleotide primers (IDT) and purified using the Monarch PCR & DNA Cleanup Kit. Fragment quality was evaluated using the Agilent Bioanalyzer 2100 and each assembly part was quantified using the Qubit Assay (Thermo Fisher Scientific, Waltham, MA). Multi-fragment assembly reactions (5 µL final volume) were carried out with 3 nM of each DNA fragment and 0.5 µL of the appropriate multi-fragment assembly mix (NEB® Golden Gate Assembly Mix (New England Biolabs, Ipswich, MA) in 1× T4 DNA ligase buffer; the BsmBI-v2 mix was used to assemble the T7 phage genome. Reactions to produce the T7 bacteriophage genome were cycled between 42° C. and 16° C. for 5 minutes at each temperature for 96 cycles, and then subjected to a 60° C. incubation for 5 minutes and finally a 4° C. hold until transformation into E. coli
Plaque Assays The assembled T7 phage genome was transformed into NEB 10-beta electrocompetent cells as per the manufacturer's instructions, using 1 µL of the reaction mixture into 25 µL of competent cells. The transfection mixture was recovered in 975 µL of NEB 10-beta/stable outgrowth media and then combined with 3 mL of 50° C. molten top-agar (Luria broth containing 0.7% agar). The resulting plates were inverted and incubated at 37° C. for ~5 hours until the E. coli lawn and phage plaques were visible by eye. Upon transformation, about 20 bacteriophage plaques/ul assembly reaction were obtained indicating successful assembly of the phage genome.
Verification of 52 Fragment T7 Phage gDNA Assembly Several phage plaques were selected for additional screening by plaque PCR and restriction enzyme digest to ensure they contained a complete and correctly ordered copy of the T7 phage genome; all plaques subjected to additional screening contained the expected genome arrangement and harbored the intended silent mutations. Plaque PCR was carried out using 4 sets of amplification primers that together span the 40 kb phage genome. Amplicon lengths were resolved by Agilent Bioanalyzer 2100, using a DNA 12000 assay. Amplicons from 5 phage plaques were compared to the parental wt T7 phage genome after restriction enzyme digest with NdeI or undigested. In all cases, the phage plaques produced a pattern identical to the parental wt T7 gDNA. The assembled genome harbored the desired silent mutations that remove native BsmBI restriction sites and it was verified that the observed plaques were not the results of carryover-contamination from the parental T7 phage gDNA by amplicon digestion of the parental T7 phage genome and plaques with BsmBI. The amplicon from the parental T7 phage genome was digested by BsmBI to produce the bands of expected size, whereas the amplicons from the assembled phage genomes were inert to cleavage by BsmBI.

Moreover, to ensure the observed phage plaques were the result of in vitro assembly and not assembly of the DNA fragments within the E. coli by cellular DNA repair mechanisms, control reactions lacking T4 DNA ligase were performed and no phage plaques were observed upon transformation of these control reactions. These results demonstrate that using a high stringency screen allows rapid assembly of >50 DNA fragments under ordered assembly conditions using Data Optimized Assembly Design.

It was noted that the high-temperature assembly protocol variations were not necessary to produce infectious phage plaques; presumably due to the more stringent selection of the plaque forming assay, as improperly assembled variants of the T7 phage genome are unlikely to produce viable phage and thus there is no background from incorrectly assembled products. This is in contrast to another successful assemble of the lac operon cassette test system from 52 fragments where cycling was used. Taken together, these results demonstrate rapid assembly of a phage genome, and suggest that the methods developed here could be applied to other large and/or complex DNA targets.

TABLE 7

Examples of computer-generated optimized overhang sets according to the methods herein.

| # fragments | Examples of sets of optimized overhangs |
|---|---|
| 20 | AGTG, CAGG, ACTC, AAAA, AGAC, CGAA, ATAG, AACC, TACA, TAGA, ATGC, GATA, CTCC, GTAA, CTGA, ACAA, AGGA, ATTA, ACCG, GCGA |
| 24 | GGAG, GATA, GGCA, GGTC, TCGC, GAGG, CAGT, GTAA, TCCA, CACA, GAAT, ATAG, AGTA, ATCA, TCTT, AGGT, CAAA, AAGC, GCAC, CAAC, CGAA, GTCT, TCAG, CCAT |
| 24 | GGAG, GATA, GGCA, GGTC, TCGC, GAGG, CAGT, GTAA, TCCA, CACA, GAAT, ATAG, AGTA, ATCA, TCTT, AGGT, CAAA, AAGC, GCAC, CAAC, CGAA, GTCT, TCAG, CCAT |
| 24 | TTGC, TGGA, TGAG, TAGG, ACAG, AAGC, AGCC, GTCA, CGTT, ATTT, TTCT, GAAA, GATG, GTAT, GCAC, TCGT, GGTC, CGGG, CACT, ACTA, ACCT, TCTC, ATGG, GTAG |
| 25 | GCCC, CCAA, ATCC, GGTA, ACGG, AAAT, ATAG, CTTA, AGGA, AGTC, ACAC, ATGA, GCGA, CATA, CTGC, AACG, CGCC, AGTG, CCTC, GAAA, CAGA, ACCA, AAGT, CGAA, CAAC |
| 30 | AAAC, AACA, AAGA, AAGT, AATG, ACAC, ACGA, AGAA, AGCC, AGGG, AGTA, ATAG, ATCA, ATGA, ATTC, CAAA, CACG, CAGA, CCAG, CCTA, CGAA, CGGC, CTCC, CTTA, GAGC, GATA, GCAA, GGGA, GTAA, TCCA |

TABLE 7-continued

Examples of computer-generated optimized overhang sets according to the methods herein.

| # frag-ments | Examples of sets of optimized overhangs |
|---|---|
| 52 | GGAG, CCAG, ATGT, TACA, GGCA, TATC, TAAG, CAGC, GAAC, CAAC, GCTT, TAGT, CTAT, GGAA, TTCG, AGAC, GTAT, GCGT, GATT, TTAC, TATT, TCGT, CAGA, GGGA, CTCA, GCAA, TGGA, CGTC, AACC, AGTA, TAGA, GAAA, AGGG, TTCT, ACAA, AGGT, TGTT, GAGT, TGGC, ACCG, ATTA, GTGC, AGCG, TCTT, CGTG, CCGA, ATCA, TCTC, CAAA, TTCA, TAGG, TATG, CCAT |
| 52 | AAAT, AGAA, AGCG, ATGT, TAGT, TCGC, CTGG, ACAA, AGAC, GCTG, GGCA, ACCC, ACCG, AAGC, TACT, AATC, AAGG, GAAA, GGTT, CAAC, CGTC, CCTA, TGGG, TAAG, TCAT, ACGG, GTAA, CATT, TATC, TGAG, GCAC, CCAC, TTCG, TCTG, AGGA, ACGC, TGGC, GTAT, CGTG, CTAT, GAGA, ACTC, GGTG, TCCA, GGGA, GTTC, TTGC, GAAG, GGAA, CAAA, ATCA, TGTT |
| 100 | TTAC, CCCA, AACT, TTTT, TGTA, CGAA, GGAG, TAGC, CAAG, ACAA, CTAT, GGTC, TGGC, AGAA, ACTT, AGTG, TCTG, ATGC, AAGG, CAAC, TCTT, GAAG, GTGG, TTGA, TCGG, CTCT, GGTA, GATG, AATC, GACA, ACTA, CGCA, TGAA, ATCG, CCAA, CCAT, CATA, GAGA, TAGA, TCGT, GGTT, CTCG, AAAG, GGAT, TGCT, TATT, CTCA, ATTC, TGAT, CATT, CTGG, GTTA, CTAA, AACG, GTAG, ACGC, TGTG, GCAC, GCAA, ATTT, GGCT, TCCG, CTGC, TCAC, TCAT, TAGG, CCGT, GATA, AGAC, TAAG, TCCC, GGGT, GAGT, ATAC, GTTT, TCCA, ACCG, ACTG, CAAA, GGCG, GACT, TGTT, GAAA, TACG, TCAG, GTTC, GCGA, GCTT, GCTC, TACT, AGAT, TGGT, AGGA, TAAT, GGAA, ACCT, CAAT, CCCC, ATGT, TGAC |

Overhangs were generated using the data using BsaI-HFv2, BsmBI or BspQI:

The following are the overhangs used in Table 8.

Overhangs are written here in the 5' to 3' direction with the phosphate omitted.

24-Fragment Lac Assembly: 4-Base Overhang (BsaI-HFv2; BsmBI):
Overhangs:

GGAG, GATA, GGCA, GGTC, TCGC, GAGG, CAGT, GTAA,

TCCA, CACA, GAAT, ATAG, AGTA, ATCA, TCTT, AGGT,

CAAA, AAGC, GCAC, CAAC, CGAA, GTCT, TCAG, CCAT (Fragment sizes (base pairs): 118, 222, 222, 199, 137, 217, 197, 244, 293, 173, 127, 208, 287, 310, 291, 259, 176, 217, 135, 176, 184, 133, 203, 119)

24-Fragment T4 Phage Assembly (BsmBI):
Overhangs:

GGAG, GATA, GGCA, GGTC, TCGC, GAGG, CAGT, GTAA,

TCCA, CACA, GAAT, ATAG, AGTA, ATCA, TCTT, AGGT,

CAAA, AAGC, GCAC, CAAC, CGAA, GTCT, TCAG, CCAT (Fragment size: 8 kb)

24-Fragment T4 Phage Assembly (BsmBI):
Overhangs:

TTGC, TGGA, TGAG, TAGG, ACAG, AAGC, AGCC, GTCA,

CGTT, ATTT, TTCT, GAAA, GATG, GTAT, GCAC, TCGT,

GGTC, CGGG, CACT, ACTA, ACCT, TCTC, ATGG, GTAG (Fragment sizes (base pairs): 4631, 9473, 7031, 7465, 10181, 1595, 8807, 3851, 4152, 10945, 11254, 7290, 1680, 10213, 7152, 6898, 7162, 7104, 6967, 6827, 8052, 8947, 4304, 7018)

30-Fragment all-Purpose Overhang Set (any 4-Cutter):
Overhangs:

AAAC, AACA, AAGA, AAGT, AATG, ACAC, ACGA, AGAA,

AGCC, AGGG, AGTA, ATAG, ATCA, ATGA, ATTC, CAAA,

CACG, CAGA, CCAG, CCTA, CGAA, CGGC, CTCC, CTTA,

GAGC, GATA, GCAA, GGGA, GTAA, TCCA

52-Fragment T7 Phage Assembly (BsmBI)
Overhangs:

AAAT, AGAA, AGCG, ATGT, TAGT, TCGC, CTGG, ACAA,

AGAC, GCTG, GGCA, ACCC, ACCG, AAGC, TACT, AATC,

AAGG, GAAA, GGTT, CAAC, CGTC, CCTA, TGGG, TAAG,

TCAT, ACGG, GTAA, CATT, TATC, TGAG, GCAC, CCAC,

TTCG, TCTG, AGGA, ACGC, TGGC, GTAT, CGTG, CTAT,

GAGA, ACTC, GGTG, TCCA, GGGA, GTTC, TTGC, GAAG,

GGAA, CAAA, ATCA, TGTT (Fragment sizes (base pairs): 779, 918, 512, 465, 810, 756, 731, 820, 690, 759, 813, 743, 644, 1043, 494, 887, 526, 918, 854, 837, 540, 880, 678, 812, 732, 802, 976, 530, 745, 568, 885, 1130, 148, 1008, 847, 667, 748, 831, 842, 753, 947, 428, 928, 411, 301, 1383, 424, 1056, 893, 653, 815, 1735)

52-Fragment Lac Assembly: 4-Base Overhang (BsaI-HFv2):
Overhangs:

GGAG, CCAG, ATGT, TACA, GGCA, TATC, TAAG, CAGC,

GAAC, CAAC, GCTT, TAGT, CTAT, GGAA, TTCG, AGAC,

GTAT, GCGT, GATT, TTAC, TATT, TCGT, CAGA, GGGA,

CTCA, GCAA, TGGA, CGTC, AACC, AGTA, TAGA, GAAA,

AGGG, TTCT, ACAA, AGGT, TGTT, GAGT, TGGC, ACCG,

ATTA, GTGC, AGCG, TCTT, CGTG, CCGA, ATCA, TCTC,

CAAA, TTCA, TAGG, TATG, CCAT (Fragment sizes (base pairs): 83, 125, 103, 45, 114, 83, 122, 81, 89, 139, 81, 119, 62, 96, 92, 92, 107, 113, 85, 82, 113, 95, 110, 78, 96, 78, 101, 103, 115, 75, 113, 98, 115, 63, 99, 126, 93, 69, 102, 86, 139, 56, 121, 73, 128, 110, 67, 93, 144, 90, 96, 77)

100-Fragment T4 Phage Assembly (BsmBI):
Overhangs:

TTAC, CCCA, AACT, TTTT, TGTA, CGAA, GGAG, TAGC,

CAAG, ACAA, CTAT, GGTC, TGGC, AGAA, ACTT, AGTG,

TCTG, ATGC, AAGG, CAAC, TCTT, GAAG, GTGG, TTGA,

TCGG, CTCT, GGTA, GATG, AATC, GACA, ACTA, CGCA,

TGAA, ATCG, CCAA, CCAT, CATA, GAGA, TAGA, TCGT,

GGTT, CTCG, AAAG, GGAT, TGCT, TATT, CTCA, ATTC,

TGAT, CATT, CTGG, GTTA, CTAA, AACG, GTAG, ACGC,

TGTG, GCAC, GCAA, ATTT, GGCT, TCCG, CTGC, TCAC,

TCAT, TAGG, CCGT, GATA, AGAC, TAAG, TCCC, GGGT,

GAGT, ATAC, GTTT, TCCA, ACCG, ACTG, CAAA, GGCG,

GACT, TGTT, GAAA, TACG, TCAG, GTTC, GCGA, GCTT,

GCTC, TACT, AGAT, TGGT, AGGA, TAAT, GGAA, ACCT,

CAAT, CCCC, ATGT, TGAC (Fragment sizes (base pairs): 395, 383, 424, 367, 451, 506, 287, 411, 352, 355, 419, 357, 519, 208, 448, 379, 412, 380, 422, 475, 337, 481, 242, 537, 320, 450, 522, 149, 562, 329, 312, 567, 389, 328, 456, 301, 390, 479, 282, 402, 494, 340, 450, 287, 569, 380, 396, 334, 390, 412, 295, 487, 199, 627, 290, 557, 382, 409, 296, 418, 906, 143, 193, 296, 436, 412, 465, 295, 511, 312, 341, 369, 448, 451, 421, 297, 380, 425, 479, 150, 679, 320, 356, 495, 223, 562, 399, 319, 317, 268, 628, 435, 368, 355, 451, 308, 555, 336, 357, 1074)

Example 6: Synthesis and Engineering of a Viral Genome for Research and Vaccine Development e.g. Coronavirus Reverse genetic systems that rely on in vitro ligation offer researchers a relatively fast/efficient way to generate variants of RNA viruses for research purposes and vaccine development efforts. This methodology has worked for manipulation of several viruses but has not yet been successfully applied to many high-value targets, including coronaviruses (despite several attempts). It is likely that the large size and inherently toxic/repetitive nature of some viral genomes prohibits maintenance of the viral genomic DNA in *E. coli* cells by traditional techniques. However, efficient assembly of the viral genome from many parts can be accomplished using the methods described herein. Toxic viral genomes can be sub-divided into small fragments for easy manipulation in *E. coli* cells, permitting one-tube assembly of the viral cDNA in a few hours. As an example, we demonstrate below the designs of a 12-fragment, 24-fragment, and 50-fragment linear viral genome assembly (Genbank ID: NC_045512, from severe acute respiratory syndrome coronavirus 2 isolate Wuhan-Hu-1, complete genome). These fragments may be contained in plasmids having a recognition sequence for a selected restriction endonuclease at the insertion sites. For example, the restriction endonuclease may be selected from: BsaI-HFv2, BsmBI-v2, BbsI-HF, SapI, BspQI and PaqCI. If PaqCI is selected for viral assembly, an activator molecule as described above should be included in the reaction mix. The product of cleavage with any of these restriction endonucleases results in an overhang. Optimization of overhang sequences is provided for various restriction endonucleases by WO 2020/081768 with the addition of the data for PaqCI (Table 8) and the use of the Computer Tool described in WO 2020/081768 and incorporated by reference. The reaction conditions for PaqCI cleavage and T4 DNA ligation. Using 75 ng/ul of the destination plasmid and 1 ul for the reaction, add 2 ul of T4 DNA ligase buffer (10×), 0.5-2 ul of PaqCI (10 u/ul), PaqCI activator (20 uM) 0.25-0.5 ul, T4 DNA ligase (400 u/ul) 0.50-2 ul and nuclease free water to 20 ul. The assembly protocol is (37° C., 5 minutes→16° C., 5 minutes)×30-60 cycles→37° C., 5 minutes→60° C., 5 minutes.

TABLE 8

Multi-fragment assembly fidelity of 5' phosphorylated 4-base overhangs using T4 DNA ligase and buffer (NEB) and PaqCI (5 minutes at 37° C. then 5 minutes at 16° C. for 60 cycles)

| Overhang | Correct, $\times 10^{-5}$ | Mismatch, $\times 10^{-5}$ | Fidelity[1] | Mismatch Overhangs[2] |
|---|---|---|---|---|
| AAAA | 100 | 1 | 98.6 | GTTT (33%); TTTC (33%); TTCT (33%) |
| AAAC | 90 | 11 | 89.5 | GTTG (27%); GGTT (18%); GTTA (18%) |
| AAAG | 153 | 40 | 79.5 | TTTT (49%); GTTT (16%); CTAT (7%) |
| AAAT | 176 | 74 | 70.4 | GTTT (66%); TTTT (16%); ATTG (6%) |
| AACA | 93 | 10 | 90.2 | GGTT (24%); TGTG (24%); AGTT (14%) |
| AACC | 86 | 12 | 88.1 | GGTG (25%); GGTA (25%); GTTT (12%) |
| AACG | 138 | 61 | 69.2 | TGTT (54%); CGGT (13%); GGTT (7%) |
| AACT | 160 | 77 | 67.6 | GGTT (42%); TGTT (38%); AGTG (6%) |
| AAGA | 200 | 20 | 91.0 | GCTT (39%); TTTT (27%); TGTT (20%) |
| AAGC | 146 | 51 | 74.1 | GTTT (24%); GGTT (23%); GATT (10%) |
| AAGG | 233 | 227 | 50.6 | TCTT (54%); CTTT (15%); CGTT (14%) |
| AAGT | 227 | 213 | 51.5 | GCTT (55%); TCTT (19%); ATTT (10%) |

TABLE 8-continued

Multi-fragment assembly fidelity of 5' phosphorylated 4-base overhangs using T4 DNA ligase and buffer (NEB) and PaqCI (5 minutes at 37° C. then 5 minutes at 16° C. for 60 cycles)

| Overhang | Correct, x10$^{-5}$ | Mismatch, x10$^{-5}$ | Fidelity[1] | Mismatch Overhangs[2] |
| --- | --- | --- | --- | --- |
| AATA | 174 | 30 | 85.1 | TGTT (41%); GATT (21%); TTTT (19%) |
| AATC | 177 | 53 | 76.8 | GGTT (44%); GTTT (30%); GATG (6%) |
| AATG | 209 | 208 | 50.1 | CTTT (35%); CGTT (27%); TATT (26%) |
| AATT | 231 | 188 | 55.2 | GATT (38%); TATT (23%); AGTT (17%) |
| ACAA | 106 | 4 | 96.1 | TTGG (22%); TTGA (22%); GTGT (22%) |
| ACAC | 78 | 32 | 70.7 | GTGG (61%); GGGT (12%); GTGC (9%) |
| ACAG | 137 | 87 | 61.2 | CTGG (43%); TTGT (32%); GTGT (7%) |
| ACAT | 141 | 91 | 60.8 | GTGT (51%); ATGG (22%); TTGT (15%) |
| ACCA | 97 | 22 | 81.8 | TGGG (44%); GGGT (20%); TGGA (13%) |
| ACCC | 93 | 13 | 87.7 | GGGG (52%); GGGC (11%); GGGA (11%) |
| ACCG | 142 | 78 | 64.6 | TGGT (45%); CGGG (27%); CGGA (6%) |
| ACCT | 131 | 88 | 59.8 | GGGT (41%); TGGT (30%); AGGG (19%) |
| ACGA | 176 | 44 | 80.1 | TTGT (33%); GCGT (25%); TCGG (19%) |
| ACGC | 144 | 76 | 65.6 | GTGT (34%); GCGG (22%); GGGT (19%) |
| ACGG | 197 | 281 | 41.2 | TCGT (39%); CTGT (22%); CCGG (12%) |
| ACGT | 166 | 271 | 38.0 | GCGT (41%); ATGT (18%); TCGT (17%) |
| ACTA | 185 | 42 | 81.4 | TGGT (33%); GAGT (26%); TTGT (22%) |
| ACTC | 168 | 87 | 65.8 | GTGT (31%); GGGT (29%); GAGG (25%) |
| ACTG | 187 | 262 | 41.6 | CTGT (32%); CGGT (22%); TAGT (18%) |
| ACTT | 227 | 268 | 45.9 | GAGT (30%); ATGT (23%); TAGT (20%) |
| AGAA | 191 | 22 | 89.6 | TTGT (37%); GTCT (22%); TTTT (15%) |
| AGAC | 127 | 68 | 64.9 | GTGT (27%); GTTT (23%); GTCG (21%) |
| AGAG | 186 | 201 | 48.1 | TTCT (34%); CTTT (20%); CTGT (19%) |
| AGAT | 209 | 225 | 48.1 | GTCT (42%); TTCT (16%); ATTT (13%) |
| AGCA | 144 | 55 | 72.3 | TGGT (25%); TGTT (24%); GGCT (16%) |
| AGCC | 126 | 79 | 61.5 | GGTT (28%); GGGT (25%); GGCG (13%) |
| AGCG | 158 | 258 | 38.0 | TGCT (36%); CGGT (18%); CGTT (13%) |
| AGCT | 155 | 277 | 35.9 | GGCT (31%); TGCT (24%); AGGT (17%) |
| AGGA | 222 | 158 | 58.4 | TTCT (32%); TCTT (19%); TCGT (18%) |
| AGGC | 152 | 273 | 35.8 | GCTT (24%); GCGT (21%); GTCT (20%) |
| AGGG | 149 | 382 | 28.1 | TCCT (33%); CTCT (15%); CCGT (10%) |
| AGGT | 131 | 364 | 26.4 | GCCT (27%); ATCT (14%); AGCT (13%) |
| AGTA | 214 | 132 | 61.8 | TGCT (33%); TATT (19%); TTCT (19%) |
| AGTC | 187 | 261 | 41.8 | GGCT (31%); GATT (24%); GAGT (17%) |
| AGTG | 137 | 385 | 26.3 | TACT (20%); CTCT (19%); CGCT (17%) |
| AGTT | 160 | 290 | 35.6 | TACT (19%); GACT (18%); ATCT (15%) |

TABLE 8-continued

Multi-fragment assembly fidelity of 5' phosphorylated 4-base overhangs using T4 DNA ligase and buffer (NEB) and PaqCI (5 minutes at 37° C. then 5 minutes at 16° C. for 60 cycles)

| Overhang | Correct, x10$^{-5}$ | Mismatch, x10$^{-5}$ | Fidelity[1] | Mismatch Overhangs[2] |
|---|---|---|---|---|
| ATAA | 167 | 32 | 84.0 | TTTT (36%); TTGT (29%); GTAT (14%) |
| ATAC | 125 | 92 | 57.5 | GTGT (45%); GTTT (33%); GGAT (6%) |
| ATAG | 222 | 213 | 50.9 | CTTT (36%); CTGT (32%); TTAT (15%) |
| ATAT | 215 | 194 | 52.5 | GTAT (36%); ATGT (24%); ATTT (21%) |
| ATCA | 195 | 68 | 74.0 | TGGT (37%); TGTT (23%); GGAT (17%) |
| ATCC | 170 | 78 | 68.5 | GGGT (38%); GGTT (31%); GGAG (6%) |
| ATCG | 200 | 270 | 42.6 | TGAT (31%); CGGT (27%); CGTT (18%) |
| ATCT | 209 | 296 | 41.4 | GGAT (32%); TGAT (29%); AGGT (17%) |
| ATGA | 253 | 134 | 65.3 | TCGT (37%); TCTT (28%); TTAT (17%) |
| ATGC | 174 | 261 | 40.0 | GCGT (32%); GCTT (29%); GTAT (15%) |
| ATGG | 166 | 440 | 27.4 | TCAT (30%); CCGT (19%); CCTT (13%) |
| ATGT | 141 | 338 | 29.4 | GCAT (25%); ACTT (18%); ACGT (14%) |
| ATTA | 231 | 112 | 67.3 | TATT (27%); TGAT (27%); TTAT (15%) |
| ATTC | 218 | 268 | 44.9 | GGAT (30%); GATT (27%); GTAT (18%) |
| ATTG | 161 | 437 | 27.0 | CTAT (18%); TAAT (17%); CATT (16%) |
| ATTT | 176 | 270 | 39.5 | GAAT (20%); TAAT (18%); ATAT (15%) |
| CAAA | 113 | 9 | 92.9 | GTTG (50%); ATTG (11%); TGTG (11%) |
| CAAC | 91 | 17 | 84.4 | GGTG (29%); GTGG (20%); GTAG (14%) |
| CAAG | 142 | 104 | 57.8 | TTTG (60%); GTTG (12%); CTTT (7%) |
| CAAT | 161 | 91 | 63.9 | GTTG (65%); TTTG (19%); AGTG (5%) |
| CACA | 102 | 25 | 80.2 | GGTG (48%); TGGG (25%); AGTG (15%) |
| CACC | 90 | 17 | 84.2 | GGGG (20%); GTTG (20%); TGTG (14%) |
| CACG | 124 | 127 | 49.4 | TGTG (51%); CGGG (14%); AGTG (10%) |
| CACT | 137 | 106 | 56.3 | TGTG (38%); GGTG (37%); AGGG (11%) |
| CAGA | 184 | 46 | 80.1 | GCTG (41%); TTTG (25%); TGTG (12%) |
| CAGC | 154 | 75 | 67.2 | GTTG (31%); GGTG (25%); GATG (17%) |
| CAGG | 186 | 288 | 39.3 | TCTG (53%); ACTG (12%); CGTG (10%) |
| CAGT | 187 | 252 | 42.6 | GCTG (39%); TCTG (19%); AGTG (16%) |
| CATA | 166 | 57 | 74.4 | TTTG (34%); TGTG (29%); GATG (19%) |
| CATC | 172 | 97 | 63.9 | GGTG (44%); GTTG (35%); GAGG (4%) |
| CATG | 202 | 250 | 44.7 | TATG (38%); CGTG (19%); CTTG (14%) |
| CATT | 209 | 306 | 40.5 | GATG (32%); ATTG (23%); TATG (19%) |
| CCAA | 99 | 11 | 90.3 | GTGG (55%); TGGG (14%); ATGG (14%) |
| CCAC | 113 | 16 | 87.7 | GGGG (30%); GTTG (21%); GAGG (15%) |
| CCAG | 163 | 91 | 64.3 | TTGG (66%); CGGG (10%); GTGG (8%) |
| CCAT | 166 | 85 | 66.0 | GTGG (56%); TTGG (28%); AGGG (8%) |
| CCCA | 106 | 10 | 91.3 | GGGG (57%); AGGG (24%); TGGT (10%) |

TABLE 8-continued

Multi-fragment assembly fidelity of 5' phosphorylated 4-base overhangs using T4 DNA ligase and buffer (NEB) and PaqCI (5 minutes at 37° C. then 5 minutes at 16° C. for 60 cycles)

| Overhang | Correct, x10$^{-5}$ | Mismatch, x10$^{-5}$ | Fidelity[1] | Mismatch Overhangs[2] |
|---|---|---|---|---|
| CCCC | 100 | 11 | 90.4 | TGGG (55%); GGGT (9%); GAGG (9%) |
| CCCG | 157 | 70 | 69.0 | TGGG (67%); AGGG (13%); GGGG (5%) |
| CCCT | 149 | 92 | 61.9 | GGGG (45%); TGGG (42%); CGGG (5%) |
| CCGA | 171 | 69 | 71.2 | TTGG (49%); GCGG (27%); ACGG (7%) |
| CCGC | 158 | 87 | 64.5 | GTGG (55%); GGGG (17%); TCGG (6%) |
| CCGG | 158 | 341 | 31.7 | TCGG (48%); CTGG (17%); ACGG (10%) |
| CCGT | 197 | 319 | 38.1 | GCGG (39%); ATGG (26%); TCGG (16%) |
| CCTA | 151 | 68 | 68.8 | TTGG (36%); TGGG (27%); GAGG (18%) |
| CCTC | 184 | 83 | 69.0 | GGGG (44%); GTGG (39%); TAGG (8%) |
| CCTG | 186 | 276 | 40.3 | TAGG (26%); CTGG (25%); CGGG (25%) |
| CCTT | 233 | 294 | 44.1 | GAGG (34%); TAGG (20%); ATGG (20%) |
| CGAA | 196 | 45 | 81.4 | TTTG (43%); GTCG (18%); TTGG (16%) |
| CGAC | 117 | 86 | 57.6 | GTTG (45%); GGCG (21%); GTGG (8%) |
| CGAG | 199 | 283 | 41.3 | TTCG (45%); CTTG (14%); GTCG (12%) |
| CGAT | 200 | 278 | 41.9 | GTCG (35%); ATTG (23%); TTCG (20%) |
| CGCA | 155 | 69 | 69.2 | TGTG (34%); GGCG (22%); TGGG (15%) |
| CGCC | 136 | 95 | 58.8 | GGTG (38%); GGGG (20%); TGCG (10%) |
| CGCG | 157 | 292 | 35.0 | TGCG (43%); CGGG (16%); CGTG (15%) |
| CGCT | 158 | 301 | 34.5 | TGCG (30%); GGCG (27%); AGTG (22%) |
| CGGA | 231 | 237 | 49.4 | TTCG (41%); TCTG (26%); TGCG (11%) |
| CGGC | 171 | 315 | 35.2 | GCTG (27%); GTCG (26%); GGCG (15%) |
| CGGG | 157 | 484 | 24.4 | TCCG (28%); CTCG (16%); CCTG (14%) |
| CGGT | 142 | 448 | 24.0 | GCCG (26%); ATCG (16%); TCCG (13%) |
| CGTA | 182 | 174 | 51.2 | TGCG (27%); TATG (23%); TTCG (22%) |
| CGTC | 173 | 308 | 36.0 | GATG (29%); GGCG (22%); GTCG (21%) |
| CGTG | 124 | 275 | 31.1 | TACG (23%); CATG (17%); CGCG (16%) |
| CGTT | 138 | 389 | 26.1 | TACG (19%); GACG (19%); AATG (14%) |
| CTAA | 157 | 46 | 77.4 | TTTG (44%); TTGG (23%); GTAG (16%) |
| CTAC | 133 | 88 | 60.3 | GTTG (42%); GTGG (35%); GGAG (13%) |
| CTAG | 205 | 237 | 46.5 | CTGG (31%); TTAG (26%); CTTG (21%) |
| CTAT | 222 | 297 | 42.7 | GTAG (34%); ATTG (27%); ATGG (19%) |
| CTCA | 177 | 88 | 66.8 | TGTG (42%); TGGG (26%); GGAG (14%) |
| CTCC | 161 | 83 | 65.9 | GGTG (49%); GGGG (31%); GGCG (6%) |
| CTCG | 199 | 262 | 43.2 | TGAG (41%); CGGG (30%); CGTG (12%) |
| CTCT | 186 | 369 | 33.6 | GGAG (32%); TGAG (25%); AGTG (20%) |
| CTGA | 224 | 237 | 48.5 | TCTG (39%); TCGG (23%); TTAG (15%) |

TABLE 8-continued

Multi-fragment assembly fidelity of 5' phosphorylated 4-base overhangs using T4
DNA ligase and buffer (NEB) and PaqCI (5 minutes at 37° C. then 5 minutes
at 16° C. for 60 cycles)

| Overhang | Correct, x10$^{-5}$ | Mismatch, x10$^{-5}$ | Fidelity[1] | Mismatch Overhangs[2] |
|---|---|---|---|---|
| CTGC | 140 | 296 | 32.2 | GCTG (32%); GCGG (24%); GTAG (22%) |
| CTGG | 163 | 477 | 25.4 | TCAG (28%); CTAG (15%); CCTG (15%) |
| CTGT | 137 | 473 | 22.5 | GCAG (20%); ACTG (18%); ATAG (14%) |
| CTTA | 252 | 195 | 56.5 | TATG (31%); TTAG (19%); TGAG (18%) |
| CTTC | 204 | 357 | 36.4 | GATG (32%); GGAG (22%); GTAG (19%) |
| CTTG | 142 | 286 | 33.2 | CTAG (17%); TAAG (15%); CGAG (14%) |
| CTTT | 153 | 503 | 23.3 | ATAG (15%); GAAG (15%); AATG (15%) |
| GAAA | 198 | 17 | 92.1 | TTTT (51%); TTTG (20%); GTTC (14%) |
| GAAC | 137 | 80 | 63.1 | GTTT (57%); GTTG (13%); GTTA (12%) |
| GAAG | 204 | 193 | 51.5 | CTTT (39%); TTTC (32%); CTTA (8%) |
| GAAT | 218 | 239 | 47.7 | GTTC (45%); ATTT (23%); TTTC (15%) |
| GACA | 148 | 86 | 63.2 | TGTT (36%); GGTC (24%); TGGC (12%) |
| GACC | 138 | 84 | 62.1 | GGTT (49%); GGGC (14%); GGTA (13%) |
| GACG | 173 | 255 | 40.4 | TGTC (32%); CGTT (28%); CGGC (9%) |
| GACT | 187 | 255 | 42.3 | GGTC (32%); TGTC (26%); AGTT (21%) |
| GAGA | 250 | 140 | 64.1 | TCTT (34%); TTTC (22%); GCTC (16%) |
| GAGC | 168 | 276 | 37.9 | GCTT (42%); GTTC (19%); GGTC (16%) |
| GAGG | 184 | 421 | 30.4 | TCTC (33%); CCTT (24%); CTTC (13%) |
| GAGT | 168 | 392 | 30.0 | GCTC (26%); ACTT (21%); ATTC (12%) |
| GATA | 217 | 166 | 56.7 | TATT (29%); TGTC (26%); TTTC (22%) |
| GATC | 192 | 279 | 40.7 | GATT (33%); GGTC (31%); GTTC (16%) |
| GATG | 172 | 521 | 24.8 | CTTC (22%); CATT (19%); CGTC (17%) |
| GATT | 177 | 435 | 29.0 | GATC (21%); ATTC (17%); AATT (16%) |
| GCAA | 162 | 50 | 76.4 | TTGT (60%); GTGC (12%); TTGG (10%) |
| GCAC | 112 | 111 | 50.2 | GTGT (52%); GTGA (21%); GGGC (10%) |
| GCAG | 140 | 271 | 34.1 | CTGT (36%); TTGC (29%); CTGA (11%) |
| GCAT | 174 | 320 | 35.2 | GTGC (38%); ATGT (26%); TTGC (14%) |
| GCCA | 132 | 94 | 58.4 | TGGT (64%); GGGC (14%); TGGA (7%) |
| GCCC | 121 | 92 | 56.9 | GGGT (61%); GGGA (19%); TGGC (7%) |
| GCCG | 171 | 319 | 34.9 | CGGT (37%); TGGC (27%); CGGG (8%) |
| GCCT | 152 | 325 | 31.8 | AGGT (30%); GGGC (27%); TGGC (22%) |
| GCGA | 184 | 233 | 44.2 | TCGT (43%); TTGC (30%); GCGC (7%) |
| GCGC | 151 | 294 | 34.0 | GCGT (40%); GTGC (22%); GGGC (14%) |
| GCGG | 158 | 540 | 22.7 | TCGC (27%); CCGT (23%); CTGC (13%) |
| GCGT | 144 | 590 | 19.6 | GCGC (20%); ACGT (19%); ATGC (14%) |
| GCTA | 180 | 235 | 43.4 | TAGT (33%); TGGC (24%); TTGC (20%) |
| GCTC | 168 | 295 | 36.3 | GAGT (34%); GGGC (25%); GTGC (19%) |

TABLE 8-continued

Multi-fragment assembly fidelity of 5' phosphorylated 4-base overhangs using T4 DNA ligase and buffer (NEB) and PaqCI (5 minutes at 37° C. then 5 minutes at 16° C. for 60 cycles)

| Overhang | Correct, x10$^{-5}$ | Mismatch, x10$^{-5}$ | Fidelity[1] | Mismatch Overhangs[2] |
|---|---|---|---|---|
| GCTG | 154 | 568 | 21.3 | TAGC (17%); CAGT (17%); CTGC (16%) |
| GCTT | 146 | 597 | 19.7 | AAGT (20%); GAGC (20%); TAGC (15%) |
| GGAA | 293 | 165 | 64.0 | TTCT (38%); TTTC (25%); TTGC (16%) |
| GGAC | 158 | 277 | 36.2 | GTCT (32%); GTTC (24%); GTGC (12%) |
| GGAG | 161 | 435 | 27.0 | CTCT (27%); TTCC (20%); CTTC (18%) |
| GGAT | 170 | 446 | 27.6 | GTCC (25%); ATCT (21%); ATTC (18%) |
| GGCA | 165 | 298 | 35.7 | TGCT (33%); TGTC (20%); TGGC (17%) |
| GGCC | 138 | 345 | 28.5 | GGCT (28%); GGTC (23%); GGGC (20%) |
| GGCG | 136 | 445 | 23.4 | TGCC (20%); CGCT (19%); CGTC (15%) |
| GGCT | 126 | 546 | 18.8 | GGCC (18%); TGCC (16%); AGCT (16%) |
| GGGA | 177 | 350 | 33.5 | TCCT (27%); TTCC (25%); TCTC (17%) |
| GGGC | 121 | 468 | 20.6 | GCCT (19%); GTCC (17%); GCTC (16%) |
| GGGG | 100 | 234 | 29.9 | TCCC (21%); CCCT (17%); CCTC (16%) |
| GGGT | 93 | 255 | 26.7 | GCCC (22%); ACCT (14%); ATCC (12%) |
| GGTA | 128 | 259 | 33.1 | TACT (27%); TATC (18%); TGCC (18%) |
| GGTC | 138 | 471 | 22.7 | GATC (19%); GACT (18%); GGCC (17%) |
| GGTG | 90 | 316 | 22.2 | CATC (13%); CTCC (13%); TACC (13%) |
| GGTT | 86 | 240 | 26.3 | GACC (17%); TACC (15%); AACT (13%) |
| GTAA | 248 | 122 | 67.0 | TTAT (28%); TTTC (25%); TTGC (23%) |
| GTAC | 150 | 250 | 37.5 | GTAT (30%); GTGC (28%); GTTC (18%) |
| GTAG | 133 | 377 | 26.1 | CTAT (27%); CTTC (18%); CTGC (18%) |
| GTAT | 125 | 324 | 27.9 | GTAC (24%); ATAT (21%); ATTC (15%) |
| GTCA | 179 | 294 | 37.9 | TGAT (38%); TGGC (25%); TGTC (14%) |
| GTCC | 158 | 322 | 32.8 | GGAT (35%); GGGC (24%); GGTC (19%) |
| GTCG | 117 | 471 | 19.9 | CGAT (21%); CGGC (17%); TGAC (17%) |
| GTCT | 127 | 443 | 22.3 | AGAT (21%); GGAC (20%); TGAC (15%) |
| GTGA | 153 | 309 | 33.1 | TTAC (23%); TCAT (21%); TCGC (17%) |
| GTGC | 112 | 450 | 20.0 | GCAT (27%); GTAC (16%); GCGC (14%) |
| GTGG | 113 | 315 | 26.5 | TCAC (16%); CCAT (15%); CCGC (15%) |
| GTGT | 78 | 298 | 20.8 | GCAC (19%); ACAT (15%); ATAC (14%) |
| GTTA | 130 | 187 | 40.9 | TAAT (29%); TTAC (18%); TGAC (13%) |
| GTTC | 137 | 388 | 26.1 | GAAT (28%); GGAC (17%); GAGC (13%) |
| GTTG | 91 | 369 | 19.8 | CAAT (16%); TAAC (12%); CGAC (11%) |
| GTTT | 90 | 256 | 26.0 | AAAT (19%); GAAC (18%); TAAC (12%) |
| TAAA | 156 | 51 | 75.3 | TTTG (70%); TTTT (20%); TTTC (5%) |
| TAAC | 130 | 87 | 59.8 | GTTG (50%); GTTT (35%); GTTC (5%) |

TABLE 8-continued

Multi-fragment assembly fidelity of 5' phosphorylated 4-base overhangs using T4 DNA ligase and buffer (NEB) and PaqCI (5 minutes at 37° C. then 5 minutes at 16° C. for 60 cycles)

| Overhang | Correct, x10⁻⁵ | Mismatch, x10⁻⁵ | Fidelity[1] | Mismatch Overhangs[2] |
|---|---|---|---|---|
| TAAG | 252 | 152 | 62.5 | CTTT (45%); CTTG (29%); TTTA (13%) |
| TAAT | 231 | 210 | 52.4 | ATTG (36%); GTTA (26%); ATTT (23%) |
| TACA | 156 | 79 | 66.5 | TGTG (56%); TGTT (25%); GGTA (9%) |
| TACC | 128 | 92 | 58.2 | GGTG (43%); GGTT (38%); GGTC (6%) |
| TACG | 182 | 241 | 43.0 | CGTT (31%); CGTG (26%); TGTA (25%) |
| TACT | 214 | 258 | 45.4 | AGTG (29%); GGTA (27%); AGTT (21%) |
| TAGA | 267 | 104 | 72.1 | TCTG (59%); TCTT (27%); TGTA (4%) |
| TAGC | 180 | 244 | 42.4 | GCTG (41%); GCTT (37%); GGTA (8%) |
| TAGG | 151 | 300 | 33.4 | TCTA (30%); CCTG (24%); CCTT (20%) |
| TAGT | 185 | 278 | 40.0 | GCTA (28%); ACTT (19%); ACTG (17%) |
| TATA | 243 | 100 | 70.9 | TATG (50%); TATT (23%); TGTA (11%) |
| TATC | 217 | 224 | 49.2 | GATG (40%); GATT (23%); GGTA (21%) |
| TATG | 166 | 345 | 32.5 | CATG (27%); CTTA (17%); CATT (17%) |
| TATT | 174 | 253 | 40.7 | AATG (21%); GATA (19%); AATT (17%) |
| TCAA | 200 | 77 | 72.2 | TTGG (82%); TTGT (11%); GTGA (5%) |
| TCAC | 153 | 93 | 62.2 | GTGG (55%); GTGT (28%); GGGA (6%) |
| TCAG | 224 | 245 | 47.7 | CTGG (54%); CTGT (18%); TTGA (17%) |
| TCAT | 253 | 268 | 48.5 | ATGG (49%); GTGA (25%); ATGT (11%) |
| TCCA | 200 | 72 | 73.5 | TGGG (71%); TGGT (15%); GGGA (9%) |
| TCCC | 177 | 76 | 70.0 | GGGG (64%); GGGT (24%); GTGA (3%) |
| TCCG | 231 | 315 | 42.3 | CGGG (44%); TGGA (27%); CGGT (19%) |
| TCCT | 222 | 324 | 40.7 | AGGG (39%); GGGA (29%); TGGA (15%) |
| TCGA | 246 | 224 | 52.3 | TCGG (69%); TCGT (12%); TTGA (8%) |
| TCGC | 184 | 309 | 37.4 | GCGG (46%); GCGT (22%); GTGA (17%) |
| TCGG | 171 | 520 | 24.7 | CCGG (32%); TCGA (30%); CTGA (10%) |
| TCGT | 176 | 450 | 28.1 | ACGG (24%); GCGA (22%); ATGA (11%) |
| TCTA | 267 | 153 | 63.6 | TAGG (59%); TGGA (11%); TTGA (11%) |
| TCTC | 250 | 299 | 45.5 | GAGG (46%); GGGA (20%); GAGT (15%) |
| TCTG | 184 | 484 | 27.5 | CAGG (31%); CTGA (19%); CGGA (13%) |
| TCTT | 200 | 357 | 35.9 | AAGG (35%); GAGA (13%); AAGT (11%) |
| TGAA | 259 | 134 | 65.8 | TTCG (55%); TTCT (30%); TTTA (4%) |
| TGAC | 179 | 222 | 44.7 | GTCG (36%); GTCT (30%); GTTA (11%) |
| TGAG | 177 | 399 | 30.8 | CTCG (27%); CTCT (23%); TTCA (18%) |
| TGAT | 195 | 404 | 32.6 | GTCA (28%); ATCT (21%); ATCG (21%) |
| TGCA | 180 | 245 | 42.4 | TGCG (49%); TGCT (27%); TGTA (7%) |
| TGCC | 165 | 280 | 37.1 | GGCT (32%); GGCG (32%); GGTA (17%) |
| TGCG | 155 | 534 | 22.5 | CGCG (24%); TGCA (22%); CGCT (17%) |

TABLE 8-continued

Multi-fragment assembly fidelity of 5' phosphorylated 4-base overhangs using T4 DNA ligase and buffer (NEB) and PaqCI (5 minutes at 37° C. then 5 minutes at 16° C. for 60 cycles)

| Overhang | Correct, x10$^{-5}$ | Mismatch, x10$^{-5}$ | Fidelity[1] | Mismatch Overhangs[2] |
|---|---|---|---|---|
| TGCT | 144 | 483 | 22.9 | GGCA (20%); AGCG (19%); AGCT (14%) |
| TGGA | 200 | 243 | 45.2 | TCCG (36%); TCCT (21%); TTCA (16%) |
| TGGC | 132 | 444 | 23.0 | GCCG (20%); GCCT (16%); GTCA (16%) |
| TGGG | 106 | 267 | 28.5 | TCCA (19%); CCCG (18%); CCCT (14%) |
| TGGT | 97 | 247 | 28.3 | GCCA (25%); ACCG (14%); ACCT (11%) |
| TGTA | 156 | 156 | 50.0 | TACG (39%); TACT (20%); TGCA (12%) |
| TGTC | 148 | 360 | 29.1 | GACG (23%); GACT (19%); GGCA (17%) |
| TGTG | 102 | 295 | 25.6 | CACG (22%); TACA (15%); CACT (14%) |
| TGTT | 93 | 191 | 32.7 | AACG (17%); GACA (16%); AACT (15%) |
| TTAA | 179 | 55 | 76.5 | TTAG (33%); TTGA (18%); TTAT (18%) |
| TTAC | 248 | 231 | 51.8 | GTGA (30%); GTAG (27%); GTTA (14%) |
| TTAG | 157 | 244 | 39.1 | CTAG (26%); CTTA (15%); CTGA (14%) |
| TTAT | 167 | 165 | 50.4 | GTAA (21%); ATAG (19%); ATGA (14%) |
| TTCA | 259 | 168 | 60.6 | TGAG (42%); TGGA (23%); TGAT (15%) |
| TTCC | 293 | 268 | 52.2 | GGAG (33%); GGGA (32%); GGAT (12%) |
| TTCG | 196 | 489 | 28.6 | CGAG (26%); CGGA (20%); TGAA (15%) |
| TTCT | 191 | 359 | 34.7 | AGAG (19%); GGAA (18%); AGGA (14%) |
| TTGA | 200 | 137 | 59.4 | TCAG (30%); TCAT (15%); TCGA (13%) |
| TTGC | 162 | 397 | 29.0 | GCAG (20%); GCGA (17%); GCTA (12%) |
| TTGG | 99 | 284 | 25.8 | TCAA (22%); CCAG (21%); CCGA (12%) |
| TTGT | 106 | 158 | 40.2 | GCAA (19%); ACAG (18%); ACGA (9%) |
| TTTA | 156 | 53 | 74.4 | TAAG (38%); TAAT (19%); TATA (12%) |
| TTTC | 198 | 306 | 39.2 | GAAG (20%); GGAA (13%); GAAT (12%) |
| TTTG | 113 | 253 | 30.8 | CAAG (25%); TAAA (14%); CTAA (8%) |
| TTTT | 100 | 104 | 49.1 | AAAG (19%); AAAT (12%); ATAA (11%) |

[1]Fidelity is calculated as the fraction of correct ligations divided by the total fraction of ligations for a given overhang.
[2]The most frequently observed mismatch partners are given for each overhang. All overhangs are written in the 5'-to-3' direction. The numbers in parenthesis give the percentage for the given mismatch ligation relative to the total number of mismatch ligations for the overhang.

Segment options for use in assembly of a coronavirus genome using the multi-fragment assembly method.

TABLE 9

Segments of a 12-Fragment viral genome (Genbank ID: NC_045512)

| Fragment # | Range | Length | 5' End | 3' End |
|---|---|---|---|---|
| 1 | 1-2501 | 2531 bp |  | AGTG |
| 2 | 2502-4993 | 2522 bp | CACT | TAAT |
| 3 | 4994-7479 | 2516 bp | ATTA | TGAA |
| 4 | 7480-9967 | 2518 bp | TTCA | TTGC |
| 4 | 9968-12468 | 2531 bp | GCAA | TTTG |
| 5 | 12469-14945 | 2507 bp | CAAA | ACCA |
| 6 | 14946-17436 | 2521 bp | TGGT | GGTC |

TABLE 9-continued

Segments of a 12-Fragment viral genome (Genbank ID: NC_045512)

| Fragment # | Range | Length | 5' End | 3' End |
|---|---|---|---|---|
| 7 | 17437-19926 | 2520 bp | GACC | TAGA |
| 8 | 19927-22437 | 2541 bp | TCTA | AAGT |
| 9 | 22438-24912 | 2505 bp | ACTT | GTCT |
| 11 | 24913-27405 | 2523 bp | AGAC | AAAG |
| 12 | 27406-29903 | 2528 bp | CTTT | |

TABLE 10

Segments of a 24-Fragment Coronavirus CV-2 viral genome (Genbank ID: NC_045512)

| Fragment # | Range | Length | 5' End | 3' End |
|---|---|---|---|---|
| 1 | 1-1245 | 1275 bp | | TTCA |
| 2 | 1246-2500 | 1285 bp | TGAA | GTGT |
| 3 | 2501-3735 | 1265 bp | ACAC | AGGG |
| 4 | 3736-4985 | 1280 bp | CCCT | TCTA |
| 5 | 4986-6234 | 1279 bp | TAGA | AACA |
| 6 | 6235-7470 | 1266 bp | TGTT | ACCG |
| 7 | 7471-8729 | 1289 bp | CGGT | GTAG |
| 8 | 8730-9964 | 1265 bp | CTAC | CGAG |
| 9 | 9965-11220 | 1286 bp | CTCG | GACC |
| 10 | 11221-12468 | 1278 bp | GGTC | TTTG |
| 11 | 12469-13713 | 1275 bp | CAAA | AATC |
| 12 | 13714-14949 | 1266 bp | GATT | GAAA |
| 13 | 14950-16201 | 1282 bp | TTTC | TCAT |
| 14 | 16202-17451 | 1280 bp | ATGA | CAGG |
| 15 | 17452-18690 | 1269 bp | CCTG | TGGA |
| 16 | 18691-19939 | 1279 bp | TCCA | GCTA |
| 17 | 19940-21190 | 1281 bp | TAGC | TCAG |
| 18 | 21191-22437 | 1277 bp | CTGA | AAGT |
| 19 | 22438-23680 | 1273 bp | ACTT | AGTA |
| 20 | 23681-24921 | 1271 bp | TACT | AAAT |
| 21 | 24922-26157 | 1266 bp | ATTT | TAAC |
| 22 | 26158-27405 | 1278 bp | GTTA | AAAG |
| 23 | 27406-28649 | 1274 bp | CTTT | TTGT |
| 24 | 28650-29903 | 1284 bp | ACAA | |

TABLE 11

Segments of a 50-Fragment viral genome (Coronavirus CV-2 genome) (Genbank ID: NC_045512)

| Fragment # | Range | Length | 5' End | 3' End |
|---|---|---|---|---|
| 1 | 1-595 | 625 bp | | CCAC |
| 2 | 596-1194 | 629 bp | GTGG | TTCA |
| 3 | 1195-1784 | 620 bp | TGAA | TTAC |
| 4 | 1785-2395 | 641 bp | GTAA | GCGT |
| 5 | 2396-2996 | 631 bp | ACGC | CCAG |
| 6 | 2997-3594 | 628 bp | CTGG | AGCA |
| 7 | 3595-4189 | 625 bp | TGCT | TAGT |
| 8 | 4190-4792 | 633 bp | ACTA | AGGA |
| 9 | 4793-5387 | 625 bp | TCCT | TTAG |
| 10 | 5388-5989 | 632 bp | CTAA | GCTC |
| 11 | 5990-6579 | 620 bp | GAGC | AGTA |
| 12 | 6580-7170 | 621 bp | TACT | AGAA |
| 13 | 7171-7781 | 641 bp | TTCT | TTAT |
| 14 | 7782-8366 | 615 bp | ATAA | TGCG |
| 15 | 8367-8965 | 629 bp | CGCA | GTTT |
| 16 | 8966-9561 | 626 bp | AAAC | GAAT |
| 17 | 9562-10166 | 635 bp | ATTC | GGAC |
| 18 | 10167-10759 | 623 bp | GTCC | ACTT |
| 19 | 10760-11364 | 635 bp | AAGT | ATAC |
| 20 | 11365-11968 | 634 bp | GTAT | CTTT |
| 21 | 11969-12557 | 619 bp | AAAG | TGGA |
| 22 | 12558-13159 | 632 bp | TCCA | TACA |
| 23 | 13160-13754 | 625 bp | TGTA | TATT |
| 24 | 13755-14351 | 627 bp | AATA | TCTG |
| 25 | 14352-14946 | 625 bp | CAGA | AACC |
| 26 | 14947-15539 | 623 bp | GGTT | CGTG |
| 27 | 15540-16154 | 645 bp | CACG | CATA |
| 28 | 16155-16749 | 625 bp | TATG | TAGG |
| 29 | 16750-17343 | 624 bp | CCTA | CTAT |
| 30 | 17344-17937 | 624 bp | ATAG | TTGC |
| 31 | 17938-18543 | 636 bp | GCAA | ACAT |
| 32 | 18544-19129 | 616 bp | ATGT | TCTT |
| 33 | 19130-19743 | 644 bp | AAGA | ACAA |
| 34 | 19744-20324 | 611 bp | TTGT | AACG |
| 35 | 20325-20936 | 642 bp | CGTT | CAGC |
| 36 | 20937-21526 | 620 bp | GCTG | GAAA |
| 37 | 21527-22131 | 635 bp | TTTC | TTCC |

TABLE 11-continued

Segments of a 50-Fragment viral genome (Coronavirus CV-2 genome) (Genbank ID: NC_045512)

| Fragment # | Range | Length | 5' End | 3' End |
|---|---|---|---|---|
| 38 | 22132-22724 | 623 bp | GGAA | TCAT |
| 39 | 22725-23320 | 626 bp | ATGA | TAAT |
| 40 | 23321-23915 | 625 bp | ATTA | TTGA |
| 41 | 23916-24514 | 629 bp | TCAA | TGTC |
| 42 | 24515-25117 | 633 bp | GACA | TGAG |
| 43 | 25118-25706 | 619 bp | CTCA | GAGA |
| 44 | 25707-26310 | 634 bp | TCTC | CGAA |
| 45 | 26311-26909 | 629 bp | TTCG | TGGT |
| 46 | 26910-27511 | 632 bp | ACCA | TCGT |
| 47 | 27512-28115 | 634 bp | ACGA | TATC |
| 48 | 28116-28703 | 618 bp | GATA | TGAT |
| 49 | 28704-29303 | 630 bp | ATCA | TTTG |
| 50 | 29304-29903 | 630 bp | CAAA | |

Example 7: An Automated Workflow for Generating an Ordered Assembly of Polynucleotides into a Target Polynucleotide A workflow could be largely or entirely accomplished in a single machine with various component inputs presented together or sequentially. In a hypothetical workflow, a desired sequence is entered into the computer. The computer then provides an output describing the suitable fragments, and overhangs derived from the ligation frequency table to which sets of rules have been attached for ordered assembly of the desired sequence.

The computer output might interface with a lab on a chip or other instrument containing multiple reagent compartments. The regulation of reaction steps may be controlled on a chip by electrowetting based liquid transfer. For example, AQdrop® platform (Sharp Life Sciences, Oxford, UK) enables micro-scale droplets to be electronically manipulated on the "lab-on-a-chip" device. Another platform is an acoustic based-liquid transfer (Beckman Coulter, Brea, CA). Alternatively, the workflow may be performed using magnetic beads to remove unwanted enzymes/primers from a reaction vessel at different stages as needed.

Accordingly, fragments may be synthesized in situ or from a secondary source according to the computer output. The synthesized fragments can be amplified by cloning or by an amplification method such as PCR. The latter may be achieved by combining all the separate synthesized fragments in a single mixture and performing multiplex PCR. The polymerase may be inactivated, and a ligase and a restriction endonuclease added to achieve ordered DNA assembly using the methods described herein. The subsequent assembled target DNA may be: (i) incorporated into a vector that in turn is introduced into a host cell by transformation of the vector; (ii) encapsulated into a virus and introduced into a host cell by infection; (iii) in the form of naked DNA or with a chaperone molecule, introduced directly into a eukaryotic cell; (iv) introduced into an in vitro expression system to determine whether the transcript of the assembled DNA is functional. Optionally, a product of the assembly could be moved to a platform location to perform sequencing such as by means of a whole molecule sequencer (Oxford Nanopore or Pacific Biosystems).

Ordered assembly of DNA molecules using the methods described herein, is a powerful tool for synthesizing individual genes or metabolic pathways and also for potentially modifying eukaryotic cells genetically. It also provides a means for synthesizing toxic proteins such as novel nucleases, to determine their specificity and other functions. Ordered assemblies encoding toxic proteins may be transcribed using an in vitro transcription system (New England Biolabs, Ipswich, MA) and then tested for DNA cleavage to determine whether a desired function is achieved. The selected positive proteins can then be manufactured in cells under specialized conditions.

In one example of an automated workflow where a large molecule is built from small fragments, a first step would be to synthesize a set of fragments of at least 20 bases in length enzymatically (e.g., using a terminal transferase) or by chemical synthesis or as a product of PCR from a larger substrate or a set of overlapping fragments.

These fragments can be assembled using the protocols described herein. An assembly of 50 fragments of 25-bases would generate a target polynucleotide of 1000 bases. The restriction endonuclease and ligase can optionally be heat killed at 60° C. prior to the next assembly step.

The assembly process may be repeated again with the newly created polynucleotide fragments. For example, primers, aptamers and polymerases for amplifying newly formed polynucleotide fragments from the previous step can then be generated by multiplex PCR. Subsequently, the amplified polynucleotide fragments are subjected to restriction endonuclease cleavage and ligation to generate a 12,500 bp fragment from 50×250 bp polynucleotides or a 50,000 bp polynucleotide from 50×1000 bp fragments.

The assembly can then be repeated for example by combining 50×12,500 (625 Kb) fragments or the 50×50,000 bp fragments (2.5 Mb), followed by cleavage and ligation to generate a 625 kb or 2.5 Mb target polynucleotide.

Another example of a workflow would be a one-step DNA assembly using a large number of DNA fragments of a size ranging from 200-1000 bp.

The efficiency of ligation of fragments depends on the overhangs, enzymes and experimental conditions but does not depend on the length of the polynucleotide fragments used in assembly at least up to 1 kb. The assembly of large number of fragments used in the assembly beyond 24 fragments may be preferentially accomplished by extended incubation periods. Where these incubation periods exceed 24 hours, it may be preferable to use a static ligation protocol instead of touch-down or drop-down protocol. The wt T4 ligase may be used in thermocycling up to temperatures defined by drop-down conditions of 42° C./16° C. Above 42° C., a thermostable ligase is preferable.

Proposed Uses of the Workflow Described Herein

One tube, multiple constructs: emulsified ordered assembly workflow could enable users to generate different constructs from multi-fragment in a small droplet-based format where "positive" drops can be sorted for downstream applications by FACS. Mismatch connections during ordered assembly could enable users to generate different variations of constructs in one tube by the purposeful use of an overhang(s) that pair well with multiple partners. For example, a user could generate the same genetic circuit with several different promoters in one tube and identify the best construct through genetic screening.

Assembly of higher order DNA structures (using non-standard DNA parts). DNA Origami could enable users to assemble DNA structures to facilitate transfection and consistent genetic regulation by controlling shape of assembled molecule. Branched Construct Generation could enable users to create futuristic constructs with branched configurations for parallel regulation. For example, use of a non-standard part assembly fragments (1 duplex to 2 duplex connectors etc.) could position to coding sequence close to the same insulator element.

Mixed overhang length for ordered assembly resulting from the use of more than one Type IIS enzyme could enable maximizing fragments numbers for assembly and permit users to increase the numbers of overhangs possible in a single reaction by mixing orthogonal sets of overhangs with different lengths. This approach could also generate a final construct with a bubble to facilitate downstream applications (including strand invasion or cleavage of the product by nucleases (e.g., T7 endo I)).

Having now described an example embodiment, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention.

What is claimed is:

1. A synthetic self-complementary oligonucleotide that comprises a double-stranded region and a single strand loop, wherein the double-stranded region contains a recognition sequence for PaqCI, has unligatable 3' and 5' ends and cannot be cleaved by PaqCI.

2. A reaction mixture, comprising:
(a) a synthetic self-complementary oligonucleotide comprising a double-stranded region and a single strand loop, wherein the double-stranded region contains a PaqCI recognition sequence, has unligatable 3' and 5' ends, and cannot be cleaved by PaqCI; and
(b) PaqCI or a variant thereof having an amino acid sequence that has at least 90% amino acid sequence identity with SEQ ID NO:1.

3. The reaction mixture according to claim 2, wherein the double-stranded region is 10-50 base pairs in length.

4. The reaction mixture according to claim 2, wherein the oligonucleotide is less than 110 nucleotides in length.

5. The reaction mixture according to claim 2, wherein the 3' end of the oligonucleotide is not a 3' hydroxyl.

6. The reaction mixture according to claim 2, wherein the 5' end of the oligonucleotide is not a 5' phosphate.

7. The oligonucleotide of claim 1, wherein the recognition sequence is (5'-CACCTGC-3'/3'-GCAGGTG-5').

8. The reaction mixture according to claim 2, wherein the ratio of PaqCI to the synthetic self-complementary oligonucleotide is in the range of 1 unit PaqCI: 0.75 pmole-9 pmole oligonucleotide.

9. The reaction mixture of claim 2, further comprising a double-stranded DNA substrate, wherein the substrate contains a recognition sequence for PaqCI and can be cleaved by PaqCI to produce a 4-base overhang.

10. The reaction mixture according to claim 9, wherein the recognition sequence in the DNA substrate is (5'-CACCTGC-3'/3'-GCAGGTG-5').

11. The reaction mixture of claim 2, further comprising a DNA ligase.

12. The reaction mixture of claim 11, wherein the DNA ligase is selected from the group consisting of T4 DNA ligase, T3 DNA ligase, T7 DNA ligase, PBCV-1 DNA ligase and human ligase 3 (hLig3).

13. The reaction mixture according to claim 2, further comprising a plurality of plasmid or PCR products that contain fragments that are each flanked by recognition sites for PaqCI and wherein cleavage of the plasmid or PCR products by PaqCI or variant thereof produces fragments with different 4-base overhangs.

14. The reaction mixture of claim 11, wherein the ratio of the PaqCI to ligase is 2.5-20 PaqCI Units to 200-800 ligase Units.

15. The reaction mixture according to claim 2, wherein the reaction mixture further comprises one or more of: a DNA repair enzyme, a deadenylase, and/or a crowding agent.

* * * * *

SEQUENCE LISTING

```
<160> NUMBER OF SEQ ID NOS: 4

<210> SEQ ID NO 1
<211> LENGTH: 510
<212> TYPE: PRT
<213> ORGANISM: Artificial Sequence
<220> FEATURE:
<223> OTHER INFORMATION: Synthetic construct

<400> SEQUENCE: 1

Met Pro Tyr Asp His Asn Ala Glu Ala Asp Phe Ala Ala Ser Glu Val
1               5                   10                  15

Ala Arg Met Leu Val Ala Asp Pro Gly Leu Cys Tyr Asp Ala Ala Ser
            20                  25                  30

Leu Pro Ala Ser Ile Ser Ala Ser Ala Ser Tyr Glu Pro Ser Ala Ala
        35                  40                  45

Gly Trp Pro Lys Ala Asp Gly Leu Val Ser Val Leu Glu Gly Gly Thr
    50                  55                  60

Ser Thr Gln Arg Ala Ile Ala Leu Glu Tyr Lys Arg Pro Gln Glu Gly
65                  70                  75                  80

Ile His Gly Leu Leu Thr Ala Ile Gly Gln Ala His Gly Tyr Leu His
                85                  90                  95

Lys Gly Tyr Ser Gly Ala Ala Ile Val Ile Pro Gly Arg Tyr Ser Ser
            100                 105                 110

His Pro Thr Pro Ala Glu Tyr Val Arg Asp Val Leu Asn Ala Ile Ser
        115                 120                 125

Gly Ser Arg Ala Ile Ala Val Phe Ser Tyr Ser Pro Pro Asp Thr Thr
    130                 135                 140

Ser Pro Thr Pro Phe Ala Gly Arg Ile Gln Cys Val Arg Pro Leu Val
145                 150                 155                 160

Phe Asp Ala Gly Arg Val His Leu Arg Pro Ala Asn Gln Gly Pro Lys
                165                 170                 175

Thr Gln Trp Val His Met Arg Glu Gly Ser Thr Thr Arg Asp Ala Phe
            180                 185                 190

Phe Arg Phe Leu Gln Val Ala Lys Arg Leu Ser Ala Asp Pro Thr Ala
        195                 200                 205

Pro Arg Pro Thr Leu Arg Ser Glu Leu Val Ala Ala Ile Gly Arg Leu
    210                 215                 220

Ala Pro Gly Arg Asp Pro Ile Glu Tyr Ile Thr Asn Thr Ala Asp Asn
225                 230                 235                 240

Lys Phe Leu Thr Lys Val Trp Gln Phe Phe Trp Leu Glu Trp Leu Ala
                245                 250                 255

Thr Pro Ala Val Leu Thr Pro Trp Lys Leu Glu Ala Gly Val Tyr Ser
```

```
                 260                 265                 270
Ala Pro Gly Ala Arg Thr Arg Ile Leu Arg Glu Asp Gly Thr Asp Phe
            275                 280                 285
Ser Gln Leu Trp Glu Gly Arg Val Asn Ser Leu Lys Glu Thr Ile Ala
        290                 295                 300
Gly Met Leu Asn Arg Gly Ile Ser Glu Ala Gln Gly Trp Glu Ala
305                 310                 315                 320
Phe Val Gly Gly Ile Ser Ala Thr Gly Gly Gln Asp Lys Gln Gly
                325                 330                 335
Val Arg Ala Arg Ala His Ser Tyr Arg Glu Asp Ile Asp Ser Ala Leu
            340                 345                 350
Ala Gln Leu Arg Trp Ile Glu Asp Asp Gly Leu Pro Thr Asp Gln Gly
        355                 360                 365
Tyr Arg Phe Met Thr Ile Cys Glu Arg Tyr Gly Ala Asn Ser Arg
370                 375                 380
Ala Ala Ile Asp Tyr Met Gly Ala Thr Leu Ile Gln Thr Gly Arg Tyr
385                 390                 395                 400
Ala Ser Phe Leu His Tyr Ile Asn Arg Leu Ser Glu Arg Lys Phe Ala
                405                 410                 415
Glu Asn Pro Leu Ala Tyr Thr Lys Pro Gly Pro Gly Met Pro Val
            420                 425                 430
Phe Thr Glu Glu Ser Tyr Trp Glu Tyr Leu Gln Asp Leu Glu Thr Lys
        435                 440                 445
Leu Thr Asp Glu Leu Arg Val Met Arg Lys Val Ser Gly Arg Ala Arg
450                 455                 460
Pro Arg Val Arg Thr Thr Phe Gln Val Glu Leu Thr Leu Leu Arg Asn
465                 470                 475                 480
Tyr Gly Phe Val Ser Ser Thr Arg His Arg Leu Gly Val Gly Ile Pro
                485                 490                 495
Ile Asp Trp Glu Gln Val Val Gln Ala Leu Asn Val Asp Leu
            500                 505                 510
```

<210> SEQ ID NO 2
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(15)
<223> OTHER INFORMATION: n is a, c, g, or t

<400> SEQUENCE: 2
cacctgcnnn nnnnn                                                    15

<210> SEQ ID NO 3
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(15)
<223> OTHER INFORMATION: n is a, c, g, or t

<400> SEQUENCE: 3
gtggacgnnn nnnnn                                                    15

```
<210> SEQ ID NO 4
<211> LENGTH: 1620
<212> TYPE: DNA
<213> ORGANISM: Artificial Sequence
<220> FEATURE:
<223> OTHER INFORMATION: Synthetic construct

<400> SEQUENCE: 4
accatcatta cccattcact gcccctcctt ttacaacctc ctcactccca aaaccctggc      60
cttacccaac ttaatcccct tccaccacat ccccctttcc ccacctcccc taatagccaa     120
cacgccccca cccatcgccc ttcccaacag ttgcgcagcc tgaatggcga atggcgcttt     180
gcctcctttc ccccaccaca agccgtcccg caaagctggc tggagtgcga tcttcctcac     240
ccccatactc tcctcgtccc ctcaaactgc cacatccacg gttaccatgc gcccatctac     300
accaacctaa cctatcccat taccctcaat ccgccgtttc ttcccaccca caatccgacc     360
cgttcttact cgctcacatt taatgttcat caaacctccc tacaccaacc ccacacccca     420
attatttttc atcccgttaa ctccgcgttt catctctcct gcaaccccc ctccctccct     480 tacccccacc acagtcgttt gccgtctgaa tttgacctca gcgcattttt acgccccca     540 caaaaccccc tcgccctcat cgtcctcct tgcagtgacc ccagttatct cgaagatcac     600
gatatctccc ccatcaccc cattttccct cacctctcct tcctccataa acccactaca     660
caaatcagcg atttccatgt tgccactccc tttaatgatc atttcagccc cgctgtactg     720
caggctgaag ttcagatgtc ccgcgacttc cctcactacc tacgcctaac actttcttta     780
tggcaccctc aaacccacct ccccacccgc acccccccctt tccccgctca aattatccat     840
caccctcctc cttatcccca tccctcaca ctacctctca acctccaaaa ccccaaactc     900
tccacccccc aaatccccaa tctctatcct cccctccttg aactccacac ccccacccc     960 accctgattc aaccacaacc ctcccatctt cccttccccc cacctcccca ttgaaaatcc    1020
tctcctcctc ctgaacccca accccttcct cattccaccc cttaaccctc accaccatca    1080
tcctctccat cctcacgtca tccatcacca caccatcctc caccatatcc tcctcatcaa    1140
ccacaacaac tttaaccccc tcccctgttc ccattatccc aaccatcccc tctgctacac    1200
cctctccgac cgctaccccc tctatctcct ccatgaaccc aatattcaaa cccaccgcat    1260
cctcccaatc aatcctctca cccatcatcc ccgctcccta cccccatca cccaaccct    1320 aaccccaatc ctccaccccc atcctaatca ccccactctc atcatctcct ccctcgccaa    1380
tcaatcaccc caccccccta atcaccaccc gctctatccc tgcatcaaat ctctccatcc    1440
ttcccccccc ctgcactatc aaccccccc accccacacc accccaccc atattatttc    1500 ccccatctac ccccccctcc atcaacacca ccccttcccc cctctcccca aatcctccat    1560
caaaaaatcc ctttccctac ctccacacac cccccccctc atcctttccc aataccccca    1620
```